US009884910B2

(12) United States Patent
Fromond et al.

(10) Patent No.: US 9,884,910 B2
(45) Date of Patent: Feb. 6, 2018

(54) ANTI-PDGF-C ANTIBODIES

(71) Applicant: ThromboGenics NV, Heverlee (BE)

(72) Inventors: Claudia Fromond, Fleury en Biere (FR); Hoa Thu Ngo, Leuven (BE); Richard Zwaal, Weerde (BE); Sofie Notebaert, Mortsel (BE)

(73) Assignee: ThromboGenics NV, Heverlee/Leuven (BE)

( * ) Notice: Subject to any disclaimer, the term of this patent is extended or adjusted under 35 U.S.C. 154(b) by 0 days.

(21) Appl. No.: 14/404,052

(22) PCT Filed: Apr. 24, 2013

(86) PCT No.: PCT/EP2013/058513
§ 371 (c)(1),
(2) Date: Nov. 26, 2014

(87) PCT Pub. No.: WO2013/160359
PCT Pub. Date: Oct. 31, 2013

(65) Prior Publication Data
US 2015/0232546 A1 Aug. 20, 2015

Related U.S. Application Data

(60) Provisional application No. 61/637,372, filed on Apr. 24, 2012, provisional application No. 61/727,231, filed on Nov. 16, 2012.

(30) Foreign Application Priority Data

Apr. 24, 2012 (EP) ..................... 12165314
Nov. 16, 2012 (EP) ..................... 12192943

(51) Int. Cl.
*A61K 39/395* (2006.01)
*C07K 16/22* (2006.01)
*A61K 39/00* (2006.01)

(52) U.S. Cl.
CPC .......... *C07K 16/22* (2013.01); *A61K 39/3955* (2013.01); *A61K 2039/505* (2013.01); *C07K 2317/24* (2013.01); *C07K 2317/31* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,304,118 A | 4/1994 | Trese et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,750,373 A | 5/1998 | Garrard et al. | |
| 6,887,982 B1 * | 5/2005 | Gao ................... | A61K 38/1858 530/387.3 |

FOREIGN PATENT DOCUMENTS

| | | |
|---|---|---|
| EP | 1 660 135 | 6/2009 |
| WO | WO 91/19515 | 12/1991 |
| WO | WO 95/00659 | 1/1995 |
| WO | WO 99/02567 | 1/1999 |
| WO | WO 99/47677 | 9/1999 |
| WO | WO 00/18212 | 4/2000 |
| WO | WO 00/34474 | 6/2000 |
| WO | WO 01/28586 | 4/2001 |
| WO | WO 01/77342 | 10/2001 |
| WO | WO 2004/052228 | 6/2004 |
| WO | WO 2005/011742 | 2/2005 |
| WO | WO 2005/087812 | 9/2005 |
| WO | WO 2007/124308 | 11/2007 |
| WO | WO 2008/112003 | 9/2008 |
| WO | WO 2010/033913 | 3/2010 |
| WO | WO 2013/160359 | 10/2013 |

OTHER PUBLICATIONS

Hoogenboom, Nature Biotechnology, 23(9):1105-1116, 2005.*
Arndt et al., "Bispecific diabodies for cancer therapy," *Methods Mol Biol.*, 2003;207:305-21.
Barbas et al., "In vitro evolution of a neutralizing human antibody to human immunodeficiency virus type 1 to enhance affinity and broaden strain cross-reactivity," *Proc Natl Acad Sci U S A.*, Apr. 26, 1994;91(9):3809-13.
Bergsten et al., "PDGF-D is a specific, protease-activated ligand for the PDGF beta-receptor," *Nat Cell Biol.*, May 2001;3(5):512-6.
Boerner et al., "Production of antigen-specific human monoclonal antibodies from in vitro-primed human splenocytes," *J Immunol.*, Jul. 1, 1991;147(1):86-95.
Brennan et al., "Preparation of bispecific antibodies by chemical recombination of monoclonal immunoglobulin G1 fragments," *Science*, Jul. 5, 1985;229(4708):81-3.
Carmeliet, "Angiogenesis in health and disease," *Nat Med.*, Jun. 2003;9(6):653-60.
Chothia et al., "Canonical structures for the hypervariable regions of immunoglobulins," *J Mol Biol.*, Aug. 20, 1987;196(4):901-17.
Clackson et al., "Making antibody fragments using phage display libraries," *Nature*, Aug. 15, 1991;352(6336):624-8.
Cole et al., "Monoclonal Antibodies and Cancer Therapy," 1985 Alan R. Liss, p. 47.
Diaz et al., "Structural analysis, selection, and ontogeny of the shark new antigen receptor (IgNAR): identification of a new locus preferentially expressed in early development," *Immunogenetics*, Oct. 2002;54(7):501-12. Epub Jul. 23, 2002.

(Continued)

Primary Examiner — Marianne P Allen
(74) Attorney, Agent, or Firm — Fish & Richardson P.C.

(57) ABSTRACT

The invention relates to antibodies binding to the PDGF-C antigen and capable of inhibiting binding of PDGF-C to the PDGFRα receptor and of inhibiting PDGFRα activation by PDGF-C. Applications of such antibodies are also disclosed. These include treatment of cancer.

49 Claims, 4 Drawing Sheets

(56) References Cited

OTHER PUBLICATIONS

Figure 1:
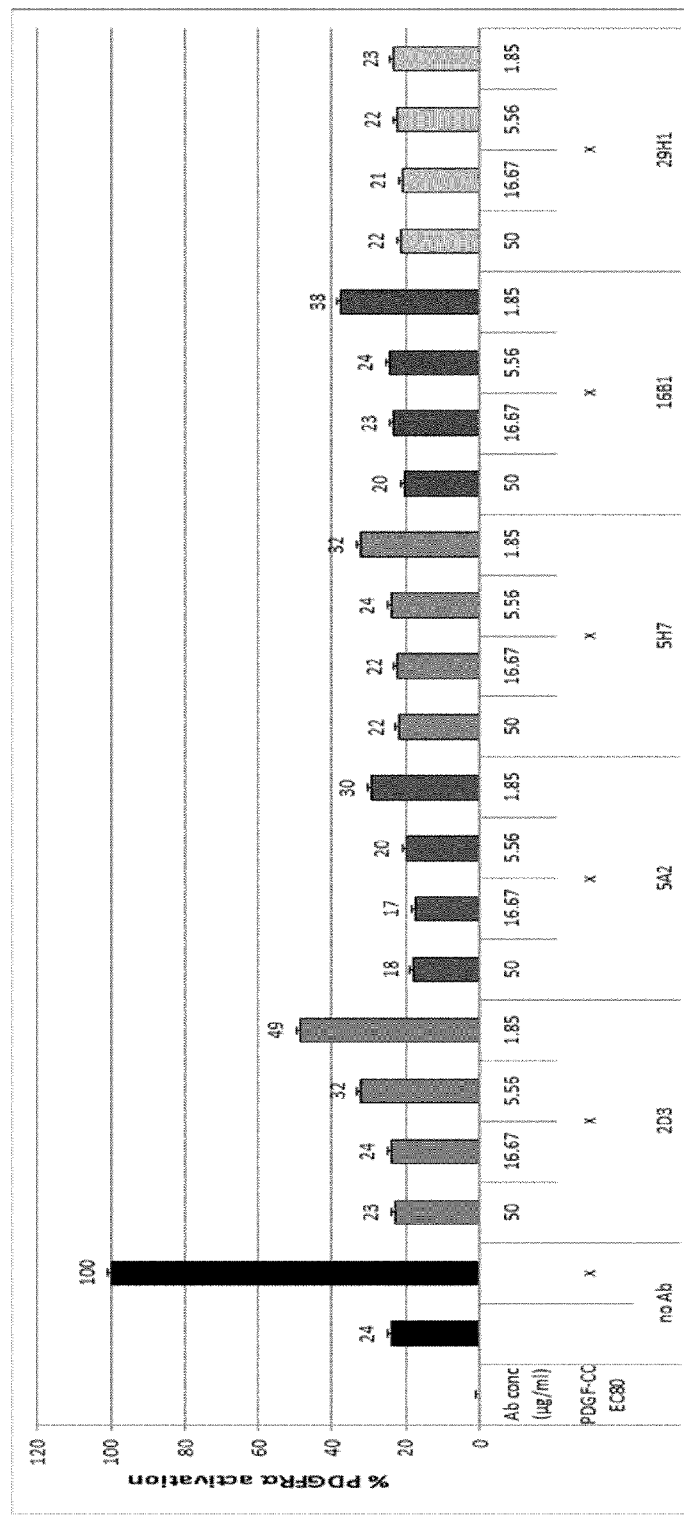

Dooley et al., "Shark immunity bites back: affinity maturation and memory response in the nurse shark, Ginglymostoma cirratum," *Eur J Immunol.*, Mar. 2005;35(3):936-45.
Economides et al., "Cytokine traps: multi-component, high-affinity blockers of cytokine action," *Nat Med.*, Jan. 2003;9(1):47-52. Epub Dec. 16, 2002.
Fishwild et al., "High-avidity human IgG kappa monoclonal antibodies from a novel strain of minilocus transgenic mice," *Nat Biotechnol.*, Jul. 1996;14(7):845-51.
Ekman et al., "Increased mitogenicity of an alphabeta heterodimeric PDGF receptor complex correlates with lack of RasGAP binding," *Oncogene*, Apr. 15, 1999;18(15):2481-8.
Fredriksson et al., "The PDGF family: four gene products form five dimeric isoforms," *Cytokine Growth Factor Rev.*, Aug. 2004;15(4):197-204.
Ghetie et al., "Homodimerization of tumor-reactive monoclonal antibodies markedly increases their ability to induce growth arrest or apoptosis of tumor cells," *Proc Natl Acad Sci U S A.*, Jul. 8, 1997;94(14):7509-14.
Greenberg et al., "A new antigen receptor gene family that undergoes rearrangement and extensive somatic diversification in sharks," *Nature*, Mar. 9, 1995;374(6518):168-73.
Hamada et al., "A novel gene derived from developing spinal cords, SCDGF, is a unique member of the PDGF/VEGF family," *FEBS Lett.*, Jun. 16, 2000;475(2):97-102.
Hawkins et al., "Selection of phage antibodies by binding affinity. Mimicking affinity maturation," *J Mol Biol.*, Aug. 5, 1992;226(3):889-96.
Heap et al., "Analysis of a 17-amino acid residue, virus-neutralizing microantibody," *J Gen Virol.*, Jun. 2005;86(Pt 6):1791-800.
Holliger et al., ""Diabodies": small bivalent and bispecific antibody fragments," *Proc Natl Acad Sci U S A.*, Jul. 15, 1993;90(14):6444-8.
Holliger et al., "Diabodies: small bispecific antibody fragments," *Cancer Immunol Immunother.*, Nov.-Dec. 1997;45(3-4):128-30.
Holliger et al., "Engineered antibody fragments and the rise of single domains," *Nat Biotechnol.*, Sep. 2005;23(9):1126-36.
Hoogenboom et al., "By-passing immunisation. Human antibodies from synthetic repertoires of germline VH gene segments rearranged in vitro," *J Mol Biol.*, Sep. 20, 1992;227(2):381-8.
Ito et al., "Transfer of severe experimental autoimmune encephalomyelitis by IL-12- and IL-18- potentiated T cells is estrogen sensitive," *J Immunol.*, May 1, 2003;170(9):4802-9.
Jackson et al., "In vitro antibody maturation. Improvement of a high affinity, neutralizing antibody against IL-1 beta," *J Immunol.*, Apr. 1, 1995;154(7):3310-9.
Karni et al., "IL-18 is linked to raised IFN-gamma in multiple sclerosis and is induced by activated CD4(+) T cells via CD40-CD40 ligand interactions," *J Neuroimmunol.*, Apr. 2002;125(1-2):134-40.
Köhler et al., "Continuous cultures of fused cells secreting antibody of predefined specificity," *Nature*, Aug. 7, 1975;256(5517):495-7.
Kriangkum et al., "Bispecific and bifunctional single chain recombinant antibodies," *Biomol Eng.*, Sep. 2001;18(2):31-40.
Larochelle et al., "PDGF-D, a new protease-activated growth factor," *Nat Cell Biol.*, May 2001;3(5):517-21.
Lee et al., "Effects of vitreomacular adhesion on anti-vascular endothelial growth factor treatment for exudative age-related macular degeneration," *Ophthalmology*, Jan. 2011;118(1):101-10. doi: 10.1016/j.ophtha.2010.04.015. Epub Aug. 3, 2010.
Lefranc, "Unique database numbering system for immunogenetic analysis," *Immunol Today*, Nov. 1997;18(11):509.
Lei et al., A potential role for PDGF-C in experimental and clinical proliferative vitreoretinopathy, *Invest Ophthalmol Vis Sci.*, May 2007;48(5):2335-42.
Lei et al., "Plasmin is the major protease responsible for processing PDGF-C in the vitreous of patients with proliferative vitreoretinopathy," *Invest Ophthalmol Vis Sci.*, Jan. 2008;49(1):42-8. doi: 10.1167/iovs.07-0776.
Leung et al., "Combined effects of IL-12 and IL-18 on the induction of collagen-induced arthritis," *J Immunol.*, Jun. 15, 2000;164(12):6495-502.
Li et al., "PDGF-C is a new protease-activated ligand for the PDGF alpha-receptor," *Nat Cell Biol.*, May 2000;2(5):302-9.
Li et al., "PDGF-D is a potent transforming and angiogenic growth factor," *Oncogene*, Mar. 13, 2003;22(10):1501-10.
Li et al., "Novel PDGF family members: PDGF-C and PDGF-D," *Cytokine Growth Factor Rev.*, Apr. 2003;14(2):91-8.
Lokker et al., "Platelet-derived growth factor (PDGF) autocrine signaling regulates survival and mitogenic pathways in glioblastoma cells: evidence that the novel PDGF-C and PDGF-D ligands may play a role in the development of brain tumors," *Cancer Res.*, Jul. 1, 2002;62(13):3729-35.
Lonberg et al., "Antigen-specific human antibodies from mice comprising four distinct genetic modifications," *Nature*, Apr. 28, 1994;368(6474):856-9.
Lonberg et al., "Human antibodies from transgenic mice," *Int Rev Immunol.*, 1995;13(1):65-93.
Lu et al., "Simultaneous blockade of both the epidermal growth factor receptor and the insulin-like growth factor receptor signaling pathways in cancer cells with a fully human recombinant bispecific antibody," *J Biol Chem.*, Jan. 23, 2004;279(4):2856-65. Epub Oct. 23, 2003.
Marks et al., "By-passing immunization. Human antibodies from V-gene libraries displayed on phage," *J Mol Biol.*, Dec. 5, 1991;222(3):581-97.
Marks et al., "By-passing immunization: building high affinity human antibodies by chain shuffling," *Biotechnology (N Y)*, Jul. 1992;10(7):779-83.
Miller et al., "Design, construction, and in vitro analyses of multivalent antibodies," *J Immunol.*, May 1, 2003;170(9):4854-61.
Milstein et al., "Hybrid hybridomas and their use in immunohistochemistry," *Nature*, Oct. 6-12, 1983;305(5934):537-40.
Morrison et al., "Chimeric human antibody molecules: mouse antigen-binding domains with human constant region domains," *Proc Natl Acad Sci U S A.*, Nov. 1984;81(21):6851-5.
Morrison, "Immunology. Success in specification," *Nature*, Apr. 28, 1994;368(6474):812-3.
Muyldermans et al., "Sequence and structure of VH domain from naturally occurring camel heavy chain immunoglobulins lacking light chains," *Protein Eng.*, Sep. 1994;7(9):1129-35.
Muyldermans et al., "Single domain camel antibodies: current status," *J Biotechnol.*, Jun. 2001;74(4):277-302.
Nakanishi et al., "Interleukin-18 regulates both Th1 and Th2 responses," *Annu Rev Immunol.*, 2001;19:423-74.
Nuttall et al., "Isolation of the new antigen receptor from wobbegong sharks, and use as a scaffold for the display of protein loop libraries," *Mol Immunol.*, Aug. 2001;38(4):313-26.
Nuttall et al., "Isolation and characterization of an IgNAR variable domain specific for the human mitochondrial translocase receptor Tom70," *Eur J Biochem.*, Sep. 2003;270(17):3543-54.
Peipp et al., "Bispecific antibodies targeting cancer cells," *Biochem Soc Trans.*, Aug. 2002;30(4):507-11.
R&D Systems Tools for Cell Biology Research™, "Mouse PDGF-C Antibody," Catalog No. AF1447 (revised Mar. 13, 2015), 1 page.
R&D Systems, Catalog No. AF1560.
R&D Systems, Catalog No. 1687-CC/CF.
R&D Systems, Catalog No. 6765-PR.
Reigstad et al., "Structural and functional specificities of PDGF-C and PDGF-D, the novel members of the platelet-derived growth factors family," *FEBS J.*, Nov. 2005;272(22):5723-41.
Reigstad et al., "Platelet-derived growth factor (PDGF)-C, a PDGF family member with a vascular endothelial growth factor-like structure," *J Biol Chem.*, May 9, 2003;278(19):17114-20. Epub Feb. 20, 2003.
Schier et al., "Identification of functional and structural amino-acid residues by parsimonious mutagenesis," *Gene.*, Mar. 9, 1996;169(2):147-55.

(56) References Cited

OTHER PUBLICATIONS

Sheets et al., "Efficient construction of a large nonimmune phage antibody library: the production of high-affinity human single-chain antibodies to protein antigens," *Proc Natl Acad Sci U S A.*, May 26, 1998;95(11):6157-62.

Shopes, "A genetically engineered human IgG mutant with enhanced cytolytic activity," *J Immunol.*, May 1, 1992;148(9):2918-22.

Smith et al., "Recombinant polymeric IgG: an approach to engineering more potent antibodies," *Biotechnology (N Y)*, Jul. 1994;12(7):683-8.

Staerz et al., "Hybrid antibodies can target sites for attack by T cells," *Nature*, Apr. 18-24, 1985;314(6012):628-31.

Vaughan et al., "Human antibodies with sub-nanomolar affinities isolated from a large non-immunized phage display library," *Nat Biotechnol.*, Mar. 1996;14(3):309-14.

Wolff et al., "Monoclonal antibody homodimers: enhanced antitumor activity in nude mice," *Cancer Res.*, Jun. 1, 1993;53(11):2560-5.

Wu et al., "Tumor localization of anti-CEA single-chain Fvs: improved targeting by non-covalent dimers," *Immunotechnology*, Feb. 1996;2(1):21-36.

Yamano et al., "Identification of cisplatin-resistance related genes in head and neck squamous cell carcinoma," *Int J Cancer*, Jan. 15, 2010;126(2):437-49. doi: 10.1002/ijc.24704.

Yelton et al., "Affinity maturation of the BR96 anti-carcinoma antibody by codon-based mutagenesis," *J Immunol.*, Aug. 15, 1995;155(4):1994-2004.

Zwerner et al., "Dominant negative PGDF-C inhibits growth of Ewing family tumor cell lines," *Oncogene*, May 30, 2002;21(24):3847-54.

Crawford et al., "PDGF-C Mediates the Angiogenic and Tumorigenic Properties of Fibroblasts Associated with Tumors Refractory to Anti-VEGF Treatment," *Cancer Cell*, Jan. 6, 2009;15:21-34. doi: 10.1016/j.ccr.2008.12.004.

Lei et al., "Focus on Molecules: Platelet-derived Growth Factor C, PDGF-C," *Exp Eye Res.*, May 2008;86(5):711-2. doi:10.1016/j.exer.2007.08.007.

Li et al., "VEGF-independent angiogenic pathways induced by PDGF-C," *Oncotarget*, 2010;1(4):309-14.

Fang et al., "PDGF C is a selective alpha platelet-derived growth factor receptor agonist that is highly expressed in platelet alpha granules and vascular smooth muscle," *Arterioscler Thromb Vasc Biol.*, Apr. 2004;24(4):787-92 and Data Supplement retrieved from http://atvb.ahajournals.org/content/24/4/787/tab-supplemental (4 pages) (retrieved on Aug. 26, 2016).

\* cited by examiner

ANTI-PDGF-C ANTIBODIES

CROSS-REFERENCE TO RELATED APPLICATIONS

This application is the National Stage of International Application No. PCT/EP2013/058513, filed on Apr. 24, 2013, which claims the benefit of European Application No. 12165314.1 and U.S. Provisional Application No. 61/637,372, both filed on Apr. 24, 2012; and European Application No. 12192943.4 and U.S. Provisional Application No. 61/727,231, both filed on Nov. 16, 2012. The contents of all of the above-referenced applications are incorporated by reference in their entirety herein.

FIELD OF THE INVENTION

The invention relates to antibodies binding to the PDGF-C antigen and capable of inhibiting binding of PDGF-C to the PDGFRα, receptor and of inhibiting PDGFRα, activation by PDGF-C. Applications of such antibodies are also disclosed. These include treatment of cancer.

BACKGROUND TO THE INVENTION

Platelet-derived growth factor C (PDGF-C), is, in humans, a 345-amino acid protein which is secreted as a 323-amino acid protein (Hamada et al. 2000, FEBS Lett 475:97-102; Li & Eriksson 2003, Cytokine Growth Factor Rev 14, 91-98). It is a member of the platelet-derived growth factor family which consists of PDGF-A, -B, -C and -D (Li et al. 2000, Nat Cell Biol 2:302-309; Bergsten et al. 2001, Nat Cell Biol 3:512-516; La Rochelle et al. 2001, Nat Cell Biol, 3:517-521). The cysteine knot motif characteristic of the four PDGFs is key to the formation of either homo- or heterodimers (PDGF-AA, -AB, -BB, -CC, -DD) (La Rochelle et al. 2001, Nat Cell Biol 3:517-521; Bergsten et al. 2001, Nat Cell Biol 3:512-516).

In addition to a conserved cystine knot motif, these four growth factors show sequence homology. The four PDGFs are inactive in their monomeric forms. In case of PDGF-C, it is secreted as latent growth factor and proteolytic removal of the N-terminal CUB domain is required for binding to and activation of its receptor. While there are some reports that CUB domains are biologically active, the prevailing thought is that they function to both localize the secreted PDGF-C and repress its activity (Reigstad et al. 2005, FEBS J 272:5723-5741). Proteases capable of activating PDGF-C include plasmin and tissue plasminogen activator (tPA) (Lei et al. 2007, Invest Ophthalmol Vis Sci 48:2335-2342; Lei 2008, Invest Ophthalmol Vis Sci 49:42-48.)

PDGF-C regulates biological processes via homodimeric PDGF receptor alpha (PDGFRα), and possibly via heterodimeric PDGFRα/β. The extracellular region of the receptor consists of five immunoglobulin-like domains while the intracellular part is a tyrosine kinase domain. PDGF-CC binding to its receptor boosts the activity of the tyrosine kinase domain and thereby initiates intracellular signalling events that trigger cellular responses such as proliferation, migration, contraction and survival (Li et al. 2000, Nat Cell Biol 2:302-309). Thus PDGF-C activates intracellular signalling events that engage a host of cellular responses that are essential for numerous biological processes that are required for the development and health of mammals. Mouse knockout studies show that PDGF-C is required for palatogenesis (Fredriksson et al. 2004, Cytokine Growth Factors Rev 15:197-204; Reigstad et al. 2005, J Biol Chem 278:17114-17120). Abnormalities in the PDGF/PDGFR system such as constitutive activation of PDGFR kinases, activating mutations of the PDGFR kinases, autocrine signalling due to overexpression of PDGFs and the PDGFRs, contribute to a number of human diseases, especially malignancies including osteosarcomas, lung carcinomas, gliomas, and malignant astrocytomasand medulloblastomas (Locker et al 2002, Cancer Res 62:3729-3735; Ekman et al. 1999, Oncogene 18:2481-2488; Zwerner & May 2002, Oncogene 21:3847-3854). PDGF-C is a transforming cell factor and promotes tumor growth via several mechanisms including survival and proliferation of tumor cells, chemotaxis for cancer-associated fibroblasts, and tumor neovascularization. It has been demonstrated that PDGF-C induces tumors in nude mice, activates anchorage dependent growth, and is a potent transforming growth factor of NIH/3T3 cells. (Li et al. 2002, Oncogene 22:1501-1510). The in vivo tumourigenesis may partially be explained by PDGFC-mediated VEGF expression, promoting indirect stimulation of tumor angiogenesis. Finally, PDGF-C is upregulated in cancer tumors that are resistant to chemotherapy. In preclinical models of cancer, siRNA-mediated reduction of PDGF-C levels reverses the resistance to cisplatin (Yamano et al. 2010, Int J Cancer 126:437-449).

PDGF-C used to be termed VEGF-E (WO99/47677) or ZVEGF3 (WO00/34474). Although the use of antibodies countering PDGF-C activity (or of bispecific anti-VEGF/anti-PDGF-C antibodies) has been suggested (WO99/47677, WO00/34474, WO01/28586, WO2005/011742, WO00/18212, WO 2005/087812), not any specific monoclonal antibody with demonstrated anti-tumorigenic or anti-angiogenic activity has as yet been reported.

SUMMARY OF THE INVENTION

The invention relates to isolated monoclonal antibodies binding to the antigen PDGF-C with high affinity, capable of inhibiting binding of PDGF-C to PDGFRα and capable of inhibiting activation of PDGFRα by PDGF-C. The above antibodies in particular bind to a peptide defined by SEQ ID NO:96.

Exemplary isolated antibodies binding to the antigen PDGF-C with high affinity, capable of inhibiting binding of PDGF-C to PDGFRα and capable of inhibiting activation of PDGFRα by PDGF-C comprise antibodies comprising either one of the following combinations of complementarity determining region (CDR) amino acid sequences:
  (i) light chain CDR 1 to 3 with amino acid sequences defined in SEQ ID NO: 26, 24 and 25, respectively; and heavy chain CDR 1 to 3 with amino acid sequences defined in SEQ ID NO: 35 to 37, respectively;
  (ii) light chain CDR 1 with amino acid sequence defined in SEQ ID NO: 22 or 23; light chain CDR 2 and 3 with amino acid sequences defined in SEQ ID NO: 24 and 25, respectively; heavy chain CDR 1 with amino acid sequence defined in SEQ ID NO: 27 or 28; heavy chain CDR 2 with amino acid sequence defined in SEQ ID NO: 29, 30 or 31; and heavy chain CDR 3 with amino acid sequence defined in SEQ ID NO: 32, 33 or 34;
  (iii) light chain CDR 1 to 3 with amino acid sequences defined in SEQ ID NO: 22, 24 and 25, respectively; heavy chain CDR 1 with amino acid sequence defined in SEQ ID NO: 27; heavy chain CDR 2 with amino acid sequence defined in SEQ ID NO: 29 or 30; and heavy chain CDR 3 with amino acid sequence defined in SEQ ID NO: 32 or 33;

(iv) light chain CDR 1 to 3 with amino acid sequences defined in SEQ ID NO: 23 to 25, respectively; heavy chain CDR 1 with amino acid sequence defined in SEQ ID NO: 28; heavy chain CDR 2 with amino acid sequence defined in SEQ ID NO: 31; and heavy chain CDR 3 with amino acid sequence defined in SEQ ID NO: 34;

(v) light chain CDR 1 to 3 with amino acid sequences defined in SEQ ID NO: 38, 24, and 25, respectively; heavy chain CDR 1 with amino acid sequence defined in SEQ ID NO: 27; heavy chain CDR 2 with amino acid sequence defined in SEQ ID NO: 30; and heavy chain CDR 3 with amino acid sequence defined in SEQ ID NO: 33; or (vi) an affinity matured antibody of any of (i) to (v).

Any of the above antibodies can be a mammalian antibody, a human antibody or a humanized antibody. Further, any of the above antibodies can be a monovalent or multivalent antibody, and further be monospecific or multispecific provided that the binding to the antigen PDGF-C and the inhibition of activation of PDGFRα by PDGF-C is maintained.

The invention also encompasses antigen-binding fragments of any of the above antibodies.

The invention further relates to isolated nucleic acids encoding any of the above antibodies or antigen-binding fragments.

Any of the above antibodies, antigen-binding fragments or nucleic acids encoding any of them is intended for use as a medicament. Such use can be a single use (monotherapy) or a use in combination with an additional therapeutic agent (combination therapy). To this end, at least one of the above antibodies, antigen-binding fragments or nucleic acids encoding any one of them may be formulated in a pharmaceutical composition which may further comprise a pharmaceutically acceptable carrier and, optionally, an additional therapeutic agent. Said medicament is intended for treatment of cancer, ophthalmologic disorders and disorders characterized by neo-vascularization.

Vectors comprising any of the above nucleic acids and host cells comprising such vector and/or expressing any of the above antibodies or antigen-binding fragments thereof are further part of the invention, as are method for producing any of the above antibodies or antigen-binding fragments thereof.

FIGURE LEGENDS

FIG. 1 illustrates the inhibitory activity of the 5 anti-human PDGF-C antibodies 2D3, 5A2, 5H7, 16B1 and 29H1 on PDGFRα activation by human PDGF-C in the PathHunter® PDGFRα assay. The activator PDGF-C was applied at its EC80 value (see Example 4). Controls without antibody (with or without activator) are also included.

Figure 2:
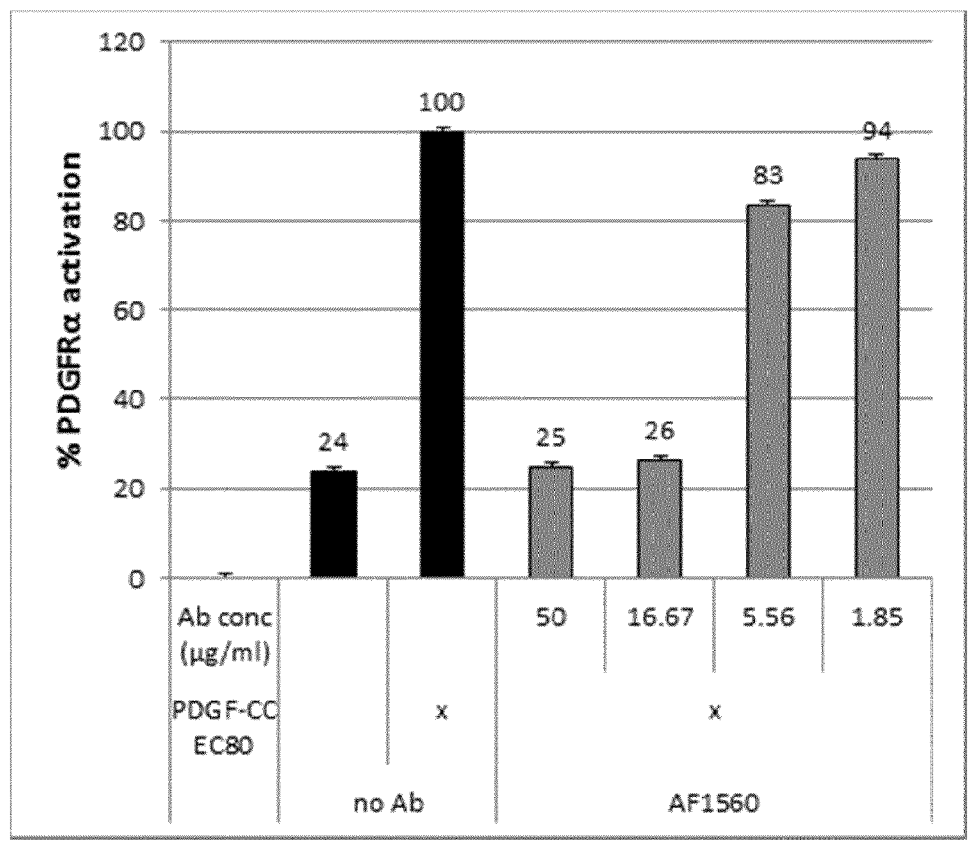

FIG. 2 illustrates the inhibitory activity of the anti-human PDGF-C polyclonal goat IgG antibody (Catalog No. AF1560 from R&D Systems) on PDGFRα activation by human PDGF-C in the PathHunter® PDGFRα assay. The activator PDGF-C was applied at its EC80 value (see Example 4). Controls without antibody (with or without activator) are also included.

Figure 3:
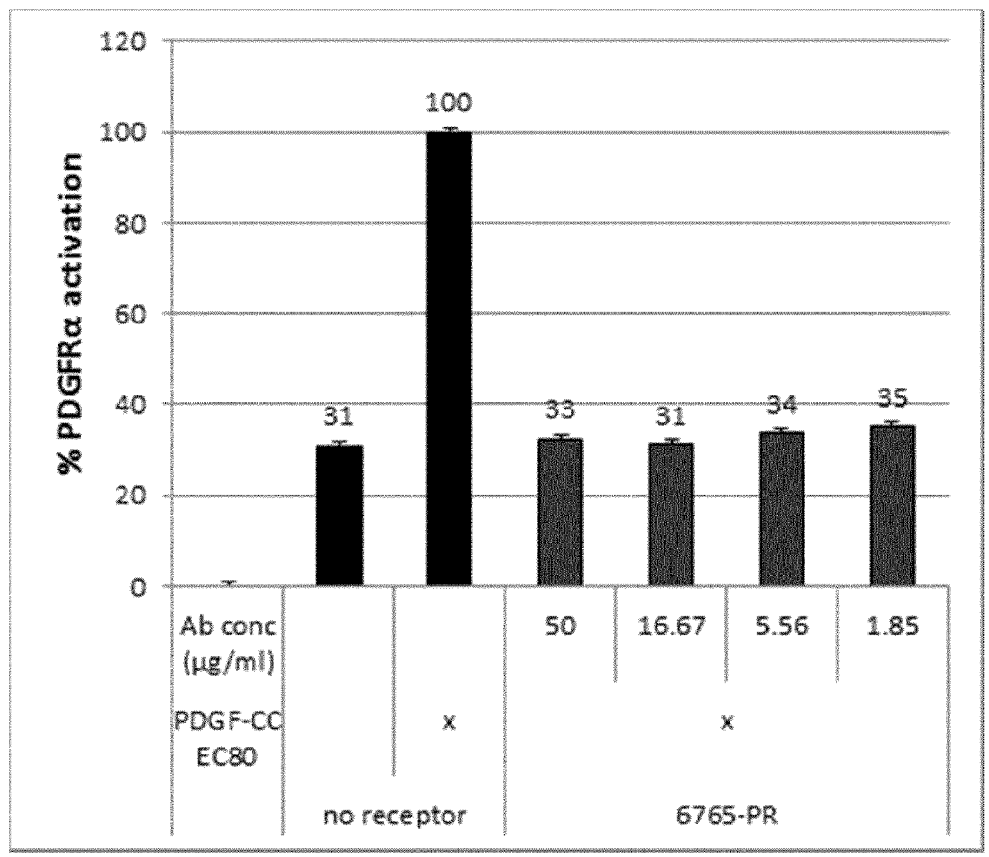

FIG. 3 illustrates the inhibitory activity of the recombinant human PDGFRα, Fc chimera (Catalog No. 6765-PR from R&D Systems) on PDGFRα activation by human PDGF-C in the PathHunter® PDGFRα assay. The activator PDGF-C was applied at its EC80 value (see Example 4). Controls without receptor (with or without activator) are also included.

Figure 4:
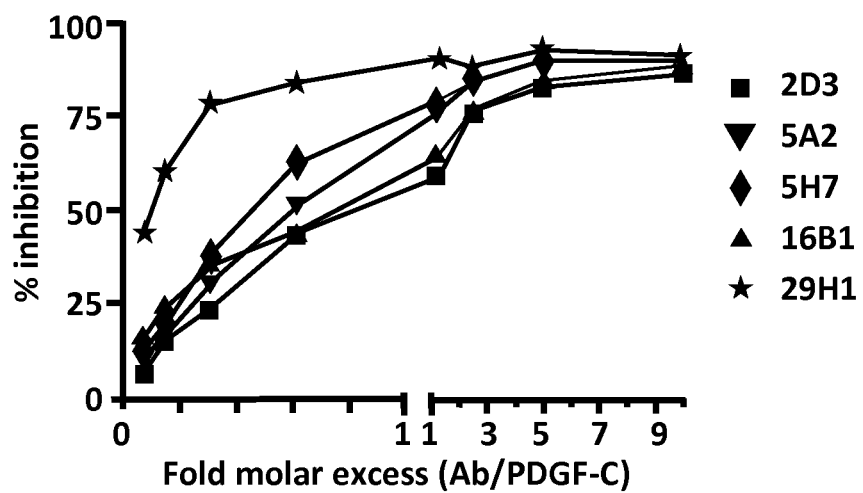

FIG. 4 illustrates the interference of anti-PDGF-C monoclonal antibodies 2D3, 5A2, 5H7, 16B1 and 29H1 with the binding of PDGF-C to its receptor as determined in a competition ELISA setting (see Example 5).

DETAILED DESCRIPTION OF THE INVENTION

The term "PDGF-C" (platelet derived growth factor C) is used herein as generic term which thus may also refer to PDGF-CC. Whereas PDGF-C refers to a monomer, PDGF-CC refers to the homodimeric form of PDGF-C.

Work on PDGF-C as a therapeutic target led to the invention of a series of isolated monoclonal antibodies binding to the antigen PDGF-C with high affinity (see Examples 3 and 9) and capable of inhibiting binding of PDGF-C to PDGFRα, (see Example 5) and of inhibiting activation of PDGFRα, (PDGF receptor alpha) by PDGF-C (see Examples 4 and 9). The therapeutic potential of exemplary antibodies was demonstrated by in vivo inhibition of glioblastoma tumor growth by the antibodies (see Example 7). A need for such antibodies with such therapeutic potential clearly still exists in the art as none seem currently available.

Exemplary isolated antibodies binding to the antigen PDGF-C with high affinity, capable of inhibiting binding of PDGF-C to PDGFRα, and capable of inhibiting activation of PDGFRα, by PDGF-C comprise antibodies binding to the peptide with sequence defined by SEQ ID NO:96.

In particular, the binding of these antibodies to SEQ ID NO:96 can be determined via ELISA. In such ELISA, the binding of said antibodies to PDGF-C is characterized by a signal to background ratio being repeatedly higher than or equal to 3 (three). Specific analysis conditions as used herein are outlined in Example 6 & Legend to Table 6. Affinity of the exemplary antibodies for PDGF-C is in the nanomolar range, in particular the affinity is characterized by a dissociation constant $K_D$ of 10 nM or lower, 9 nM or lower, 8 nM or lower, 7 nM or lower, 6 nM or lower, or 5 nM or lower, for instance with a $K_D$ between 0.5 nM and 2.5 nM, 5 nM or 10 nM (i.e. lower limit of 0.5 nM and higher limit selected from 2.5 nM, 5 nM or 10 nM); or between 0.1 nM and 2.5 nM, 5 nM or 10 nM (i.e. lower limit of 0.1 nM and higher limit selected from 2.5 nM, 5 nM or 10 nM). Such affinity can be determined e.g. by surface plasmon resonance. Specific analysis conditions as used herein are outlined in Example 3.

Exemplary isolated antibodies binding to the antigen PDGF-C with high affinity, capable of inhibiting binding of PDGF-C to PDGFRα, and capable of inhibiting activation of PDGFRα, by PDGF-C comprise antibodies comprising either one of the following combinations of complementarity determining region (CDR) amino acid sequences:

(i) light chain CDR 1 to 3 with amino acid sequences defined in SEQ ID NO: 26, 24 and 25, respectively (i.e. CDR1 is defined in SEQ ID NO:26, CDR2 is defined in SEQ ID NO:24, and CDR3 is defined in SEQ ID NO:25); and heavy chain CDR 1 to 3 with amino acid sequences defined in SEQ ID NO: 35 to 37, respectively;

(ii) light chain CDR 1 with amino acid sequence defined in SEQ ID NO: 22 or 23; light chain CDR 2 and 3 with amino acid sequences defined in SEQ ID NO: 24 and 25, respectively; heavy chain CDR 1 with amino acid sequence defined in SEQ ID NO: 27 or 28; heavy chain CDR 2 with amino acid sequence defined in SEQ ID NO: 29, 30 or 31; and heavy chain CDR 3 with amino acid sequence defined in SEQ ID NO: 32, 33 or 34;

(iii) light chain CDR 1 to 3 with amino acid sequences defined in SEQ ID NO: 22, 24 and 25, respectively; heavy chain CDR 1 with amino acid sequence defined in SEQ ID NO: 27; heavy chain CDR 2 with amino acid sequence defined in SEQ ID NO: 29 or 30; and heavy chain CDR 3 with amino acid sequence defined in SEQ ID NO: 32 or 33;

(iv) light chain CDR 1 to 3 with amino acid sequences defined in SEQ ID NO: 23 to 25, respectively; heavy chain CDR 1 with amino acid sequence defined in SEQ ID NO: 28; heavy chain CDR 2 with amino acid sequence defined in SEQ ID NO: 31; and heavy chain CDR 3 with amino acid sequence defined in SEQ ID NO: 34;

(v) light chain CDR 1 to 3 with amino acid sequences defined in SEQ ID NO: 38, 24, and 25, respectively; heavy chain CDR 1 with amino acid sequence defined in SEQ ID NO: 27; heavy chain CDR 2 with amino acid sequence defined in SEQ ID NO: 30; and heavy chain CDR 3 with amino acid sequence defined in SEQ ID NO: 33; or (vi) an affinity matured antibody of any of (i) to (v).

Any of the above antibodies can be a mammalian antibody, a human antibody or a humanized antibody. Further, any of the above antibodies can be a monovalent or multivalent antibody, and further be monospecific or multispecific provided that the binding to the antigen PDGF-C and the inhibition of activation of PDGFRα, by PDGF-C are maintained.

The invention also encompasses antigen-binding fragments of any of the above antibodies.

The term "antibody" as used herein refers to any naturally occurring antibody or antigen-binding protein the production of which is induced by an immune system (immunoglobulins or IgGs). "Conventional" antibodies comprise two heavy chains linked together by disulfide bonds and two light chains, one light chain being linked to each of the heavy chains by disulfide bonds. Each heavy chain has at one end a variable domain (VH) followed by a number of constant domains (three or four constant domains, CH1, CH2, CH3 and CH4, depending on the antibody class). Each light chain has a variable domain (VL) at one end and a constant domain (CL) at its other end; the constant domains of the light chains each align with the first constant domains of the heavy chains, and the light chain variable domains each align with the variable domains of the heavy chains. This type of antibodies exist in camels, dromedaries and llamas along with an "unconventional" naturally occurring type of antibodies consisting of only two heavy chains, and thus being devoid of light chains. Other "unconventional" naturally occurring antibodies exist in in the serum of nurse sharks (Ginglymostomatidae) and wobbegong sharks (Orectolobidae). These latter antibodies are called Ig new antigen receptors (IgNARs). They are disulfide-bonded homodimers consisting of five constant domains (CNAR) and one variable domain (VNAR). There is no light chain, and the individual variable domains are independent in solution and do not appear to associate across a hydrophobic interface (Greenberg et al. 1995, Nature 374, 168-173; Nuttall et al. 2001, Mol Immunol 38, 313-326; Diaz et al. 2002, Immunogenetics 54, 501-512; Nuttall et al. 2003, Eur J Biochem 270, 3543-3554). Due to the heavy chain dimer structure characteristic of camelid and shark antibodies, these are sometimes termed "Heavy-Chain Mini-Antibodies" (mnHCAbs) or simply "Mini-Antibodies" (mnAbs) (Holliger & Hudson 2005, Nature Biotechnol 23, 1126-1136). The complementary determining region 3 (CDR3) of camel antibodies and shark antibodies is usually longer (comprising about 16-21 amino acids, and about 16-27 amino acids, respectively) than the CDR3 of mouse VH region (comprising about 9 amino acids) (Muyldermans et al. 1994, Prot Eng 7, 1129-1135; Dooley & Flajnik 2005, Eur J Immunol 35, 936-945). Without the light chain, these heavy-chain antibodies bind to their antigens by one single domain, the variable antigen binding domain of the heavy-chain immunoglobulin, referred to as Vab (camelid antibodies) or V-NAR (shark antibodies). These smallest intact and independently functional antigen-binding fragment Vab is referred to as nano-antibody or nanobody (Muyldermans 2001, J Biotechnol 74, 277-302). Multivalent (etc. divalent, trivalent, tetravalent and pentavalent) Vab and/or V-NAR domains may be preferred in some instances due to their potentially higher cellular intake and retention and may be made by recombinant technology or by chemical means, such as described in WO 2010/033913. The variable domains of the light and/or heavy chains are involved directly in binding the antibody to the antigen. The variable domains of naturally occurring light and heavy chains have the same general structure: four framework regions (FRs) connected by three complementarity determining regions (CDRs) (see e.g. Kabat et al. 1991, Sequences of Proteins of Immunological Interest, 5$^{th}$ Ed. Public Health Service, National Institutes of Health, Bethesda, Md.). The CDRs in a light or heavy chain are held in close proximity by the FRs and contribute to the formation of the antigen binding site.

The term "complementarity determining region" or "CDR" as used herein in general refers to the hypervariable regions of light and heavy chains of classical 4-chain antibodies and as defined by the Kabat rules, more in particular the Kabat rules as available on http://www.bioinf.org.uk/abs/ and more particular in the "How to identify the CDRs by looking at a sequence" section.

Alternative rules for determining the CDR regions were defined in the Chothia system (Chothia & Lesk 1987, J Mol Biol 196, 901-917). A further alternative follows a unified CDR determination system as proposed by e.g. Lefranc 1997 (Immunology Today 18, 509).

Antibodies have been modified in order to increase their antigen-binding valency by several means including chemical homodimerization by introducing a thioether bond between 2 IgGs, e.g., Ghetie et al. 1997, Proc Natl Acad Sci USA 94, 7509-7514; WO 99/02567; Wolff et al. 1993, Cancer Res 53, 2560-2565), di- or polymerization via intermolecular disulfide bonding after engineering one or more cysteines into the heavy chain carboxyterminal ends (e.g. Shopes 1992, J Immunol 148, 2918-2922; WO91/19515; Smith & Morrison 1994, BioTechnology 12, 683-688).

Bispecific or bifunctional antibodies have been produced using the quadroma technology based on the somatic fusion of two different hybridoma cell lines expressing murine monoclonal antibodies with the desired specificities of the bispecific antibody (Milstein & Cuello 1983, Nature 305, 537-540). Alternatively, bispecific or bifunctional antibodies can be produced by chemical conjugation of two different mAbs or Ab fragments (Staerz et al. 1985, Nature 314, 628-631; Brennan et al. 1985, Science 229, 81-83). Further, recombinant bispecific or bifunctional antibody formats have been developed (Kriangkum et al. 2001, Biomol Eng 18, 31-40). Amongst them tandem single-chain Fv molecules and diabodies starting from two single-chain Fv (scFv) fragments that recognize different antigens (see Economides et al. 2003, Nat Med 9, 47-52). In tandem scFv molecules (taFv), two scFv molecules with an additional peptide linker are simply connected together. Various linkers can be used to connect the two scFv fragments and linkers with a length of up to 63 residues (Nakanishi et al. 2001, Annu Rev Immunol 19, 423-474). Using a very short Ala3linker or long glycine/serine-rich linkers, expression of soluble tandem scFv molecules in bacteria has been achieved (Leung et al. 2000, J Immunol 164, 6495-6502; Ito et al. 2003, J Immunol 170, 4802-4809; Karni et al. 2002, J Neuroimmunol 125, 134-140) and a preferred linker thereto may be the one as described by Arndt & Krauss 2003, Methods Mol Biol 207, 305-321).

Diabodies are produced from scFv fragments by reducing the length of the linker connecting the VH and VL domain to approximately 5 residues (Peipp & Valerius 2002, Biochem Soc Trans 30, 507-511). This reduction of linker size facilitates dimerization of two polypeptide chains by crossover pairing of the VH and VL domains. Bispecific diabodies are produced by expressing, two polypeptide chains with, either the structure VHA-VLB and VHB-VLA (VH-VL configuration), or VLA-VHB and VLB-VHA (VL-VH configuration) within the same cell. Multivalent "abodies" also exist, such as triabodies and tetrabodies.

To avoid the problem of inactive homodimer formation, one approach to force generation of bispecific diabodies is the production of knob-into-hole diabodies (Holliger et al. 1993, Proc Natl Acad Sci USA 90, 6444-6448). By amino acid changes, a large knob is engineered in the VH domain and a complementary hole is engineered in the VL domain.

Single-chain diabodies (scDb) represent an alternative strategy to improve the formation of bispecific diabody-like molecules (Holliger & Winter 1997, Cancer Immunol Immunother 45, 128-130; Wu et al. 1996, Immunotechnology 2, 21-36). Bispecific single-chain diabodies are produced by connecting the two diabody-forming polypeptide chains with an additional middle linker with a length of approximately 15 amino acid residues. Consequently, all molecules with a molecular weight corresponding to monomeric single-chain diabodies (50-60 kDa) are bispecific.

Diabodies can be fused to Fc to generate a more Ig-like molecules, named didiabody (Lu et al. 2004, J Biol Chem 279, 2856-2865). In addition, multivalent antibody constructs comprising two Fab repeats in the heavy chain of an IgG and capable of binding four antigen molecules has been described (see WO 0177342A1, and Miller et al. 2003, J Immunol 170, 4854-4861).

The term "antibody fragment" refers to any molecule comprising one or more fragments (usually one or more CDRs) of an antibody (the parent antibody) such that it binds to the same antigen to which the parent antibody binds. Antibody fragments include Fv, Fab, Fab', Fab'-SH, single-chain antibody molecules (such as scFv), F(ab')$_2$, single variable VH domains, and single variable VL domains (Holliger & Hudson 2005, Nature Biotechnol 23, 1126-1136). The term further includes microantibodies, i.e. the minimum recognition unit of a parent antibody usually comprising just one CDR (Heap et al. 2005, J Gen Virol 86, 1791-1800). Any of the fragments can be incorporated in a multivalent and/or multispecific larger molecule, e.g. mono- or bispecific Fab$_2$, mono- or tri-specific Fab$_3$, bis-scFv (mono- or bispecific), diabodies (mono- or bispecific), triabodies (e.g. trivalent monospecific), tetrabodies (e.g. tetravalent monospecific), minibodies and the like (Holliger & Hudson 2005, Nature Biotechnol 23, 1126-1136). Any of the fragments can further be incorporated in e.g. V-NAR domains of shark antibodies or VhH domains of camelid antibodies (nanobodies). All these are included in the term "antibody fragment".

The term "monoclonal antibody" refers to a population of substantially homogeneous antibodies. In contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the present invention may be made by the hybridoma method first described by Köhler & Milstein 1975, Nature 256, 495-497), or may be made by recombinant DNA methods (e.g. U.S. Pat. No. 4,816,567). Monoclonal antibodies may also be isolated from phage antibody libraries using the techniques described in, e.g., Clackson et al. 1991, Nature 352, 624-628 or Marks et al. 1991, J Mol Biol 222, 581-597, or by yet other techniques or technologies.

The term "chimeric antibody" refers to an antibody pieced together with portions derived from antibodies of the same species (e.g. antibodies of different classes) or different species, as well as fragments of such antibodies, as long as they exhibit the desired biological activity (e.g. U.S. Pat. No. 4,816,567; Morrison et al. 1984, Proc Natl Acad Sci USA 81, 6851-6855). For instance, "humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance.

Exemplary humanized versions of the antibodies of the invention may comprise at least one of:
  (i) a variable heavy chain as given in any one of SEQ ID NOs:18 to 21 carrying up to 16 mutations in the region outside the CDRs;
  (ii) a variable light chain as given in any one of SEQ ID NOs:14 to 17 carrying up to 9 mutations in the region outside the CDRs;
  (iii) a variable heavy chain as given in SEQ ID NO:18 carrying one or more of the following mutations: Val5Leu, Asp10Gly, Lys13Gln, Lys19Arg, Asp42Gly, Arg44Gly, Ser74Asn, Ser84Asn, Lys87Arg, Ser88Ala, Met93Val, and/or Thr114Leu;
  (iv) a variable heavy chain as given in SEQ ID NO:20 carrying one or more of the following mutations: Val5Leu, Asp10Gly, Lys13Gln, Lys19Arg, Asp42Gly, Arg44Gly, Phe80Tyr, Ser84Asn, Lys87Arg, Ser88Ala, Ile93Val, Val97Ala, and/or Thr114Leu;
  (v) a variable heavy chain as given in SEQ ID NO:21 carrying one or more of the following mutations: Val5Leu, Asp10Gly, Lys13Gln, Lys19Arg, Asp42Gly, Arg44Gly, Ser74Asn, Ser77Asn, Ser84Asn, Ser88Ala, Ile93Val, and/or Thr114Leu;
  (vi) a variable light chain as given in SEQ ID NO:15 carrying one or more of the following mutations:

Leu3Val, Thr7Ser, Ser14Thr, Asp17Gln, Gln18Pro, Lys50Arg, Leu88Val and/or Gly105Gln;
(vii) a variable light chain as given in SEQ ID NO:16 carrying one or more of the following mutations: Leu3Val, Thr7Ser, Ser14Thr, Asp17Gln, Gln18Pro, Ala45Pro, Lys50Arg, Leu88Val and/or Gly105Gln; or
(viii) a variable light chain as given in SEQ ID NO:17 carrying one or more of the following mutations: Leu3Val, Thr7Ser, Ser14Thr, Asp17Gln, Gln18Pro, Asn50Arg, Leu88Val and/or Gly105Gln.

Particular examples of humanized versions of an antibody of the invention comprise (i) a variable heavy chain defined by SEQ ID NO:102 and a variable light chain as defined by SEQ ID NO:103, or (ii) a variable heavy chain defined by SEQ ID NO:104 and a variable light chain as defined by SEQ ID NO:105, or (iii) a variable heavy chain defined by SEQ ID NO:106 and a variable light chain as defined by SEQ ID NO:107. Antigen-binding fragments of any of these humanized antibodies are also subject of the invention.

A "human antibody" is an antibody produced by a human and/or has been made using any of the techniques for making human antibodies. Human antibodies can be produced using various techniques known in the art such as by selection from a phage library expressing human antibodies (e.g., Vaughan et al. 1996, Nature Biotechnol 14, 309-314 (1996); Sheets et al. 1998, Proc Natl Acad Sci USA 95, 6157-6162; Hoogenboom & Winter 1991, J Mol Biol 227, 381-388; Marks et al. 1991, J Mol Biol 222, 581-597). Human antibodies can also be made by introducing human immunoglobulin loci into transgenic animals, e.g., mice in which the endogenous immunoglobulin genes have been partially or completely inactivated. Upon challenge, human antibody production is observed (e.g., U.S. Pat. No. 5,545,807; U.S. Pat. No. 5,545,806; U.S. Pat. No. 5,569,825; U.S. Pat. No. 5,625,126; U.S. Pat. No. 5,633,425; U.S. Pat. No. 5,661,016; Marks et al. 1992, BioTechnology 10, 779-783; Lonberg et al. 1994, Nature 368, 856-859; Morrison 1994, Nature 368, 812-813; Fishwild et al. 1996, Nature Biotechnol 14, 845-851; Lonberg & Huszar 1995, Internat Rev Immunol 13, 65-93). Alternatively, the human antibody may be prepared via immortalization of human lymphocytes producing an antibody directed against a target antigen wherein such lymphocytes may be recovered from an individual or may have been immunized in vitro (e.g., Cole et al. 1985, Monoclonal Antibodies and Cancer Therapy, Alan R. Liss, p. 77; Boerner et al. 1991, J Immunol 147, 86-95; U.S. Pat. No. 5,750,373).

The term "defined in/by SEQ ID NO:X" as used herein refers to a biological sequence consisting of the sequence of amino acids or nucleotides given in the SEQ ID NO:X. For instance, an antigen defined in/by SEQ ID NO:X consists of the amino acid sequence given in SEQ ID NO:X. A further example is an amino acid sequence comprising SEQ ID NO:X, which refers to an amino acid sequence longer than the amino acid sequence given in SEQ ID NO:X but entirely comprising the amino acid sequence given in SEQ ID NO:X (wherein the amino acid sequence given in SEQ ID NO:X can be located N-terminally or C-terminally in the longer amino acid sequence, or can be embedded in the longer amino acid sequence), or to an amino acid sequence consisting of the amino acid sequence given in SEQ ID NO:X.

The invention further comprises method for selecting antibodies with increased affinity to the antigen PDGF-C, said methods including the steps of (i) subjecting any of the above described antibodies to a process of affinity maturation and (ii) selecting an antibody with increased affinity to the antigen PDGF-C.

An "affinity matured antibody" is the result of an affinity maturation process applied to a parent antibody. An affinity matured antibody usually differs from its parent antibody in one or more amino acid positions, including in one or more CDR regions, said differences resulting in an improved affinity of the affinity matured antibody for an antigen compared to the affinity of the parent antibody for the same antigen. Affinity maturation processes include those as described by e.g. Marks et al. 1992, BioTechnology 10, 779-783 (affinity maturation by VH and VL domain shuffling). Random mutagenesis of CDR and/or framework residues is described by e.g. Barbas et al. 1994, Proc Natl Acad Sci USA 91, 3809-3813; Schier et al. 1996, Gene 169: 147-155; Yelton et al. 1995, J Immunol 155, 1994-2004; Jackson et al. 1995, J Immunol 154, 3310-3319; Hawkins et al. 1992, J Mol Biol 226, 889-896.

Derivatives of the antibodies of the invention, or of antigen-binding fragments of said antibodies, include, but are not limited to antibodies or fragments thereof labeled with an appropriate label, said label can for instance be of the enzymatic, colorimetric, chemiluminescent, fluorescent, or radioactive type. Derivatives of an antibody of the invention generally include all molecules resulting from conjugation of said antibody or fragment thereof with another compound. Such other compound may be, e.g., used to increase stability (e.g., half-life) and/or solubility of the antibody or antibody-fragment; may be an enzyme capable of converting a prodrug to its active form (e.g. for use in chemotherapy); or may itself have cytostatic and/or cytotoxic properties. Exemplary derivatizing modifications include pegylation, introduction (by insertion or mutation) of a non-naturally occurring cysteine in the antibody or antibody-fragment backbone (to create a cross-linking site), glycosylation (synthetic or via recombinant means) and the like. A further example of derivation relates to linking of a cytotoxic agent (a substance that inhibits or prevents the function of cells and/or causes destruction of cells) such as radioactive isotopes (e.g. $At^{211}$, $I^{131}$, $I^{125}$, $Y^{90}$, $Re^{186}$, $Re^{188}$, $sm^{153}$, $B^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof. Other derivatives of the antibodies of the invention include bispecific antibodies. Such antibodies are specific for the PDGF-C protein (as described above) on the one hand and specific for a second antigen on the other hand. The second antigen may, e.g., be any art-recognized tumor-specific antigen or tumor-associated antigen. Such PDGF-C- and tumor-antigen-bispecific antibodies may increase the efficiency of killing PDGF-C-expressing cells. Typically, the PDGF-C-specificity of bispecific antibodies would be obtained by including one or more of the light- or heavy-chain variable domains or one or more of CDRs of the light- and/or heavy-chain variable domains of the antibodies of the invention.

The invention further relates to isolated nucleic acids encoding any of the above-described PDGF-C-binding antibodies or antigen-binding fragments thereof. Anyone somewhat familiar with the genetic code will be capable of translating any protein sequence into a nucleotide sequence. Moreover, tools to perform such "reverse translation" or "backtranslation" are widely available such as http://www.bioinformatics.org/sms2/rev_trans.html or http://arbl.cvmbs.colostate.edu/molkit/rtranslate/index.html or http://www.entelechon.com/2008/10/backtranslation-tool/.

If required, adaptation of a nucleotide sequence to a given species, i.e. adaptation of the codon usage to optimize expression in a given species, nowadays also is common knowledge, and again freely accessible web-tools are available such as the codon usage database on http://www.kazusa.or.jp/codon/ or such as http://genomes.urv.es/OPTIMIZER/ (over 150 prokaryotic species).

Any of the above antibodies, antigen-binding fragments or nucleic acids encoding any of them is intended for use as a medicament. Such use can be a single use (monotherapy) or a use in combination with an additional therapeutic agent (combination therapy). To this end, at least one of the above antibodies, antigen-binding fragments or nucleic acids encoding any one of them may be formulated in a pharmaceutical composition which may further comprise a pharmaceutically acceptable carrier and, optionally, an additional therapeutic agent.

Any of the above antibodies, antigen-binding fragments or nucleic acids encoding any of them, in whatever form or formulation, may be made part of a kit. Typically such kit may contain another component or other components wherein not all of them need to be pharmaceutical compositions. A non-pharmaceutical component may e.g. be a leaflet containing information about the above antibodies, antigen-binding fragments or nucleic acids encoding any of them. A kit may also comprise the different active substances of a combination therapy (see further).

Said medicament is intended for example for prevention, inhibition or treatment of benign, pre-malignant or malignant tumors, ophthalmologic disorders, and disorders characterized by neo-vascularization.

"Cancer" refers to malignant neoplastic tumors and includes carcinomas (starting in the skin or in tissues that line or cover internal organs; includes skin-, lung-, colon-, pancreatic-, and ovarian cancers, and epithelial-, squamous- and basal cell carcinomas, melanomas, papillomas, and adenomas); sarcomas (starting in bone, cartilage, fat, muscle, blood vessels, or other connective or supportive tissue; includes bone- and soft tissue cancers, and osteosarcoma, synovialsarcoma, liposarcoma, angiosarcoma, rhabdosarcoma, and fibrosarcoma), leukemias (starting in blood-forming tissue such as the bone marrow and causes large numbers of abnormal blood cells to be produced and enter the blood; includes leukemia, lymphoblastic leukemias (ALL and CLL), myelogenous leukemias (AML and CML), T-cell leukemia, and hairy-cell leukemia), lymphomas and myelomas (starting in the cells of the immune system; including lymphoma, T-cell lymphomas, B-cell lymphomas, Hodgkin lymphomas, non-Hodgkin lymphoma, and lymphoproliferative lymphomas), central nervous system cancers (starting in the tissues of the brain and spinal cord; including brain and spinal cord tumors, gliomas, meningiomas, pituitary adenomas, vestibular schwannomas, primary CNS lymphomas, and primitive neuroectodermal tumors) and metastatic cancers (usually arising from a cell type listed above and now present in a tissue from which the cancer cells did not originally develop). A particular example of cancer is the triple-negative breast cancer which is not expressing the genes for estrogen receptor (ER), progesterone receptor (PR) or Her2/neu).

"Ophthalmologic disorders" include diabetic retinopathy (non-proliferative or proliferative), age-related macular edema, rubeosis iridis (growth of new abnormal blood vessels in the iris), choroidal neovascularization (CNV; growth of new blood vessels in the choroid layer of the eye), degenerative maculopathies, corneal neovascularization, neovascular glaucoma, retinopathy of prematurity, hyperplastic vitreous syndrome.

Disorders characterized by neo-vascularization, neo-angio genesis or pathologic angiogenesis (all used interchangeably) refers to disorders or diseases characterized by the formation of new blood vessels (capillary ingrowth and endothelial proliferation) in unusual sites, a finding typical of so-called "angiogenic diseases". An extensive list of disorders characterized by neo-vascularization is given in Table 1 of Carmeliet 2003 (Nature Medicine 9, 653-660) and includes, besides tumors and ophthalmologic disorders: infectious diseases, autoimmune disorders, vascular malformations, DiGeorge syndrome, HHT, cavernous hemangioma, atherosclerosis, transplant arteriopathy, obesity, psoriasis, warts, allergic dermatitis, scar keloids, pyogenic granulomas, blistering disease, pulmonary hypertension, asthma, nasal polyps, inflammatory bowel and periodontal disease, ascites, peritoneal adhesions, endometriosis, uterine bleeding, ovarian cysts, ovarian hyperstimulation, arthritis, synovitis, osteomyelitis, and osteophyte formation.

The term "combination therapy" as used herein refers to any type of combination. If technically feasible and clinically meaningful, two or more different active substances, one being an anti-PDGF-C antibody or fragment thereof or nucleic acid encoding any thereof according to the invention, can be combined in a single medicament or formulation. Alternatively, the two or more different active substances are provided as individual medicaments (wherein the medicament not comprising an anti-PDGF-C antibody or fragment thereof or nucleic acid encoding any thereof according to the invention can still be a combination of two or more other active substances) to be administered to the patient in a prescribed dosing regimen which can involve sequential and/or concurrent administration or administrations. It may well be that multiple administrations of the other active substance is required, one of which may be concurrent with the administration of the anti-PDGF-C antibody or fragment thereof or nucleic acid encoding any thereof according to the invention. This may especially be the case if the pharmacokinetics of said other active substance is totally different from the pharmacokinetics of the anti-PDGF-C antibody or fragment thereof or nucleic acid encoding any thereof according to the invention. Antibodies for instance indeed have the advantage of having favorable pharmacokinetics in the sense that they have a relatively long half-life. The sequential administration of two medicaments implies that the administration of the anti-PDGF-C antibody or fragment thereof or nucleic acid encoding any thereof according to the invention is preceded or followed by at least one administration of the other active substance or medicament. Clearly, any of the above also applies to cases where multiple administrations of the anti-PDGF-C antibody or fragment thereof or nucleic acid encoding any thereof according to the invention is required.

The additional active substance or agent can be any agent recognized in the art as useful in the prevention, inhibition or treatment of the intended disease or disorder. In general, the additional active substance or agent can for instance be a chemical agent (e.g. targeting enzymes or proteins, DNA or RNA, including synthetic aptamers, siRNAs, antisense RNAs and the like) or chemotherapeutic agent (e.g. general cytostatic or cytotoxic agent), a biological agent (e.g. antibodies or fragments thereof or protein scaffold-based molecules), an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. The additional active substance or agent may further be irradiation (e.g. in the treatment of some cancers) or laser therapy (e.g. in the treatment of some eye diseases).

Examples of anti-angiogenic agents include antibodies (or fragments thereof) such as anti-VEGF (vascular endothelial growth factor) or anti-PlGF (placental growth factor) antibodies and agents such as macugen (pegaptanib sodium), trypthophanyl-tRNA synthetase (TrpRS), anecortave acetate, combrestatin A4 prodrug, AdPEDF (adenovector capable of expressing pigment epithelium-derived factor), inhibitor of VEGF receptor-2, inhibitors of VEGF, PlGF or TGF-β, Sirolimus (rapamycin) and endostatin.

Examples of approved biological agents used in treatment of cancer or ophthalmologic disorders include bevacizumab (anti-VEGF), ranibizumab (anti-VEGF), aflibercept (or VEGF Trap-Eye), rituximab and ibritumomab tiuxetan (anti-CD20), trastuzumab (anti-Her2), gemtuzumab ozogamicin (anti-CD33), and alemtuzumab (anti-CD52).

Examples of chemotherapeutic agents useful in the treatment of cancer include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (e.g. bullatacin and bullatacinone); a camptothecin (including the synthetic analogue topotecan); bryostatin; callystatin; CC-1 065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^I$ and calicheamicin $\theta_1^I$ (e.g., Nicolaou et al. 1994, Angew Chem Intl Ed Engl 33, 183-186); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone, trilostane; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g. paclitaxel (TAXOL® Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; platinum analogs such as cisplatin and carboplatin; vinblastine; platinum; etoposide (VP-16); ifosfamide; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included are anti-hormonal agents that act to regulate or inhibit hormone action on tumors such as anti-estrogens including for example tamoxifen, raloxifene, aromatase inhibiting 4(5)imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Examples of anti-inflammatory agents include steroids (e.g. prednisolone, methylprednisolone, cortisone, hydrocortisone, prednisone, triamcinolone, dexamethasone) and non-steroidal anti-inflammatory agents (NSAIDs; e.g. acetaminophren, ibuprofen, aspirin).

Examples of antiviral agents include trifluridine, vidarabine, acyclovir, valacyclovir, famciclovir, and doxuridine.

Examples of antibacterial agents or antibiotics include ampicillin, penicillin, tetracycline, oxytetracycline, framycetin, gatifloxacin, gentamicin, tobramycin, bacitracin, neomycin and polymyxin.

Examples of anti-mycotic/fungistatic/antifungal agents include fluconazole, amphotericin, clotrimazole, econazole, itraconazole, miconazole, 5-fluorocytosine, ketoconazole and natamycin.

Examples of anti-mitotic agents include mitomycin C and 5-fluorouracyl.

Examples of antihistamines include ketitofen fumarate and pheniramine maleate.

Examples of anesthetics include benzocaine, butamben, dibucaine, lidocaine, oxybuprocaine, pramoxine, proparacaine, proxymetacaine, tetracaine and amethocaine.

For ophthalmological application or use, other adjunct agents or drugs can be used in conjunction with the anti-PDGF-C antibody or fragment thereof or nucleic acid encoding any thereof according to the invention including agents inducing mydriasis/pupillary dilation (e.g. scopoloamine, atropine or tropicamide, and/or cycloplegia (paralysis of the eye focusing muscle). Lubricants may in the ophthalmological setting also be required, such include propylene glycerol, glycerin, carboxymethylcellulose, hydroxypropylmethylcellulose, soy lecithin, polyvinyl alcohol, white petrolatum, mineral oil, povidone, carbopol 980, polysorbate 80, and dextran 70. Further, the anti-PDGF-C antibody or fragment thereof or nucleic acid encoding any thereof according to the invention can be used in combination with an agent capable of inducing posterior vitreous detachment (PVD) Inhibition of ocular neo-angiogenesis has indeed been shown to be more effective after inducing PVD (Lee and Koh 2011, Ophthalmology 118, 101-110). Agents capable of inducing PVD include plasmin and microplasmin (U.S. Pat. No. 5,304,118; WO2004/052228).

In case of treating or inhibiting neovascular glaucoma, an agent for controlling the intra-ocular pressure may also be used in conjunction with the anti-PDGF-C antibody or fragment thereof, or nucleic acid encoding any thereof according to the invention. Such medicaments include adrenergic blocking agents (beta blockers or sympatholytic drugs such as betaxolol, carteolol, levobunolol, metipanolol and timolol), adrenergic stimulating agents (sympathomimetic drugs such as aproclonidine, epinephrine, hydroxyamphetamine, phenylephrine, naphazoline and tetrahydrozaline), carbonic anhydrase inhibitors (such as systemic acetozolamide, and topical brinzolamide and dorzolamide), miotics (cholinergic stimulating agents, parasympathomimetic drugs such as carbachol and pilocarpine), osmotic agents (such as glycerin and mannitol), prostaglandin and prostaglandin analogues (prostamides, bimatoprost, unoprostone isopropyl, travoprost, latanoprost, natural prostaglandin, prostaglandin F2a, and FP prostanoid receptor agonists).

The anti-PDGF-C antibody or fragment thereof according to the invention, or the nucleic acid encoding any of these, can be used for the manufacture of a medicament. Therefore, the active substance may need to be formulated into a "pharmaceutically acceptable formulation". Such formulation in general is a composition comprising a carrier, diluent or adjunvant compatible with the one or more active ingredients to be formulated, the whole formulation being compatible with the intended use in the intended tissue or organ, etc. Examples of pharmaceutically acceptable formulations as well as methods for making them can be found, e.g., in Remington's Pharmaceutical Sciences (e.g. $20^{th}$ Edition; Lippincott, Williams & Wilkins, 2000) or in any Pharmacopeia handbook (e.g. US-, European- or International Pharmacopeia).

A "diluent, carrier or adjuvant", is any suitable excipient, diluent, carrier and/or adjuvant which, by itself, does not induce the production of antibodies harmful to the individual receiving the composition. Typically, pharmaceutically acceptable compounds (such as diluents, carriers and adjuvants) can be found in, e.g., a Pharmacopeia handbook (e.g. US-, European- or International Pharmacopeia).

A "diluent", or more in particular a "pharmaceutically acceptable diluent", includes diluents such as water, saline, physiological salt solutions, glycerol, ethanol, etc. Auxiliary substances such as wetting or emulsifying agents, pH buffering substances, preservatives may be included in such diluents.

A (pharmaceutically acceptable) carrier or adjuvant may enhance the response elicited by an antibody or fragment thereof according to the invention, e.g., by providing a continuous release of the antibody or fragment thereof according to the invention over a prolonged period of time (slow-release formulations). The term "adjuvant" usually refers to a pharmacological or immunological agent that modifies (preferably increases) the effect of other agents (e.g., drugs, vaccines) while having few if any direct effects when given by themselves. As one example of an adjuvant aluminium hydroxide (alum) is given, to which an active compound or ingredient of the invention can be adsorbed. Further, many other adjuvants are known in the art and can be used. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They may include any and all solvents, dispersion media, coatings, antibacterial and antifungal agents (for example sorbic acid or chlorobutanol), isotonic agents (such as sugars or sodium chloride) and the like, provided these are consistent with pharmaceutical practice, i.e. carriers and additives which do not create permanent damage to the subject receiving the carrier. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the active ingredients.

The medicament according to the invention may be prepared as an injectable, either as a liquid solution or suspension. Injection may be subcutaneous, intramuscular, intravenous, intra-arterial, intraperitoneal, intrathecal, intradermal, intraepidermal. In the case of local administration to the eye, intravitreal injection, injection into the anterior chamber or subconjunctival injection may be performed. The composition may also be prepared to make it suitable for other types of administration such as implantation, suppositories, oral ingestion, enteric application, inhalation, aerosolization, eye drops, nasal spray or drops, or administration through medical devices such as stents. Solid forms, suitable for dissolving in, or suspension in, liquid vehicles prior to injection may also be prepared. The preparation may also be emulsified or encapsulated in liposomes for enhancing its effect. The preparation may be administered to a subject as a bolus dose or by continuous infusion. The preparation may also be administered continuously, e.g., via an osmotic minipump.

For the purpose of treating, preventing or inhibiting an intended disease or disorder, and in method for treating, preventing or inhibiting an intended disease or disorder, an effective amount of the anti-PDGF-C antibody or fragment thereof according to the invention, or the nucleic acid encoding any of these, is administered to a subject in need thereof. An "effective amount" of an active substance in a composition is the amount of said substance required and sufficient to elicit an adequate response in preventing or treating or reducing the intended or targeted medical indication. It will be clear to the skilled artisan that such response may require successive (in time) administrations with the composition as part of an administration scheme or -schedule. The effective amount may vary depending on the health and physical condition of the individual to be treated, the age of the individual to be treated (e.g. dosing for infants may be lower than for adults) the taxonomic group of the individual to be treated (e.g. human, non-human primate, primate, etc.), the capacity of the individual's system to respond effectively, the degree of the desired response, the formulation of the active substance, the treating doctor's assessment and other relevant factors. The effective amount further may vary depending on whether it is used in monotherapy or in combination therapy. It is expected that the effective amount of the active substance of the invention (anti-PDGF-C antibody or fragment thereof or derivative thereof or nucleic acid encoding any thereof) will fall in a relatively broad range that can be determined through routine trials. Usually, the amount will vary from 0.01 to 1000 µg/dose, more particularly from 0.1 to 100 µg/dose. Alternatively, the active substance may be administered at a dose between 1 µg/kg body weight and 10 mg/kg body weight, or between 10 µg/kg body weight and 5 mg/kg body weight, or between 100 µg/kg body weight and 2 mg/kg body weight. Dosage treatment may be a single dose schedule or a multiple dose schedule. If the active substance is administered continuously, administered doses may be between 1 and 100 µg/kg/minute, between 1 and 50 µg/kg/minute, between 5 and 50 µg/kg/minute, or between 5 and 20 µg/kg/minute.

Preventive administration of (an effective amount of) the anti-PDGF-C antibody or fragment thereof according to the invention, or the nucleic acid encoding any of these, may be useful in e.g. the ophthalmological setting. Indeed, in case of an ophthalmological disease or disorder that responds to treatment with the anti-PDGF-C antibody or fragment thereof according to the invention, or the nucleic acid encoding any of these, a subject may suffer from such disease or disorder in a single eye. It is known in the art, however, that in such cases the companion other eye of the same subject is susceptible to develop the same disease or disorder. In such instances, the unaffected eye could be prophylactically treated with the anti-PDGF-C antibody or fragment thereof according to the invention, or the nucleic acid encoding any of these.

"Treatment" refers to any rate of reduction or retardation of the progress of the disease or disorder compared to the progress or expected progress of the disease or disorder when left untreated. More desirable, the treatment results in no/zero progress of the disease or disorder (i.e. "inhibition") or even in any rate of regression of the already developed disease or disorder.

The invention further relates to an antibody or fragment thereof, or derivative of any thereof, according to the invention for use as diagnostic tool. One exemplary diagnostic method in which the antibodies (or fragments or derivatives of any thereof) according to the invention can be used is the detection of PDGF-C protein in isolated cells (isolated such as by, e.g., biopsy) suspected to be tumor cells. The presence of PDGF-C in the isolated cells, especially if overexpressed, can subsequently be used as criterion for applying the anti-PDGF-C antibodies in a therapy for eradicating the tumor cells.

The isolated nucleic acids encoding the anti-PDGF-C antibody or fragment thereof according to the invention may be comprised in a recombinant vector, in particular an expression vector.

A further aspect of the invention relates to isolated cell lines or recombinant host cells expressing an anti-PDGF-C antibody or fragment thereof according to the invention. Said host cell can be any cell capable of expressing said antibody or fragment thereof. Suitable host cells include, but are not limited to, cultured mammalian (such as HEK293) or insect cells, cultured plant cells or transgenic plants, yeasts such a *Saccharomyces, Schizosaccharomyces, Pichia, Hansenula, Torulopsis*, and bacterial cells. Expression of the antibody of the invention or functionally equivalent fragment thereof may be transient or constitutive. In particular, the host cell is a hybridoma cell line such as the ones described above.

Another aspect of the invention covers hybridoma cell lines expressing an antibody of the invention, in particular the hybridoma cell lines with any of the biological deposit accession numbers LMBP 9483CB (anti-PDGF-C antibody 2D3), LMBP 9484CB (anti-PDGF-C antibody 5A2), LMBP 9485CB (anti-PDGF-C antibody 5H7), LMBP 9486CB (anti-PDGF-C antibody 16B1), or LMBP 9487CB (anti-PDGF-C antibody 29H1). These deposits were done under the conditions of the Budapest Treaty at the Belgian Coordinated Collections of Micro-organisms/Laboratory of Molecular Biology-Plasmid collection (BCCM/LMBP), Technologiepark 927, 9052 Gent (Zwijnaarde), Belgium on 15 Mar. 2012.

Methods of producing the above-described PDGF-C-binding antibodies, or antigen-binding fragments thereof, form an integral aspect of the invention. In particular, such methods can comprise the steps of:
 (i) obtaining a crude preparation of said antibody or antibody fragment by means of recombinant expression of said antibody or antibody fragment, or by means of chemical synthesis of said antibody or antibody fragment;
 (ii) purifying said antibody or antibody fragment from the crude preparation obtained in (i).

Alternatively, an antigen-binding fragment of the antibodies of the invention binding to PDGF-C can be obtained or produced by a method comprising the steps of:
 (i) obtaining a crude preparation of an antibody comprising said fragment by means of recombinant expression of said antibody or by means of chemical synthesis of the antibody;
 (ii) purifying said antibody from the crude preparation obtained in (i).
 (iii) isolating the antigen-binding fragment from the antibody purified in (ii).

EXAMPLES

The Examples included hereafter demonstrate the invention and are not construed to be limiting the scope of the invention in any way.

Example 1. Immunization with PDGF-C and Hybridoma Generation and Selection

Female, Balb/c mice were immunized with recombinant, human PDGF-C (2 subcutaneous injections of the antigen, 50 µg each, the first one in complete Freund's adjuvant, the second one in incomplete Freund's adjuvant).

Blood samples were collected from the tail of the mice, and the sera were tested for the presence of anti-human PDGF-C antibodies by ELISA. Briefly, 96-well ELISA plates were coated overnight with 1 µg/ml of human PDGF-C in PBS (100 µl/well, 4° C.). The plates were blocked with 1% BSA for 1 h at room temperature, the serum samples (100 µl/well) were added to the plates (at dilution ranging from 1/500 to 1/32000) and the antibodies were allowed to bind for 2 h at room temperature. Bound antibodies were detected with an HRP-labeled, goat antimurine IgG (Sigma, 100 μl/well, 1 h at room temperature) followed by reaction with OPD.

Nine months after the second subcutaneous injection, the mice received a third subcutaneous injection of 50 μg of the antigen in incomplete Freund's adjuvant, and 7 weeks after the third subcutaneous injection, the mice received a final i.p. injection of 50 μg of the antigen in saline buffer, and the fusion was performed. The mice were sacrificed and spleen cells were fused with SP2/0 myeloma cells according to the procedure of Galfré & Milstein (Methods Enzymol. 73, 3-46, 1981). After selection in HAT (hypoxanthine, aminopterine, thymidine) medium, positives clones were selected by screening the culture supernatants by ELISA as described above.

Positive clones were expanded, and the antibodies were purified by Protein A chromatography to allow further characterization.

Example 2. Cloning of cDNAs Encoding the $V_H$ and $V_L$ Chains of Murine Monoclonal Anti-PDGF-C Antibodies RNA was isolated from 5-10×10$^6$ hybridoma cells using the RNeasy Mini Kit from Qiagen (Venlo, The Netherlands) and cDNA was prepared using the QuantiTect Reverse Transcription Kit from Qiagen (Venlo, The Netherlands). PCR was performed with primers specific for the leader sequence and the constant region, respectively. Thus, the variable regions were contained in the PCR products but did not include the primer sequences. The primer combinations as given in Table 1 were used for each of the hybridomas 2D3, 5A2, 5H7, 16B1, 29H1.

TABLE 1

PCR primer combinations for amplifying light and heavy chain variable region encoding cDNAs

|  | Forward primer | Reverse primer |
|---|---|---|
| Light chain | ATGAAGTTGCCTGTTAGGC TGTTG (SEQ ID NO: 1) | GCTCACTGGATGGTGGGA AGATGG (SEQ ID NO: 2) |
| Heavy chain | ATGGAYTTYGGGCTGAKYT TKDTT (SEQ ID NO: 3) | CASAYMCAGGGGCCAGTG GATAGAC (SEQ ID NO: 4) |

D = A or G or T;
K = G or T;
M = A or C;
S = C or G;
Y = C or T

To amplify the $V_H$ and $V_L$ chains a touchdown PCR protocol was used with Accuprime Pfx Supermix (Life Technologies, Carlsbad, Calif.) in 25 μl reactions. After 30 seconds at 95° C., 3 cycles were run of 30 seconds 95° C., 30 seconds 64° C. and 1 minute at 68° C., followed by 3 cycles of 30 seconds 95° C., 30 seconds 61° C. and 1 minute at 68° C., 3 cycles of 30 seconds 95° C., 30 seconds 58° C. and 1 minute at 68° C., 3 cycles of 30 seconds 95° C., 30 seconds 55° C. and 1 minute at 68° C., 25 cycles of 30 seconds 95° C., 30 seconds 52° C. and 1 minute at 68° C., to finish with 5 minutes at 72° C.

The obtained PCR products were isolated from gel and inserted into pCR4Blunt-TOPO (Life Technologies, Carlsbad, Calif.) and sequenced with the M13 Forward (-20) primer (GTAAAACGACGGCCAG; SEQ ID NO:5) and the M13 reverse primer (CAGGAAACAGCTATGAC; SEQ ID NO:6) using the BigDye Terminator V3.1 Cycle Sequencing Kit (Life Technologies, San Diego, Calif.).

Heavy and light chain sequences from purified hybridoma 5H7 supernatant were sent to Eurosequence (Groningen, The Netherlands) for N-terminal sequencing. The light chain sequence was found to be: Asp-Val-Leu-Met-Thr-Gln-Thr-Pro-Leu-Ser-Leu (SEQ ID NO:7), whereas the heavy chain sequence was found to be: Glu-Val-Gln-Leu-Val-Glu-Ser-Gly-Gly-Asp-Leu (SEQ ID NO:8). These results are in correspondence with the nucleotide and amino acid sequences described hereafter for all 5 cloned antibodies.

Light Chain Variable Domains cDNA Sequences

Hybridomas 2D3 (IgG1, κ), 5A2 (IgG2b, κ), 29 H1 (IgG1, κ) and 16B1 (IgG1, κ)

(SEQ ID NO: 9)
gatgttttgatgacccaaactccactctccctgcctgtcagtcttggaga tcaagcctccatctcttgcagatctaatcagaScattgtacatagtaatg gagacacctatttagaatggtacctgcagaaaccaggccagtctccaaaK ctcctgatctacaaagtttccaaccgattttctggggtcccagacaggtt cagtggcagtggatcagggacagatttcacactcaagatcagcagagtgg aggctgaggatctgggagtttattactgctttcaaggttcacatgttcct cccacgttcggaggggggaccaagctggaaataaaa;

wherein the position S=c for 2D3 and g for 5A2, 16B1 and 29H1 and wherein the position K is g for 5A2 and 16B1, and t for 2D3 and 29H1.

Hybridoma 5H7 (IgG1, κ)

(SEQ ID NO: 10)
gatgttttgatgacccaaactccactctccctgcctgtcagtcttggaga tcaagcctccatctcttgcagatctagtcagaccattgtacatagtgatg gaaccacctatttagaatggtaccttcagaaagcaggccagtctccaaag ctcctgatctacaaagtttccaaccgattttctggggtcccagacaggtt cagtggcagtggatcagggacagatttcacactcaagatcagcagagtgg aggctgaggatctgggagtttattactgctttcaaggttcacatgttcct cccacgttcggaggggggaccaagctggaaataaaa Heavy Chain Variable Domains cDNA Sequences Hybridomas 2D3 (IgG1, κ) and 16B1 (IgG1, κ)

(SEQ ID NO: 11)
gaggtgcagctggtggaRtctgggggagacttagtgaagcctggagggtc cctgaaactctcctgtgcagcctctggattcactttcagtaactatggca tgtcttgggttcgccagactccagacaagaggctggagtgggtcgcaacc attggtagtggtggtagttacacctactatcoRgacagtgtgaaggggcg attcaccatctccagagacagtgccaagaacaccctgtacctgcaaatga gcagtctgaagtctgaggacacagccatgtattactgtgcaagacaggcc -continued cccctctgggactactctgactactggggccaaggcaccactctcactgt ctcctcg;

wherein the two positions R=g for 2D3 and a for 16B1
Hybridomas 5A2 (IgG2b, κ), 29 H1 (IgG1, κ)

(SEQ ID NO: 12)
gaggtgcagctggtggaatctgggggagacttagtgaagcctggagggtc cctgaaactctcctgtgcagcctctggattcactttcagtaactatggca tgtcttgggttcgccagactccagacaagaggctggagtgggtcgcaacc attggtagtggtggtcattacacctactatccagacagtgtgaaggggcg attcaccatctccagagacagtgccaagagcaccctgtacctgcaaatga gcagtctgaRgtctgaSgacacagccatatattactgtgcaagacaggcc cccctctgggactgctctgactactggggccaaggcaccactctcactgt ctcctcg;

wherein the position R=a for 5A2 and g for 29H1, and
wherein position S=g for 5A2 and c for 29H1
Hybridoma 5H7 (IgG1, κ)

(SEQ ID NO: 13)
gaggtgcagctggtggagtctgggggagacttagtgaagcctggagggtc cctgaaactctcctgtgcagcctctggattcactttcagtagctatggca tgtcttgggttcgccagactccagacaagaggctggagtgggtcgcaacc attggttatggtggtagtttcacctactatccagatagtatgaaggggcg cttcaccatctccagagacaatgccaagaacaccctgttcctgcaaatga gcagtctgaagtctgaggacacagccatatattactgtgtaagacaggcc cccctctgggactactttgactactggggccaaggcaccactctcacagt ctcctca Light Chain Variable Domains Amino Acid Sequences
Hybridoma 2D3 (IgG1, κ)

(SEQ ID NO: 14)
DVLMTQTPLSLPVSLGDQASISCRSNQTIVHSNGDTYLEWYLQKPGQSPN

LLIYKVSNRFSGVPDRFSGSGSGTDFTLKISRVEAEDLGVYYCFQGSHVP

PTFGGGTKLEIK

Hybridoma 5A2 (IgG2b, κ)=16 B1 (IgG1, κ)

(SEQ ID NO: 15)
DVLMTQTPLSLPVSLGDQASISCRSNQSIVHSNGDTYLEWYLQKPGQSPK

LLIYKVSNRFSGVPDRFSGSGSGTDFTLKISRVEAEDLGVYYCFQGSHVP

PTFGGGTKLEIK

Hybridoma 5H7 (IgG1, κ)

(SEQ ID NO: 16)
DVLMTQTPLSLPVSLGDQASISCRSSQTIVHSDGTTYLEWYLQKAGQSPK

LLIYKVSNRFSGVPDRFSGSGSGTDFTLKISRVEAEDLGVYYCFQGSHVP

PTFGGGTKLEIK

Hybridoma 29H1 (IgG1, κ)

(SEQ ID NO: 17)
DVLMTQTPLSLPVSLGDQASISCRSNQSIVHSNGDTYLEWYLQKPGQSPN

LLIYKVSNRFSGVPDRFSGSGSGTDFTLKISRVEAEDLGVYYCFQGSHVP

PTFGGGTKLEIK

Heavy Chain Variable Domains Amino Acid Sequences
Hybridoma 2D3 (IgG1, κ)=16B1 (IgG1, κ)

(SEQ ID NO: 18)
EVQLVESGGDLVKPGGSLKLSCAASGFTFSNYGMSWVRQTPDKRLEWVAT

IGSGGSYTYYPDSVKGRFTISRDSAKNTLYLQMSSLKSEDTAMYYCARQA

PLWDYSDYWGQGTTLTVSS

Hybridoma 5A2 (IgG2b, κ)

(SEQ ID NO: 19)
EVQLVESGGDLVKPGGSLKLSCAASGFTFSNYGMSWVRQTPDKRLEWVAT

IGSGGHYTYYPDSVKGRFTISRDSAKSTLYLQMSSLKSEDTAIYYCARQA

PLWDCSDYWGQGTTLTVSS

Hybridoma 5H7 (IgG1, κ)

(SEQ ID NO: 20)
EVQLVESGGDLVKPGGSLKLSCAASGFTFSSYGMSWVRQTPDKRLEWVAT

IGYGGSFTYYPDSMKGRFTISRDNAKNTLFLQMSSLKSEDTAIYYCVRQA

PLWDYFDYWGQGTTLTVSS

Hybridoma 29H1 (IgG1, κ)

(SEQ ID NO: 21)
EVQLVESGGDLVKPGGSLKLSCAASGFTFSNYGMSWVRQTPDKRLEWVAT

IGSGGHYTYYPDSVKGRFTISRDSAKSTLYLQMSSLRSDDTAIYYCARQA

PLWDCSDYWGQGTTLTVSS

Complementarity determining regions (CDRs) in the above-described monoclonal antibodies are depicted in Tables 2 and 3.

TABLE 2

| Light chain Complementarity determining regions (CDRs) | | | |
|---|---|---|---|
| Hybridoma | CDR1 | CDR2 | CDR3 |
| 5A2 | RSNQSIVH SNGDTYLE (SEQ ID NO: 22) | KVSNRFS (SEQ ID NO: 24) | FQGSHVPPT (SEQ ID NO: 25) |
| 29H1 | RSNQSIVH SNGDTYLE (SEQ ID NO: 22) | KVSNRFS (SEQ ID NO: 24) | FQGSHVPPT (SEQ ID NO: 25) |
| 2D3 | RSNQTIVH SNGDTYLE (SEQ ID NO: 38) | KVSNRFS (SEQ ID NO: 24) | FQGSHVPPT (SEQ ID NO: 25) |

TABLE 2-continued

Light chain Complementarity
determining regions (CDRs)

| Hybridoma | CDR1 | CDR2 | CDR3 |
|---|---|---|---|
| 16B1 | RSNQSIVH SNGDTYLE (SEQ ID NO: 22) | KVSNRFS (SEQ ID NO: 24) | FQGSHVPPT (SEQ ID NO: 25) |
| 5H7 | RSSQTIVH SDGTTYLE (SEQ ID NO: 23) | KVSNRFS (SEQ ID NO: 24) | FQGSHVPPT (SEQ ID NO: 25) |

Based on the similarity between CDR1 sequences of all 5 hybridomas (all further having identical light chain CDR2 and CDR3 sequences and identical or similar heavy chain CDR1, CDR2 and CDR3 sequences), a generalized CDR1 sequence RSXQXIVHSXGXTYLE (SEQ ID NO:26, with X at position 3 being Asn or Ser, X at position 5 being Ser or Thr, X at position 10 being Asp or Asn, and X at position 12 being Asp or Thr) can be designed.

TABLE 3

Heavy chain Complementarity
determining regions (CDRs)

| Hybridoma | CDR1 | CDR2 | CDR3 |
|---|---|---|---|
| 5A2 | NYGMS (SEQ ID NO: 27) | TIGSGGHYT YYPDSVKG (SEQ ID NO: 29) | QAPLWDCSDY (SEQ ID NO: 32) |
| 29H1 | NYGMS (SEQ ID NO: 27) | TIGSGGHYT YYPDSVKG (SEQ ID NO: 29) | QAPLWDCSDY (SEQ ID NO: 32) |
| 2D3 | NYGMS (SEQ ID NO: 27) | TIGSGGSYT YYPDSVKG (SEQ ID NO: 30) | QAPLWDYSDY (SEQ ID NO: 33) |
| 16B1 | NYGMS (SEQ ID NO: 27) | TIGSGGSYT YYPDSVKG (SEQ ID NO: 30) | QAPLWDYSDY (SEQ ID NO: 33) |
| 5H7 | SYGMS (SEQ ID NO: 28) | TIGYGGSFT YYPDSMKG (SEQ ID NO: 31) | QAPLWDYFDY (SEQ ID NO: 34) |

Based on the similarity between CDR1 sequences of all 5 hybridomas (all further having identical or similar heavy chain CDR2 and CDR3 sequences and identical or similar light chain CDR1, CDR2 and CDR3 sequences), a generalized CDR1 sequence XYGMS (SEQ ID NO:35, with X being Asn or Ser) can be designed.

Based on the similarity between CDR2 sequences of all 5 hybridomas (all further having identical or similar heavy chain CDR1 and CDR3 sequences and identical or similar light chain CDR1, CDR2 and CDR3 sequences), a generalized CDR2 sequence TIGXGGXXTYYPDSXKG (SEQ ID NO:36, with X at position 4 being Ser or Tyr, X at position 7 being Ser or His, X at position 8 being Phe or Tyr, and X at position 15 being Val or Met) can be designed.

Based on the similarity between CDR3 sequences of all 5 hybridomas (all further having identical or similar heavy chain CDR1 and CDR2 sequences and identical or similar light chain CDR1, CDR2 and CDR3 sequences), a generalized CDR3 sequence QAPLWDXXDY (SEQ ID NO:37, with X at position 7 being Cys or Tyr, and X at position 8 being Ser or Phe) can be designed.

The hybridoma cell lines expressing the above-described antibodies were deposited under the conditions of the Budapest Treaty at the Belgian Co-ordinated Collections of Micro-organisms/Laboratory of Molecular B iology-Plasmid collection (BCCM/LMBP), Technologiepark 927, 9052 Gent (Zwijnaarde), Belgium on 15 Mar. 2012 of the invention, under accession numbers LMBP 9483CB (anti-PDGF-C antibody 2D3), LMBP 9484CB (anti-PDGF-C antibody 5A2), LMBP 9485CB (anti-PDGF-C antibody 5H7), LMBP 9486CB (anti-PDGF-C antibody 16B1), and LMBP 9487CB (anti-PDGF-C antibody 29H1).

Example 3. Affinity of Anti-PDGF-C Antibodies for Binding to PDGF-C

The affinity of the 2D3, 5A2, 5H7, 16B1 & 29H1 antibodies was determined using Surface Plasmon Resonance.

The different antibodies were each separately coated to a CM5 chip at a density of 1680 RU using standard amine chemistry. Different concentrations (200, 175, 150, 125, 100, 75, 50, 25, 12.5, 6.25, 3.125 & 0 nM) of PDGF-C (R&D Systems, Cat. 1687-CC/CF) were injected over the coated antibody for 5 min, then buffer was flowed for 10 min to monitor the dissociation of the captured antigen. The surface was regeneration between each run with a single injection of glycine-HCl, pH 2.5. Affinities were obtained by analyzing the sensorgrams with the help of the BIAevaluation 4.1 software assuming a 1:1 interaction. The experiment was performed with a Biacore 3000 instrument. Affinity data are summarized in Table 4.

TABLE 4

Affinity (dissociation constant $K_D$) of 2D3, 5A2, 5H7, 16B1
& 29H1 antibodies measured by Surface Plasmon Resonance

| Antibody | $K_D$ (nM) |
|---|---|
| 2D3 | 1.5 |
| 5A2 | 5.0 |
| 5H7 | 2.5 |
| 16B1 | 1.2 |
| 29H1 | 1.5 |

Example 4. Inhibitory Activity of the Anti-Human PDGF-C Antibodies on PDGFRα Activation by Human PDGF-C Principle of the PDGFRα Assay To evaluate the inhibitory activity of anti-human PDGF-C antibodies on PDGFRα activation by human PDGF-C, the PathHunter® receptor tyrosine kinase assay for PDGFRα (93-0823C3) from DiscoveRx® was used. The assay is based on DiscoveRx® proprietary Enzyme Fragment Complementation (EFC) technology in which the β-galactoside (β-gal) enzyme has been split into two inactive fragments. A small complementing fragment of β-gal, the Prolink™ tag (PK) has been fused recombinantly to the intracellular C-terminus of the receptor tyrosine kinase PDGFRα. The larger portion of β-gal, termed EA for enzyme acceptor, is co-expressed with an SH2 (Src Homology 2) phosphotyrosine binding domain. Ligand-induced activation of the receptor results in dimerization and intracellular cross-phosphorylation of the receptor. Subsequently, the SH2 domain specifically binds the phosphorylated receptor resulting in the complementation of the two β-gal fragments PK and EA, and formation of a functional β-gal enzyme. Following addition of a β-gal substrate, an easily detectable chemiluminescent signal is produced which is directly correlated to receptor activation. The LumiLITE™ microplate reader is fully compatible with all EFC-based assays of DiscoveRx® and is therefore used.

The PathHuntery® PDGFRα Assay Method

For the PathHunter® PDGFRα, assay, U2OS PDGFRα, PLCG1 (phospholipase Cγ as the source of the SH2 domain) cells from DiscoveRx® were used. Frozen cells were stored in liquid nitrogen. Upon thawing, cells were resuspended in pre-warmed thawing medium (i.e. culture medium without the selection antibiotics Geneticin and Hygromycin B). After 48 hours of culture in a 5% $CO_2$ incubator at 37° C., thawing medium was replaced by culture medium (MEM Eagle 1× (30-2003 from Invitrogen), 10% fetal bovine serum (SH30071.03 from Perbio Science), 1× Penicillin-Streptomycin-Glutamine (10378-016 from Invitrogen), 250 µg/ml Hygromycin B (10687-010 from Invitrogen), 500 µg/ml Geneticin (10131-035 from Invitrogen)). Once confluence was reached, cells were passaged with a ⅓ dilution every 2-3 days using Accutase (L11-007 from PAA). Cells were maintained in a non-confluent state during routine culture.

In the PathHunter® PDGFRα, assay, the U2OS PDGFRα, PLCG1 cells from DiscoveRx® cultured up to 10 passages were used. Cells were seeded at 20.000 cells in 100 µl per well in 96-well white culture-treated microplates with clear bottom (3610 from Corning). The PathHunter® Cell Plating 16 Reagent (93-0563R16 from DiscoveRx®) was employed as seeding medium. Following 24 hours of culture in 5% $CO_2$ at 37° C., 25 µl of a 5-fold concentrated agonist solution in Cell Plating 16 Reagent was used per well to stimulate the cells. Recombinant human PDGF-C from R&D Systems (1687-CC/CF; Val235-Gly345) was applied as agonist. After 3 hours incubation at room temperature, 60 µl of PathHunter® detection reagent (93-0001 from DiscoveRx®; 1 part Galacton Star® Substrate, 5 parts Emerald II™ Solution, and 19 parts of PathHunter® Cell Assay Buffer) was added. Cells were placed at room temperature and in the dark for another hour before luminescence was measured with the LumiLITE™ microplate reader. With GraphPad Prism® software, a non-linear regression analysis was performed using the obtained luminescent values in order to generate a sigmoidal agonist dose-response curve with variable slope. The EC50 (i.e. half maximal effective concentration) and EC80 value (i.e. the effective concentration that leads to 80% of the maximal response) for human PDGF-C was calculated.

Inhibitory Activity of the Anti-Human PDGF-C Antibodies in the PathHunter® PDGFRα, Assay First, the agonist dose-response curve for human PDGF-C in the PathHunter® PDGFRα, assay was generated and the EC50 as well as the EC80 value were determined. Among different experiments, human PDGF-C was a very potent agonist with EC50 values in the low nanomolar range (5-20 nM). Consequently, EC80 values ranging from 20 to 50 nM were used during experiments with the anti-human PDGF-C antibodies.

To evaluate the inhibitory activity of anti-human PDGF-C antibodies on PDGFRα, activation by human PDGF-C, equal volumes of 6-fold concentrated solutions of anti-human PDGF-C antibodies and the EC80 of human PDGF-C, prepared in Cell Plating 16 Reagent, were mixed and the assay was performed as described above. As positive controls, an anti-human PDGF-C polyclonal goat IgG antibody (AF1560 from R&D Systems) and recombinant human PDGFRα, Fc chimera (6765-PR from R&D Systems) were employed. Mouse monoclonal IgG1 (anti-KLH antibody; ab34607 from Abcam) and IgG2b (anti-GST antibody; sc-57753 from Santa Cruz Biotechnology) antibodies were used as isotype controls. All conditions were tested in duplicate. Based on the measured luminescence, antagonist dose-response curves were obtained and IC50 values (i.e. half maximal inhibitory concentration) were calculated with the GraphPad Prism® software. The 5 anti-human PDGF-C antibodies 2D3, 5A2, 5H7, 16B1 and 29H1 were first tested at 4 different concentrations in the PathHunter® PDGFRα, assay: 50, 16.67, 5.56 and 1.85 µg/ml. At the highest concentrations, all antibodies were able to completely block the activation of PDGFRα by human PDGF-C (FIG. 1). They were more potent than the anti-human PDGF-C polyclonal goat IgG antibody (AF1560 from R&D Systems) and equally active as the recombinant human PDGFRα Fc chimera (6765-PR from R&D Systems) (FIGS. 2 and 3). The mouse monoclonal IgG1 and IgG2b isotype control antibodies did not show any inhibition of the PDGFRα activation by human PDGF-C (data not shown).

The 5 anti-human PDGF-C antibodies 2D3, 5A2, 5H7, 16B1 and 29H1 were also tested at different concentrations in the PathHunter® PDGFRα assay. A ten point series of 3-fold dilutions starting from 50 µg/ml down to 2.54 ng/ml was explored. Antagonist dose-response curves were generated and IC50 values were determined. The 5 anti-human PDGF-C antibodies have IC50 values in the low nanomolar range, and are therefore identified as very potent inhibitors of PDGFRα activation by human PDGF-C. Some of the commercially available anti-PDGF-C antibodies also inhibit activation of PDGFRα by PDGF-C.

TABLE 5

| Antagonist | Immunogen | IC50 value (nM) | IC50 value (nM) | IC50 value (nM) |
|---|---|---|---|---|
| mAb 2D3 | recombinant human PDGF-C | 7.47* | / | / |
| mAb 5A2 | recombinant human PDGF-C | 3.36* | / | / |
| mAb 5H7 | recombinant human PDGF-C | 5.57* | / | / |
| mAb 16B1 | recombinant human PDGF-C | 8.38* | / | / |
| mAb 29H1 | recombinant human PDGF-C | 3.45* | 0.87 | 0.24 |
| polyclonal Ab AF1560 | aa 230-345 human PDGF-C | 19.93 | 6.39 | 1.84 |
| polyclonal Ab AF1447 | aa 235-345 murine PDGF-C | / | 32.24 | nad |
| polyclonal Ab AP1722a | aa 80-110 human PDGF-C | / | nad | nad |
| polyclonal Ab sc-33190 | aa 126-250 human PDGF-C | / | nad | nad |
| monoclonal Ab sc-80290 | aa 230-345 murine PDGF-C | / | nad | nad |
| monoclonal Ab MAB1560 | aa 235-345 human PDGF-C | / | / | 0.54 |
| PDGFRα Fc | human PDGF-Rα (aa1-524)-IEGRMD-human $IgG_1$ (Pro100 - Lys330) | 0.65 | / | / |

*average value of 3 separate measurements; "nad": not able to determine; "/": not included in experiment.

IC50 values for the 5 anti-human PDGF-C antibodies, polyclonal goat IgG antibody (human PDGF-C immunogen spanning amino acids 230-345; AF1560 from R&D Systems), polyclonal goat IgG antibody (murine PDGF-C immunogen spanning amino acids 235-345; AF1447 from R&D Systems), polyclonal rabbit IgG antibody (human PDGF-C immunogen spanning amino acids 80-110;

AP1722a from ABGENT), polyclonal rabbit IgG antibody (human PDGF-C immunogen spanning amino acids 126-250; sc-33190 from Santa Cruz), monoclonal rat IgG antibody (murine PDGF-C immunogen spanning amino acids 230-345; sc-80290 from Santa Cruz), monoclonal mouse IgG antibody (human PDGF-C immunogen spanning amino acids 235-345; MAB1560 from R&D Systems), and the recombinant human PDGFRα Fc chimera (6765-PR from R&D Systems) in the PathHunter® PDGFRα assay.

From FIG. 1, it can be derived that antibodies 2D3, 5A2, 5H7, 16B1 and 29H1 at a concentration of 1.85 µg/mL only allow 49%, 30%, 32%, 38% and 23%, respectively, of PDGF-Rα activation by PDGF-C (wherein the 100% value was determined in the absence of any antibody). Other PDGF-C-binding monoclonal antibodies identified were incorporated in the same assay (and same experiment, thus allowing head-to-head comparison of all results) of which two were incorporated in assays described herein supra: mouse monoclonal antibodies 12E5 and 19F12. At a concentration of 1.85 µg/mL, these exert very little inhibition as nearly full activation, 82% and 80%, respectively, of PDGF-Rα by PDGF-C was measured.

Example 5. Anti-PDGF-C Antibodies Block Binding of PDGF-C to its Receptor PDGF-Rα

A competition ELISA was used to assess whether anti-PDGF-C antibodies exhibited inhibitory activity, i.e. whether they could block binding of PDGF-C to its receptor PDGF-Rα.

Recombinant human PDGF-Rα/Fc and human PDGF-C were purchased from R&D system. PDGF-C was biotinylated as follows: lyophilized PDGF-C was solubilized at 1 mg/ml in 4 mM HCl as recommended by the provider, and the solution was then neutralized by addition of 20 mM NaOH. Sulfo-NHS-LC-Biotin (EZ-Link Sulfo-NHS-LC-Biotin, Thermo Scientific) was added in a 15-fold molar excess over PDGF-C, and the mixture was kept on ice for 2 h. ELISA plates were coated with the receptor (1 µg/ml in PBS, 100 µl per well, overnight incubation at 4° C.). The wells were blocked for 1 h at room temperature with 200 µl of blocking buffer Immediately before use, the plates were washed 3 times with PBST (PBS supplemented with 0.004% tween-80). Biotinylated PDGF-C (0.1 µg/ml final concentration) was pre-incubated with the antibodies to be tested (at a 10-fold molar excess over PDGF-C) in PBSTA (PBST supplemented with 1% albumin), 100 µl of these samples were added to the relevant wells, and the plate was incubated for 2 hours at room temperature in a moist chamber. The wells were then washed 5 times with PBST. One hundred microliters of Streptavidin-HRP (R&D systems) diluted 1:200 in PBSTA was added to the wells, incubated for 20 min at room temperature, and the wells were then washed again 5 times with PBST. Detection of HRP activity was performed using 100 µl of the 1-Step Ultra TMB substrate (Thermo Scientific Pierce). After a 50-min incubation in the dark, the reaction was stopped by addition of 100 µl of 2 M H$_2$SO$_4$ and the plates were read at 450 nm. The signal obtained was compared with the one obtained in the absence of antibody. FIG. 4 illustrates that each of the five monoclonal anti-PDGF-C antibodies is capable of inhibiting binding of PDGF-C to its receptor PDGF-Rα.

Example 6. Determination of PDGF-C Epitopes Recognized by Anti-PDGF-C Antibodies The binding of anti-PDGF-C antibodies to 15-mer, overlapping peptides covering the entire human PDGF-C molecule was assessed by ELISA. Antibodies included in this analysis are the five antibodies potently inhibiting activation of PDGF-Rα by PDGF-C, i.e. monoclonal antibodies 2D3, 5A2, 5H7, 16B1 and 29H1. Further included are two antibodies capable of binding to PDGF-C, but not or very poorly inhibiting activation of PDGF-Rα by PDGF-C, i.e. monoclonal antibodies 12E5 (IgG1) and 19F12 (IgG2b) (see Example 4). Finally included are commercially available monoclonal antibodies sc-80290 (a rat monoclonal antibody raised against murine PDGF-C, the immunogen covering amino acid residues 230 to 345; Santa-Cruz) and MAB1560 (a mouse monoclonal antibody raised against human PDGF-C, the immunogen covering amino acid residues 235 to 345; R&D Systems) of which only MAB1560 shows inhibition of activation of PDGF-Rα by PDGF-C (see Example 4). For all antibodies, it was confirmed that they bind to human PDGF-C and binding to full-length human PDGF-C was for all antibodies tested more efficient than binding to any of the peptides identified as described hereafter.

The data are summarized in Table 6. The epitope of antibodies 2D3, 5A2, 5H7 and 29H1 was mapped to peptide no. 58, and the one of antibody 19F12 to peptide no. 49. Similarly, binding of the commercial antibody sc-80290 (Santa-Cruz) was observed for peptides nos 44, 49, 50 & 51. By contrast, the epitope of antibodies 16B1 and 12E5, as well as of the commercial antibody MAB1560 (R&D Systems) could not be identified with this approach, possibly because these antibodies recognize a conformational epitope. Significant binding of antibodies 5A2 and 19F12 was also detected against peptide nos 9 and 27. However, it should be emphasized here that these 2 peptides consistently gave a signal higher than the average background, and this irrespective of the antibody tested. A control experiment revealed that this is due to non-negligible binding of the secondary antibody (goat anti-mouse IgG-HRP) to the coated peptide (not shown). Incidentally, such binding was also observed, although to a lower extent, for peptide nos 49, 50 and 51 with the goat anti-rat IgG-HRP secondary antibody used to detect binding of the sc-80290 antibody. It is therefore possible that the epitope of the latter antibody is limited to peptide no 44.

Monoclonal antibody 19F12 and the commercially available monoclonal antibody sc-80290 are poor inhibitors or are not inhibitors of PDGF-Rα activation by PDGF-C (see Example 4) but nevertheless bind to the growth factor domain of PDGF-C (amino acids 235-345 of human PDGF-C), more particularly to peptide no. 49 (19F12) and to peptide no. 44 and perhaps to peptide nos. 49-51 (sc-80290). On the other hand, monoclonal antibodies 2D3, 5A2, 5H7 and 29H1 apparently bind to the same epitope, i.e. peptide no. 58, of the growth factor domain of human PDGF-C and do strongly inhibit PDGF-Rα activation by PDGF-C. Finally, the binding site of monoclonal antibody 16B1 on PDGF-C is fully unclear (as whereas commercially available monoclonal antibody MAB1560 must, based on the available information about the immunogen used, bind to the growth factor domain of PDGF-C although it is not clear where. Altogether, these data indicate that not just any antibody binding to PDGF-C, or to the growth factor domain of PDGF-C is capable of inhibiting PDGF-Rα activation by PDGF-C.

Table 6.

The indicated peptides where synthesized in an N-terminally biotinylated form and coated onto a neutravidin plate (Thermo Scientific, Cat. 15127) at a concentration of 10 µg/mL. The antibodies listed in the table were incubated in each well at a concentration of 1 µg/mL and, following washing, were then detected in a standard ELISA format using an appropriate, HRP-labeled secondary antibody (goat anti-mouse IgG-HRP for all antibodies except sc-80290, and goat anti-rat IgG-HRP for sc-80290). Each antibody was tested at least twice, and up to 4 times. A "+" in the table indicate that a signal to background >3 was found and confirmed at least once. The background signal was measured in the absence of peptide using both the primary and the secondary antibodies. Antibodies sc-80290 and MAB1560 were tested only against peptides 42-63 since this represents the fraction of the protein that was used as an immunogen.

| Peptide | | | Antibody | | | | | | | | |
|---|---|---|---|---|---|---|---|---|---|---|---|
| No | SEQ ID NO: | Sequence | 2D3 | 5A2 | 5H7 | 16B1 | 29H1 | 12E5 | 19F12 | sc-80290 | MAB1560 |
| 1 | 39 | ESNLSSKFQFSSNKE | − | − | − | − | − | − | − | N.D. | N.D. |
| 2 | 40 | SKFQFSSNKEQNGVQ | − | − | − | − | − | − | − | N.D. | N.D. |
| 3 | 41 | SSNKEQNGVQDPQHE | − | − | − | − | − | − | − | N.D. | N.D. |
| 4 | 42 | QNGVQDPQHERIITV | − | − | − | − | − | − | − | N.D. | N.D. |
| 5 | 43 | DPQHERIITVSTNGS | − | − | − | − | − | − | − | N.D. | N.D. |
| 6 | 44 | RIITVSTNGSIHSPR | − | − | − | − | − | − | − | N.D. | N.D. |
| 7 | 45 | STNGSIHSPRFPHTY | − | − | − | − | − | − | − | N.D. | N.D. |
| 8 | 46 | IHSPRFPHTYPRNTV | − | − | − | − | − | − | − | N.D. | N.D. |
| 9 | 47 | FPHTYPRNTVLVWRL | − | + | − | − | − | − | + | N.D. | N.D. |
| 10 | 48 | PRNTVLVWRLVAVEE | − | − | − | − | − | − | − | N.D. | N.D. |
| 11 | 49 | LVWRLVAVEENVWIQ | − | − | − | − | − | − | − | N.D. | N.D. |
| 12 | 50 | VAVEENVWIQLTFDE | − | − | − | − | − | − | − | N.D. | N.D. |
| 13 | 51 | NVWIQLTFDERFGLE | − | − | − | − | − | − | − | N.D. | N.D. |
| 14 | 52 | LTFDERFGLEDPEDD | − | − | − | − | − | − | − | N.D. | N.D. |
| 15 | 53 | RFGLEDPEDDICKYD | − | − | − | − | − | − | − | N.D. | N.D. |
| 16 | 54 | DPEDDICKYDFVEVE | − | − | − | − | − | − | − | N.D. | N.D. |
| 17 | 55 | ICKYDFVEVEEPSDG | − | − | − | − | − | − | − | N.D. | N.D. |
| 18 | 56 | FVEVEEPSDGTILGR | − | − | − | − | − | − | − | N.D. | N.D. |
| 19 | 57 | EPSDGTILGRWCGSG | − | − | − | − | − | − | − | N.D. | N.D. |
| 20 | 58 | TILGRWCGSGTVPGK | − | − | − | − | − | − | − | N.D. | N.D. |
| 21 | 59 | WCGSGTVPGKQISKG | − | − | − | − | − | − | − | N.D. | N.D. |
| 22 | 60 | TVPGKQISKGNQIRI | − | − | − | − | − | − | − | N.D. | N.D. |
| 23 | 61 | QISKGNQIRIRFVSD | − | − | − | − | − | − | − | N.D. | N.D. |
| 24 | 62 | NQIRIRFVSDEYFPS | − | − | − | − | − | − | − | N.D. | N.D. |
| 25 | 63 | RFVSDEYFPSEPGFC | − | − | − | − | − | − | − | N.D. | N.D. |
| 26 | 64 | EYFPSEPGFCIHYNI | − | − | − | − | − | − | − | N.D. | N.D. |
| 27 | 65 | EPGFCIHYNIVMPQF | − | + | − | − | − | − | + | N.D. | N.D. |
| 28 | 66 | IHYNIVMPQFTEAVS | − | − | − | − | − | − | − | N.D. | N.D. |
| 29 | 67 | VMPQFTEAVSPSVLP | − | − | − | − | − | − | − | N.D. | N.D. |
| 30 | 68 | TEAVSPSVLPPSALP | − | − | − | − | − | − | − | N.D. | N.D. |
| 31 | 69 | PSVLPPSALPLDLLN | − | − | − | − | − | − | − | N.D. | N.D. |
| 32 | 70 | PSALPLDLLNNAITA | − | − | − | − | − | − | − | N.D. | N.D. |
| 33 | 71 | LDLLNNAITAFSTLE | − | − | − | − | − | − | − | N.D. | N.D. |

-continued

| No | SEQ ID NO: | Peptide Sequence | Antibody | | | | | | | | |
|----|------------|------------------|------|------|------|------|------|------|------|--------------|---------|
|    |            |                  | 2D3 | 5A2 | 5H7 | 16B1 | 29H1 | 12E5 | 19F12 | sc-80290 | MAB1560 |
| 34 | 72 | NAITAFSTLEDLIRY | − | − | − | − | − | − | − | N.D. | N.D. |
| 35 | 73 | FSTLEDLIRYLEPER | − | − | − | − | − | − | − | N.D. | N.D. |
| 36 | 74 | DLIRYLEPERWQLDL | − | − | − | − | − | − | − | N.D. | N.D. |
| 37 | 75 | LEPERWQLDLEDLYR | − | − | − | − | − | − | − | N.D. | N.D. |
| 38 | 76 | WQLDLEDLYRPTWQL | − | − | − | − | − | − | − | N.D. | N.D. |
| 39 | 77 | EDLYRPTWQLLGKAF | − | − | − | − | − | − | − | N.D. | N.D. |
| 40 | 78 | PTWQLLGKAFVFGRK | − | − | − | − | − | − | − | N.D. | N.D. |
| 41 | 79 | LGKAFVFGRKSRVVD | − | − | − | − | − | − | − | N.D. | N.D. |
| 42 | 80 | VFGRKSRVVDLNLLT | − | − | − | − | − | − | − | − | − |
| 43 | 81 | SRVVDLNLLTEEVRL | − | − | − | − | − | − | − | − | − |
| 44 | 82 | LNLLTEEVRLYSCTP | − | − | − | − | − | − | − | + | − |
| 45 | 83 | EEVRLYSCTPRNFSV | − | − | − | − | − | − | − | − | − |
| 46 | 84 | YSCTPRNFSVSIREE | − | − | − | − | − | − | − | − | − |
| 47 | 85 | RNFSVSIREELKRTD | − | − | − | − | − | − | − | − | − |
| 48 | 86 | SIREELKRTDTIFWP | − | − | − | − | − | − | − | − | − |
| 49 | 87 | LKRTDTIFWPGCLLV | − | − | − | − | − | − | + | + | − |
| 50 | 88 | TIFWPGCLLVKRCGG | − | − | − | − | − | − | − | + | − |
| 51 | 89 | GCLLVKRCGGNCACC | − | − | − | − | − | − | − | + | − |
| 52 | 90 | KRCGGNCACCLHNCN | − | − | − | − | − | − | − | − | − |
| 53 | 91 | NCACCLHNCNECQCV | − | − | − | − | − | − | − | − | − |
| 54 | 92 | LHNCNECQCVPSKVT | − | − | − | − | − | − | − | − | − |
| 55 | 93 | ECQCVPSKVTKKYHE | − | − | − | − | − | − | − | − | − |
| 56 | 94 | PSKVTKKYHEVLQLR | − | − | − | − | − | − | − | − | − |
| 57 | 95 | KKYHEVLQLRPKTGV | − | − | − | − | − | − | − | − | − |
| 58 | 96 | VLQLRPKTGVRGLHK | + | + | + | − | + | − | − | − | − |
| 59 | 97 | PKTGVRGLHKSLTDV | − | − | − | − | − | − | − | − | − |
| 60 | 98 | RGLHKSLTDVALEHH | − | − | − | − | − | − | − | − | − |
| 61 | 99 | SLTDVALEHHEECDC | − | − | − | − | − | − | − | − | − |
| 62 | 100 | ALEHHEECDCVCRGS | − | − | − | − | − | − | − | − | − |
| 63 | 101 | EECDCVCRGSTGG | − | − | − | − | − | − | − | − | − |

Example 7. Anti-Tumor Activity of Anti-PDGF-C Antibodies

The anti-tumor activity of an anti-PDGF-C antibody is evaluated at two dose-levels (such as at 4 and 10 mg/kg) against human xenograft glioblastoma, ovary, lung, or colon cancers implanted subcutaneously in female BALB/c nude or SCID mice (n=10 mice per group, treated and control). Treatment starts when tumor size reaches a volume of 150 mm³. The anti-PDGF-C antibody is administered intraperitoneally, twice weekly, until the tumors reach a volume of 1000 mm³ in the control group. The control group is treated with PBS alone.

Antitumor Effect of Anti-PDGF-C Antibodies Against a Glioblastoma Tumor, U118 Implanted in Female SCID Beige Mice For the evaluation of anti-tumor activity of the antibodies, animals were weighed and tumors measured 2 times weekly using a caliper. Tumor weights were calculated using the formula mass (mg)=[length (mm)×width (mm)²]/2. Antitumor activity evaluation was done at the single dose of 20 mg/kg. A dosage producing a 20% body weight loss (bwl) or 10% or more drug deaths, was considered an excessively toxic dosage. Animal body weights included the tumor weights. The primary efficacy end point is the tumor growth inhibition (% TGI). Changes in tumor volume for each treated (T) and control (C) are calculated for each tumor by subtracting the tumor volume on the day of first treatment (staging day) from the tumor volume on the specified observation day. The median ΔT is calculated for the treated group and the median ΔC is calculated for the control group. Then the ratio ΔT/ΔC is calculated and expressed as a percentage of TGI:

$$\Delta T = Tt - T0$$

$$\Delta C = Ct - C0$$

$$\% \ TGI = [1 - (\text{median}(Tt-T0)/\text{median}(Ct-C0)]*100$$

The antitumor effect of 29H1, 5A2 and 16B1 was evaluated against a measurable glioblastoma tumor, U118, which express both PDGF-C and its receptor, PDGFRa, S.C. implanted in female SCID Beige mice. Control group was treated with PBS alone. The antibodies were administered by an intraperitoneal (IP) injection, and treatment started on day 28 post-tumor implantation and was performed twice a week. Treatment with 29H1 and 5A2 was well-tolerated with no tumor body weight loss, and showed anti-tumor activity against the glioblastoma, U118, with higher inhibition being observed for 29H1 (TGI=53.0%) and 5A2 (TGI=58.5%) on day 56. The ip administration of 16B1 failed to block tumor growth at the different time points evaluated.

TABLE 7

In vivo inhibitory effect on glioblastoma tumor growth exerted by monoclonal anti-PDGF-C antibodies.

| Antibody Clones | Days post-tumor implantation TGI (%) | | | | |
|---|---|---|---|---|---|
| | Day 53 | Day 56 | Day 60 | Day 63 | Day 67 |
| 29H1 | 39.4 | 53.0 | 53.8 | 42.8 | 50.0 |
| 5A2 | 55.7 | 58.5 | 38.5 | 43.4 | 42.0 |
| 16B1 | 8.25 | 20.0 | 27.6 | 11.5 | 11.9 |

Example 8. Anti-Tumor Activity of Anti-PDGF-C Antibodies in Combination with Another Anti-Cancer Drug The efficacy of a combination therapy may be established by determination of therapeutic synergy. A combination of two drugs (one of which being at least one of the anti-PDGF-C antibodies of the invention) shows therapeutic synergy if it is therapeutically superior to each of the constituents used alone at its maximum tolerated dose (MTD). To demonstrate the efficacy of a combination, it may be necessary to compare the maximum tolerated dose of the combination with the maximum tolerated dose of each of the separate constituents in the study in question.

This efficacy may be quantified by determining the % TGI (tumor growth inhibition), which is calculated by dividing the tumor volumes (and/or tumor weights, see Example 6) from treated groups by the control groups and multiplied by 100. Toxicity is declared at dosages inducing >15% body weight loss or >10% deaths caused by the drug. Another criteria to be used is the response rate: Partial Regressions (PR) correspond to regression >50% initial tumor burden, and Complete Regressions (CR) to regression below the limit of palpation. Data is analyzed using statistical tools known to the person skilled in the art.

The efficacy in inhibiting tumor growth of a combination of at least one of the anti-PDGF-C antibodies of the invention with chemotherapy may be determined experimentally in the following manner Immunodeficient animals are subcutaneously grafted with glioblastoma, ovary, lung, or colon cancer cell lines. Treatment starts when tumor size reaches a volume of 150 mm$^3$. The anti-PDGF-C antibody is administered intraperitoneally, twice weekly at 3-5 dose-levels, until the tumors reach a volume of 1000 mm3 in the control group. Chemotherapy with doxorubicin, cisplatin or taxanes, at 3-dose-levels, starts simultaneously with the anti-PDGF-C antibody using their best treatment schedules previously determined in a pilot study. The different animal groups are weighed 3 or 4 times a week until the maximum weight loss is reached, and the groups are then weighed at least once a week until the end of the trial. The tumors are measured 2 or 3 times a week until the tumor reaches approximately 2 g, or until the animal dies if this occurs before the tumor reaches 2 g. The animals are autopsied when sacrificed.

The results obtained with treatment of chemotherapy and anti-PDGF-C antibody alone, and the combinations being used at their optimum dose are analyzed using statistical tools known to the person skilled in the art.

Example 9. Humanization of Murine Anti-PDGF-C Antibodies

When injected in humans, mouse antibodies can induce a human anti-mouse antibody response, which could hamper the therapeutic efficacy. To limit this response, the mouse antibodies are made to look more like endogenous human sequences in a process called humanization. Mouse and human antibody sequences are compared, and where appropriate, mouse amino acid residues are substituted by human amino acid residues. Substitutions that have a negative effect on properties such as affinity and stability are avoided, and humanized variants of the mouse antibody are evaluated for conservation of affinity.

In a first step, the structures of the mouse antibodies 2D3, 5A2, 5H7, 16B1 and 29H1 were modelled using the program MOE (Chemical Computing Group Inc, Canada). An antibody template sequence was selected from the PDB (Protein Data Bank, www.rcsb.org/) based on a high degree of homology with the target antibody sequence. During this phase there is no restriction on the origin of the templates, since the sequences with the highest homology are chosen. This was done for the heavy and light chain variable region sequences individually, and a template was selected with good homology to both the heavy and light chain variable region sequences. Since the sequences are highly homologous, the basic template is the same for all, 1IGF. Side chains were kept as in the template if they were identical. If different a Dead-End elimination method was applied to position the side-chains in the energetically best orientation.

For modelling the CDRs (which in MOE are a mixture of the Kabat and the Chotia determination of the CDR regions), a CDR loop could be taken from the same template or from different antibodies from the PDB. The following criteria were used to choose for the best CDR loop: (i) Best (=lowest) B-factor for the residues in the CDR; (ii) geometry of the CDR versus the rest of the template structure; (iii) best R over Rfree value for the CDRs. To get to the final model, all residues were changed to the required mouse sequence and energy optimized. The secondary structure was calculated and solvent exposed VH and VL residues were identified by calculating the relative accessibility of all side-chains.

In a next step, to compare the mouse with human sequences, human monoclonal sequences with a high homology with the target sequences were searched with a blastp search in the database of human proteins (http://blast.ncbi.nlm.nih.gov/). Some of the sequences were omitted since these are antibodies bound to a human protein, but the antibody probably was not human; or the antibody was already a humanized mouse antibody.

Side-chains that were different between the mouse and the human sequence, were 5 Å or more away from the CDRs, and had a relative accessibility >25% were considered for humanization. By visual inspection on a graphical stereo equipped screen all these residues were checked for mutation to the human variant. Residues not disturbing the overall three dimensional conformation were considered for change into the human counterpart residue.

Thus, as listed in the table below, up to 16 residues in the heavy chain variable regions and up to 9 residues in the light chain variable regions were identified that could be mutated to their counterparts present in the most similar human antibodies.

TABLE 8

| Residue number | Mouse 2D3 | Mouse 5A2 | Mouse 5H7 | Mouse 16B1 | Mouse 29H1 | Human variant |
|---|---|---|---|---|---|---|
| 8.1.Variable region heavy chain ||||||||
| H5 | VAL | VAL | VAL | VAL | VAL | LEU |
| H10 | ASP | ASP | ASP | ASP | ASP | GLY |
| H13 | LYS | LYS | LYS | LYS | LYS | GLN |
| H19 | LYS | LYS | LYS | LYS | LYS | ARG |
| H42 | ASP | ASP | ASP | ASP | ASP | GLY |
| H44 | ARG | ARG | ARG | ARG | ARG | GLY |
| H74 | SER | SER | ASN | SER | SER | ASN |
| H77 | ASN | ASN | ASN | ASN | SER | ASN |
| H80 | TYR | TYR | PHE | TYR | TYR | TYR |
| H84 | SER | SER | SER | SER | SER | ASN |
| H87 | LYS | LYS | LYS | LYS | ARG | ARG |
| H88 | SER | SER | SER | SER | SER | ALA |
| H89 | GLU | GLU | GLU | GLU | ASP | GLU |
| H93 | MET | ILE | ILE | MET | ILE | VAL |
| H97 | ALA | ALA | VAL | ALA | ALA | ALA |
| H114 | THR | THR | THR | THR | THR | LEU |
| 8.2.Variable region light chain ||||||||
| L3 | LEU | LEU | LEU | LEU | LEU | VAL |
| L7 | THR | THR | THR | THR | THR | SER |
| L14 | SER | SER | SER | SER | SER | THR |
| L17 | ASP | ASP | ASP | ASP | ASP | GLN |
| L18 | GLN | GLN | GLN | GLN | GLN | PRO |
| L45 | PRO | PRO | ALA | PRO | PRO | PRO |
| L50 | LYS | LYS | LYS | LYS | ASN | ARG |
| L88 | LEU | LEU | LEU | LEU | LEU | VAL |
| L105 | GLY | GLY | GLY | GLY | GLY | GLN |

Residues of the murine monoclonal anti-PDGF-C antibodies considered for humanization. Numbering of the residues corresponds to sequences given in Example 2 (e.g., "H5" of 2D3 is amino acid 5 of the heavy chain sequence of 2D3 in Example 2, i.e., the fifth amino acid in SEQ ID NO:18).

Based on Table 8, the following humanized antibodies (amino acid sequences and nucleic acid sequences listed) were produced and serve as exemplary humanized antibodies.

Humanized 5H7 Anti-PDGF-C Antibody
Heavy Chain Variable Region (SEQ ID NO: 102)
EVQLLESGGGLVQPGGSLRLSCAASGFTFSSYGMSWVRQTPGKG

LEWVATIGYGGSFTYYPDSMKGRFTISRDNAKNTLYLQMNSLRA

EDTAVYYCARQAPLWDYFDYWGQGTLLTVSS

Light Chain Variable Region (SEQ ID NO: 103)
DVVMTQSPLSLPVTLGQPASISCRSSQTIVHSDGTTYLEWYLQK

PGQSPRLLIYKVSNRFSGVPDRFSGSGSGTDFTLKISRVEAEDV

GVYYCFQGSHVPPTFGQGTKLEIK

Humanized 16B1 Anti-PDGF-C Antibody
Heavy Chain Variable Region (SEQ ID NO: 104)
EVQLLESGGGLVQPGGSLRLSCAASGFTFSNYGMSWVRQTPGKG

LEWVATIGSGGSYTYYPDSVKGRFTISRDNAKNTLYLQMNSLRA

EDTAVYYCARQAPLWDYSDYWGQGTLLTVSS light Chain Variable Region (SEQ ID NO: 105)
DVVMTQSPLSLPVTLGQPASISCRSNQSIVHSNGDTYLEWYLQK

PGQSPRLLIYKVSNRFSGVPDRFSGSGSGTDFTLKISRVEAEDV

GVYYCFQGSHVPPTFGQGTKLEIK

Humanized 29H1 Anti-PDGF-C Antibody
Heavy Chain Variable Region (SEQ ID NO: 106)
EVQLLESGGGLVQPGGSLRLSCAASGFTFSNYGMSWVRQTPGKG

LEWVATIGSGGHYTYYPDSVKGRFTISRDNAKNTLYLQMNSLRA

EDTAVYYCARQAPLWDCSDYWGQGTLLTVSS

Light Chain Variable Region (SEQ ID NO: 107)
DVVMTQSPLSLPVTLGQPASISCRSSQTIVHSDGTTYLEWYLQK

PGQSPRLLIYKVSNRFSGVPDRFSGSGSGTDFTLKISRVEAEDV

GVYYCFQGSHVPPTFGQGTKLEIK

DNA Sequences of the Humanized Antibodies:
Humanized 5H7 Anti-PDGF-C Antibody
Heavy Chain Variable Region (SEQ ID NO: 108)
GAGGTGCAGCTTCTGGAATCTGGGGGAGGTCTTGTGCAGCCAGG

AGGGTCCCTGCGGCTCTCCTGTGCCGCATCTGGATTCACTTTCA

GTAGCTATGGCATGTCTTGGGTTCGCCAGACTCCTGGCAAGGG

CTGGAGTGGGTCGCAACCATTGGCTATGGTGGGAGTTTCACCTA

-continued
CTATCCAGATTCAATGAAGGGACGCTTTACCATCAGCAGAGACA

ATGCCAAGAACACCTTGTACCTGCAAATGAACAGTCTGCGAGCC

GAAGACACAGCCGTGTACTATTGCGCTAGGCAGGCTCCCCTCTG

GGACTACTTTGATTACTGGGGCCAAGGCACATTGCTCACAGTCT

CCTCA

Light Chain Variable Region (SEQ ID NO: 109)
GACGTTGTGATGACCCAATCTCCCTTGTCCCTGCCTGTCACTCT

TGGGCAGCCTGCCTCCATTAGCTGTCGCTCTAGCCAGACCATTG

TGCATAGTGACGGCACAACCTACCTGGAATGGTATCTTCAGAAA

CCAGGCCAGAGCCCACGGCTCCTGATCTACAAAGTTTCCAACAG

GTTTAGTGGGGTCCCAGACAGGTTCTCCGGCAGTGGATCAGGGA

CAGATTTCACACTCAAGATAAGCAGAGTGGAGGCTGAGGATGTG

GGAGTCTACTATTGCTTTCAAGGTTCACACGTACCTCCCACTTT

CGGCCAGGGAACCAAGCTGGAAATCAAG

Humanized 16B1 Anti-PDGF-C Antibody
Heavy Chain Variable Region (SEQ ID NO: 110)
GAGGTGCAGCTTCTGGAATCTGGGGAGGTCTTGTGCAGCCAGG

AGGGTCCCTGCGGCTCTCCTGTGCCGCATCTGGATTCACTTTCA

GTAATTATGGCATGTCTTGGGTTCGCCAGACTCCTGGCAAAGGG

CTGGAGTGGGTCGCAACCATTGGCAGTGGTGGGAGTTATACCTA

CTATCCAGATTCAGTGAAGGGACGCTTTACCATCAGCAGAGACA

ATGCCAAGAACACCTTGTACCTGCAAATGAACAGTCTGCGAGCC

GAAGACACAGCCGTGTACTATTGCGCTAGGCAGGCTCCCCTCTG

GGACTACAGCGATTACTGGGGCCAAGGCACATTGCTCACAGTCT

CCTCA

Light Chain Variable Region (SEQ ID NO: 111)
GACGTTGTGATGACCCAATCTCCCTTGTCCCTGCCTGTCACTCT

TGGGCAGCCTGCCTCCATTAGCTGTCGCTCTAACCAGAGCATTG

TGCATAGTAACGGCGACACCTACCTGGAATGGTATCTTCAGAAA

CCAGGCCAGAGCCCACGGCTCCTGATCTACAAAGTTTCCAACAG

GTTTAGTGGGGTCCCAGACAGGTTCTCCGGCAGTGGATCAGGGA

CAGATTTCACACTCAAGATAAGCAGAGTGGAGGCTGAGGATGTG

GGAGTCTACTATTGCTTTCAAGGTTCACACGTACCTCCCACTTT

CGGCCAGGGAACCAAGCTGGAAATCAAG

Humanized 29H1 Anti-PDGF-C Antibody
Heavy Chain Variable Region (SEQ ID NO: 112)
GAGGTGCAGCTTCTGGAATCTGGGGGAGGTCTTGTGCAGCCAGG

AGGGTCCCTGCGGCTCTCCTGTGCCGCATCTGGATTCACTTTCA

GTAATTATGGCATGTCTTGGGTTCGCCAGACTCCTGGCAAAGGG

CTGGAGTGGGTCGCAACCATTGGCAGTGGTGGGCACTATACCTA

CTATCCAGATTCAGTGAAGGGACGCTTTACCATCAGCAGAGACA

ATGCCAAGAACACCTTGTACCTGCAAATGAACAGTCTGCGAGCC

GAAGACACAGCCGTGTACTATTGCGCTAGGCAGGCTCCCCTCTG

GGACTGTAGCGATTACTGGGGCCAAGGCACATTGCTCACAGTCT

CCTCA

Light Chain Variable Region (SEQ ID NO: 113)
GACGTTGTGATGACCCAATCTCCCTTGTCCCTGCCTGTCACTCT

TGGGCAGCCTGCCTCCATTAGCTGTCGCTCTAGCCAGACCATTG

TGCATAGTGACGGCACAACCTACCTGGAATGGTATCTTCAGAAA

CCAGGCCAGAGCCCACGGCTCCTGATCTACAAAGTTTCCAACAG

GTTTAGTGGGGTCCCAGACAGGTTCTCCGGCAGTGGATCAGGGA

CAGATTTCACACTCAAGATAAGCAGAGTGGAGGCTGAGGATGTG

GGAGTCTACTATTGCTTTCAAGGTTCACACGTACCTCCCACTTT

CGGCCAGGGAACCAAGCTGGAAATCAAG

The affinity of the above-listed exemplary humanized anti-PDGF-C antibodies for PDGF-C was analysed (as in Example 3) and the humanized antibodies were subsequently assessed in the in vitro bioassay described in Example 4. Results are summarized in Tables 9 and 10, respectively. A technical problem with the (preparation of) humanized antibody 5H7 may explain why this antibody is apparently not inhibiting activation of PDGFR-α although it is still binding with high affinity to PDGF-C; this is under further investigation.

TABLE 9

Affinity of humanized anti-PDGF-C antibodies for PDGF-C

| Humanized anti-PDGF-C antibody | $K_D$ (nM) |
|---|---|
| mAb 5H7 | 2.5 nM |
| mAb 16B1 | 0.8 nM |
| mAb 29H1 | 0.7 nM |

TABLE 10

Inhibition of activation of PDGFR-α by PDGF-C
in the presence of humanized anti-PDGF-C antibodies

| Humanized anti-PDGF-C antibody | IC50 value (nM) |
|---|---|
| mAb 5H7 | nad |
| mAb 16B1 | 4.97* |
| mAb 29H1 | 8.24* |

*average value of 3 separate measurements;
"nad": not able to determine

The invention claimed is:

1. An antibody or antigen-binding fragment thereof that specifically binds to human Platelet-derived Growth Factor C (PDGF-C), wherein the antibody or antigen-binding fragment thereof comprises one of the following combinations of complementarity determining region (CDR) amino acid sequences:
   (i) light chain CDR 1 with amino acid sequence defined in SEQ ID NO: 22; light chain CDR 2 and 3 with amino acid sequences defined in SEQ ID NO: 24 and 25, respectively; heavy chain CDR 1 with amino acid sequence defined in SEQ ID NO: 27; heavy chain CDR 2 with amino acid sequence defined in SEQ ID NO: 29; and heavy chain CDR 3 with amino acid sequence defined in SEQ ID NO: 32;
   (ii) light chain CDR 1 to 3 with amino acid sequences defined in SEQ ID NO: 22, 24 and 25, respectively; heavy chain CDR 1 with amino acid sequence defined in SEQ ID NO: 27; heavy chain CDR 2 with amino acid sequence defined in SEQ ID NO: 30; and heavy chain CDR 3 with amino acid sequence defined in SEQ ID NO: 33;
   (iii) light chain CDR 1 to 3 with amino acid sequences defined in SEQ ID NO: 23 to 25, respectively; heavy chain CDR 1 with amino acid sequence defined in SEQ ID NO: 28; heavy chain CDR 2 with amino acid sequence defined in SEQ ID NO: 31; and heavy chain CDR 3 with amino acid sequence defined in SEQ ID NO: 34; or
   (iv) light chain CDR 1 to 3 with amino acid sequences defined in SEQ ID NO: 38, 24, and 25, respectively; heavy chain CDR 1 with amino acid sequence defined in SEQ ID NO: 27; heavy chain CDR 2 with amino acid sequence defined in SEQ ID NO: 30; and heavy chain CDR 3 with amino acid sequence defined in SEQ ID NO: 33.

2. The antibody or antigen-binding fragment thereof of claim 1, wherein the antibody or antigen-binding fragment thereof is a mammalian antibody, a human antibody, or a humanized antibody.

3. The antibody or antigen-binding fragment thereof of claim 1, wherein the antibody or antigen-binding fragment thereof is a monovalent or a multivalent antibody.

4. A pharmaceutical composition comprising the antibody or antigen-binding fragment thereof of claim 1 and further comprising at least one of a pharmaceutically acceptable diluent, carrier, or adjuvant.

5. The pharmaceutical composition according to claim 4 further comprising an additional therapeutic agent.

6. A method for inhibiting a benign, pre-malignant or malignant tumor in a human subject in need thereof, the method comprising administering an effective amount of the antibody or antigen-binding fragment thereof of claim 1 to the subject.

7. The method of claim 6, wherein the antibody or antigen-binding fragment thereof is administered with an additional therapeutic agent.

8. A method for inhibiting neovascularization in an ophthalmologic disorder selected from the group consisting of diabetic retinopathy, age-related macular edema, rubeosis iridis, choroidal neovascularization, degenerative maculopathy, corneal neovascularization, neovascular glaucoma, retinopathy of prematurity, and hyperplastic vitreous syndrome in a human subject in need thereof, the method comprising administering an effective amount of the antibody or antigen-binding fragment thereof of claim 1 to the subject.

9. A method for inhibiting neovascularization in a human subject in need thereof, the method comprising administering an effective amount of the antibody or antigen-binding fragment thereof of claim 1 to the subject.

10. A conjugate comprising the antibody or the antigen-binding fragment thereof of claim 1 conjugated with another compound.

11. The antibody or the antigen-binding fragment thereof of claim 1, wherein the antibody or the antigen-binding fragment thereof binds to PDGF-C with a dissociation constant of 10 nM or lower.

12. The antibody or antigen-binding fragment thereof of claim 1, wherein the antibody or antigen-binding fragment thereof is a humanized antibody.

13. The antibody or antigen-binding fragment thereof of claim 1, wherein the antibody or antigen-binding fragment thereof comprises the following combinations of CDR amino acid sequences:
    light chain CDR 1 to 3 with amino acid sequences defined in SEQ ID NO: 22, 24 and 25, respectively; and
    heavy chain CDR 1 to 3 with amino acid sequences defined in SEQ ID NO: 27, 29, and 32, respectively.

14. The antibody or antigen-binding fragment thereof of claim 13, comprising a variable heavy chain defined by SEQ ID NO:106 and a variable light chain defined by SEQ ID NO:107.

15. The antibody or antigen-binding fragment thereof of claim 13, wherein the antibody or antigen-binding fragment thereof is a humanized antibody or antigen-binding fragment thereof comprising:

(i) a variable heavy chain defined in SEQ ID NO:21 but carrying up to 16 mutations in the region outside the CDRs;
(ii) a variable light chain defined in SEQ ID NO:17 but carrying up to 9 mutations in the region outside the CDRs;
(iii) a variable heavy chain defined in SEQ ID NO:21 but carrying up to 16 mutations in the region outside the CDRs, and a variable light chain defined in SEQ ID NO: 17 but carrying up to 9 mutations in the region outside the CDRs;
(iv) a variable heavy chain defined in SEQ ID NO:19 but carrying up to 16 mutations in the region outside the CDRs;
(v) a variable light chain defined in SEQ ID NO:15 but carrying up to 9 mutations in the region outside the CDRs;
(vi) a variable heavy chain defined in SEQ ID NO:19 but carrying up to 16 mutations in the region outside the CDRs, and a variable light chain defined in SEQ ID NO: 15 but carrying up to 9 mutations in the region outside the CDRs;
(vii) a variable light chain defined in SEQ ID NO:15 but carrying one or more of the following mutations: Leu3Val, Thr7Ser, Ser14Thr, Asp17Gln, Gln18Pro, Lys50Arg, Leu88Val and/or Gly105Gln;
(viii) a variable heavy chain defined in SEQ ID NO:21 but carrying one or more of the following mutations: Val5Leu, Asp10Gly, Lys13Gln, Lys19Arg, Asp42Gly, Arg44Gly, Ser74Asn, Ser77Asn, Ser84Asn, Ser88Ala, Ile93Val, and/or Thr114Leu;
(ix) a variable light chain defined in SEQ ID NO:17 but carrying one or more of the following mutations: Leu3Val, Thr7Ser, Ser14Thr, Asp17Gln, Gln18Pro, Asn50Arg, Leu88Val and/or Gly105Gln; or
(x) a variable heavy chain defined in SEQ ID NO:21 but carrying one or more of the following mutations: Val5Leu, Asp10Gly, Lys13Gln, Lys19Arg, Asp42Gly, Arg44Gly, Ser74Asn, Ser77Asn, Ser84Asn, Ser88Ala, Ile93Val, and/or Thr114Leu, and a variable light chain defined in SEQ ID NO:17 but carrying one or more of the following mutations: Leu3Val, Thr7Ser, Ser14Thr, Asp17Gln, Gln18Pro, Asn50Arg, Leu88Val and/or Gly105Gln.

16. A method for inhibiting a benign, pre-malignant or malignant tumor in a human subject in need thereof, the method comprising administering an effective amount of the antibody or antigen-binding fragment thereof of claim 13 to the subject.

17. A method for inhibiting neovascularization in an ophthalmologic disorder selected from the group consisting of diabetic retinopathy, age-related macular edema, rubeosis iridis, choroidal neovascularization, degenerative maculopathy, corneal neovascularization, neovascular glaucoma, retinopathy of prematurity, and hyperplastic vitreous syndrome in a human subject in need thereof, the method comprising administering an effective amount of the antibody or antigen-binding fragment thereof of claim 13 to the subject.

18. A method for inhibiting neovascularization in a human subject in need thereof, the method comprising administering an effective amount of the antibody or antigen-binding fragment thereof of claim 13 to the subject.

19. A conjugate comprising the antibody or the antigen-binding fragment thereof of claim 13 conjugated with another compound.

20. A method for inhibiting the binding of platelet derived growth factor C (PDGF-C) to platelet derived growth factor receptor alpha (PDGFRα) in a human subject in need thereof, the method comprising administering an effective amount of the antibody or antigen-binding fragment of claim 13 to the subject.

21. The method of claim 20, wherein the antibody or antigen-binding fragment is administered to the eye of the subject.

22. The antibody or antigen-binding fragment thereof of claim 1, wherein the antibody or antigen-binding fragment thereof comprises the following combinations of CDR amino acid sequences:
light chain CDR 1 to 3 with amino acid sequences defined in SEQ ID NO: 38, 24 and 25, respectively; and heavy chain CDR 1 to 3 with amino acid sequences defined in SEQ ID NO: 27, 30, and 33, respectively.

23. The antibody or antigen-binding fragment thereof of claim 22, wherein the antibody or antigen-binding fragment thereof is a humanized antibody or antigen-binding fragment thereof comprising:
(i) a variable heavy chain defined in SEQ ID NO:18 but carrying up to 16 mutations in the region outside the CDRs;
(ii) a variable light chain defined in SEQ ID NO:14 but carrying up to 9 mutations in the region outside the CDRs;
(iii) a variable heavy chain defined in SEQ ID NO:18 but carrying up to 16 mutations in the region outside the CDRs, and a variable light chain defined in SEQ ID NO: 14 but carrying up to 9 mutations in the region outside the CDRs; or
(iv) a variable heavy chain defined in SEQ ID NO:18 but carrying one or more of the following mutations: Val5Leu, Asp10Gly, Lys13Gln, Lys19Arg, Asp42Gly, Arg44Gly, Ser74Asn, Ser84Asn, Lys87Arg, Ser88Ala, Met93Val, and/or Thr114Leu.

24. A method for inhibiting a benign, pre-malignant or malignant tumor in a human subject in need thereof, the method comprising administering an effective amount of the antibody or antigen-binding fragment thereof of claim 22 to the subject.

25. A method for inhibiting neovascularization in an ophthalmologic disorder selected from the group consisting of diabetic retinopathy, age-related macular edema, rubeosis iridis, choroidal neovascularization, degenerative maculopathy, corneal neovascularization, neovascular glaucoma, retinopathy of prematurity, and hyperplastic vitreous syndrome in a human subject in need thereof, the method comprising administering an effective amount of the antibody or antigen-binding fragment thereof of claim 22 to the subject.

26. A method for inhibiting neovascularization in a human subject in need thereof, the method comprising administering an effective amount of the antibody or antigen-binding fragment thereof of claim 22 to the subject.

27. A conjugate comprising the antibody or the antigen-binding fragment thereof of claim 22 conjugated with another compound.

28. A method for inhibiting the binding of platelet derived growth factor C (PDGF-C) to platelet derived growth factor receptor alpha (PDGFRα) in a human subject in need thereof, the method comprising administering an effective amount of the antibody or antigen-binding fragment of claim 22 to the subject.

29. The method of claim 28, wherein the antibody or antigen-binding fragment is administered to the eye of the subject.

30. The antibody or antigen-binding fragment thereof of claim 1, wherein the antibody or antigen-binding fragment thereof comprises the following combinations of CDR amino acid sequences:
  light chain CDR 1 to 3 with amino acid sequences defined in SEQ ID NO: 22, 24 and 25, respectively; and heavy chain CDR 1 to 3 with amino acid sequences defined in SEQ ID NO: 27, 30, and 33, respectively.

31. The antibody or antigen-binding fragment thereof of claim 30, comprising a variable heavy chain defined by SEQ ID NO:104 and a variable light chain defined by SEQ ID NO:105.

32. The antibody or antigen-binding fragment thereof of claim 30, wherein the antibody or antigen-binding fragment thereof is a humanized antibody or antigen-binding fragment thereof comprising:
  (i) a variable heavy chain defined in SEQ ID NO:18 but carrying up to 16 mutations in the region outside the CDRs;
  (ii) a variable light chain defined in SEQ ID NO: 15 but carrying up to 9 mutations in the region outside the CDRs;
  (iii) a variable heavy chain defined in SEQ ID NO:18 but carrying up to 16 mutations in the region outside the CDRs, and a variable light chain defined in SEQ ID NO: 15 but carrying up to 9 mutations in the region outside the CDRs;
  (iv) a variable heavy chain defined in SEQ ID NO:18 but carrying one or more of the following mutations: Val5Leu, Asp10Gly, Lys13Gln, Lys19Arg, Asp42Gly, Arg44Gly, Ser74Asn, Ser84Asn, Lys87Arg, Ser88Ala, Met93Val, and/or Thr114Leu;
  (v) a variable light chain defined in SEQ ID NO:15 but carrying one or more of the following mutations: Leu3Val, Thr7Ser, Ser14Thr, Asp17Gln, Gln18Pro, Lys50Arg, Leu88Val and/or Gly105Gln; or
  (vi) a variable heavy chain defined in SEQ ID NO:18 but carrying one or more of the following mutations: Val5Leu, Asp10Gly, Lys13Gln, Lys19Arg, Asp42Gly, Arg44Gly, Ser74Asn, Ser84Asn, Lys87Arg, Ser88Ala, Met93Val, and/or Thr114Leu, and a variable light chain defined in SEQ ID NO:15 but carrying one or more of the following mutations: Leu3Val, Thr7Ser, Ser14Thr, Asp17Gln, Gln18Pro, Lys50Arg, Leu88Val and/or Gly105Gln.

33. A method for inhibiting a benign, pre-malignant or malignant tumor in a human subject in need thereof, the method comprising administering an effective amount of the antibody or antigen-binding fragment thereof of claim 30 to the subject.

34. A method for inhibiting neovascularization in an ophthalmologic disorder selected from the group consisting of diabetic retinopathy, age-related macular edema, rubeosis iridis, choroidal neovascularization, degenerative maculopathy, corneal neovascularization, neovascular glaucoma, retinopathy of prematurity, and hyperplastic vitreous syndrome in a human subject in need thereof, the method comprising administering an effective amount of the antibody or antigen-binding fragment thereof of claim 30 to the subject.

35. A method for inhibiting neovascularization in a human subject in need thereof, the method comprising administering an effective amount of the antibody or antigen-binding fragment thereof of claim 30 to the subject.

36. A conjugate comprising the antibody or the antigen-binding fragment thereof of claim 30 conjugated with another compound.

37. A method for inhibiting the binding of platelet derived growth factor C (PDGF-C) to platelet derived growth factor receptor alpha (PDGFRα) in a human subject in need thereof, the method comprising administering an effective amount of the antibody or antigen-binding fragment of claim 30 to the subject.

38. The method of claim 37, wherein the antibody or antigen-binding fragment is administered to the eye of the subject.

39. The antibody or antigen-binding fragment thereof of claim 1, wherein the antibody or antigen-binding fragment thereof comprises the following combinations of CDR amino acid sequences:
  light chain CDR 1 to 3 with amino acid sequences defined in SEQ ID NO: 23, 24 and 25, respectively; and heavy chain CDR 1 to 3 with amino acid sequences defined in SEQ ID NO: 28, 31, and 34, respectively.

40. The antibody or antigen-binding fragment thereof of claim 39, comprising a variable heavy chain defined by SEQ ID NO:102 and a variable light chain defined by SEQ ID NO:103.

41. The antibody or antigen-binding fragment thereof of claim 39, wherein the antibody or antigen-binding fragment thereof is a humanized antibody or antigen-binding fragment thereof comprising:
  (i) a variable heavy chain defined in SEQ ID NO:20 but carrying up to 16 mutations in the region outside the CDRs;
  (ii) a variable light chain defined in SEQ ID NO:16 but carrying up to 9 mutations in the region outside the CDRs;
  (iii) a variable heavy chain defined in SEQ ID NO:20 but carrying up to 16 mutations in the region outside the CDRs, and a variable light chain defined in SEQ ID NO:16 but carrying up to 9 mutations in the region outside the CDRs;
  (iv) a variable heavy chain defined in SEQ ID NO:20 but carrying one or more of the following mutations: Val5Leu, Asp10Gly, Lys13Gln, Lys19Arg, Asp42Gly, Arg44Gly, Phe80Tyr, Ser84Asn, Lys87Arg, Ser88Ala, Ile93Val, Val97Ala, and/or Thr114Leu;
  (v) a variable light chain defined in SEQ ID NO:16 but carrying one or more of the following mutations: Leu3Val, Thr7Ser, Ser14Thr, Asp17Gln, Gln18Pro, Ala45Pro, Lys50Arg, Leu88Val and/or Gly105Gln; or
  (vi) a variable heavy chain defined in SEQ ID NO:20 but carrying one or more of the following mutations: Val5Leu, Asp10Gly, Lys13Gln, Lys19Arg, Asp42Gly, Arg44Gly, Phe80Tyr, Ser84Asn, Lys87Arg, Ser88Ala, Ile93Val, Val97Ala, and/or Thr114Leu, and a variable light chain defined in SEQ ID NO:16 but carrying one or more of the following mutations: Leu3Val, Thr7Ser, Ser14Thr, Asp17Gln, Gln18Pro, Ala45Pro, Lys50Arg, Leu88Val and/or Gly105Gln.

42. A method for inhibiting a benign, pre-malignant or malignant tumor in a human subject in need thereof, the method comprising administering an effective amount of the antibody or antigen-binding fragment thereof of claim 39 to the subject.

43. A method for inhibiting neovascularization in an ophthalmologic disorder selected from the group consisting of diabetic retinopathy, age-related macular edema, rubeosis iridis, choroidal neovascularization, degenerative maculopathy, corneal neovascularization, neovascular glaucoma, retinopathy of prematurity, and hyperplastic vitreous syndrome in a human subject in need thereof, the method comprising administering an effective amount of the antibody or antigen-binding fragment thereof of claim 39 to the subject.

44. A method for inhibiting neovascularization in a human subject in need thereof, the method comprising administering an effective amount of the antibody or antigen-binding fragment thereof of claim 39 to the subject.

45. A conjugate comprising the antibody or the antigen-binding fragment thereof of claim 39 conjugated with another compound.

46. A method for inhibiting the binding of platelet derived growth factor C (PDGF-C) to platelet derived growth factor receptor alpha (PDGFRα) in a human subject in need thereof, the method comprising administering an effective amount of the antibody or antigen-binding fragment of claim 39 to the subject.

47. The method of claim 46, wherein the antibody or antigen-binding fragment is administered to the eye of the subject.

48. A method for inhibiting the binding of platelet derived growth factor C (PDGF-C) to platelet derived growth factor receptor alpha (PDGFRα) in a human subject in need thereof, the method comprising administering an effective amount of the antibody or antigen-binding fragment of claim 1 to the subject.

49. The method of claim 48, wherein the antibody or antigen-binding fragment is administered to the eye of the subject.

* * * * *

SEQUENCE LISTING

<160> NUMBER OF SEQ ID NOS: 113

<210> SEQ ID NO 1
<211> LENGTH: 24
<212> TYPE: DNA
<213> ORGANISM: artificial
<220> FEATURE:
<223> OTHER INFORMATION: synthetic oligonucleotide

<400> SEQUENCE: 1
atgaagttgc ctgttaggct gttg                                           24

<210> SEQ ID NO 2
<211> LENGTH: 24
<212> TYPE: DNA
<213> ORGANISM: artificial
<220> FEATURE:
<223> OTHER INFORMATION: synthetic oligonucleotide

<400> SEQUENCE: 2
gctcactgga tggtgggaag atgg                                           24

<210> SEQ ID NO 3
<211> LENGTH: 24
<212> TYPE: DNA
<213> ORGANISM: artificial
<220> FEATURE:
<223> OTHER INFORMATION: synthetic oligonucleotide

<400> SEQUENCE: 3
atggayttyg ggctgakytt kdtt                                           24

<210> SEQ ID NO 4
<211> LENGTH: 25
<212> TYPE: DNA
<213> ORGANISM: artificial
<220> FEATURE:
<223> OTHER INFORMATION: synthetic oligonucleotide

<400> SEQUENCE: 4
casaymcagg ggccagtgga tagac                                          25

<210> SEQ ID NO 5
<211> LENGTH: 16
<212> TYPE: DNA
<213> ORGANISM: artificial
<220> FEATURE:
<223> OTHER INFORMATION: synthetic oligonucleotide

<400> SEQUENCE: 5
gtaaaacgac ggccag                                                    16

<210> SEQ ID NO 6
<211> LENGTH: 17
<212> TYPE: DNA
<213> ORGANISM: artificial
<220> FEATURE:
<223> OTHER INFORMATION: synthetic oligonucleotide

<400> SEQUENCE: 6
caggaaacag ctatgac                                                   17

<210> SEQ ID NO 7
<211> LENGTH: 11
<212> TYPE: PRT
<213> ORGANISM: Mus musculus

<400> SEQUENCE: 7

Asp Val Leu Met Thr Gln Thr Pro Leu Ser Leu
1               5                   10

<210> SEQ ID NO 8
<211> LENGTH: 11
<212> TYPE: PRT
<213> ORGANISM: Mus musculus

<400> SEQUENCE: 8

Glu Val Gln Leu Val Glu Ser Gly Gly Asp Leu
1               5                   10

<210> SEQ ID NO 9
<211> LENGTH: 336
<212> TYPE: DNA
<213> ORGANISM: Mus musculus

<400> SEQUENCE: 9

```
gatgttttga tgacccaaac tccactctcc ctgcctgtca gtcttggaga tcaagcctcc     60
atctcttgca gatctaatca gascattgta catagtaatg agacaccta tttagaatgg     120
tacctgcaga aaccaggcca gtctccaaak ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcct    300
cccacgttcg agggggggac caagctggaa ataaaa                              336
```

<210> SEQ ID NO 10
<211> LENGTH: 336
<212> TYPE: DNA
<213> ORGANISM: Mus musculus

<400> SEQUENCE: 10

```
gatgttttga tgacccaaac tccactctcc ctgcctgtca gtcttggaga tcaagcctcc     60
atctcttgca gatctagtca gaccattgta catagtgatg aaccaccta tttagaatgg     120
taccttcaga aagcaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcct    300
cccacgttcg agggggggac caagctggaa ataaaa                              336
```

<210> SEQ ID NO 11
<211> LENGTH: 357
<212> TYPE: DNA
<213> ORGANISM: Mus musculus

<400> SEQUENCE: 11

```
gaggtgcagc tggtggartc tgggggagac ttagtgaagc ctggagggtc cctgaaactc     60
tcctgtgcag cctctggatt cactttcagt aactatggca tgtcttgggt tcgccagact    120
ccagacaaga ggctggagtg ggtcgcaacc attggtagtg gtggtagtta cacctactat    180
ccrgacagtg tgaaggggcg attcaccatc tccagagaca gtgccaagaa caccctgtac    240
ctgcaaatga gcagtctgaa gtctgaggac acagccatgt attactgtgc aagacaggcc    300
cccctctggg actactctga ctactggggc caaggcacca ctctcactgt ctcctcg       357
```

<210> SEQ ID NO 12

<211> LENGTH: 357
<212> TYPE: DNA
<213> ORGANISM: Mus musculus

<400> SEQUENCE: 12

```
gaggtgcagc tggtggaatc tgggggagac ttagtgaagc tggagggtc cctgaaactc      60
tcctgtgcag cctctggatt cactttcagt aactatggca tgtcttgggt tcgccagact    120
ccagacaaga ggctggagtg ggtcgcaacc attggtagtg gtggtcatta cacctactat    180
ccagacagtg tgaaggggcg attcaccatc tccagagaca gtgccaagag cacactgtac    240
ctgcaaatga gcagtctgar gtctgasgac acagccatat attactgtgc aagacaggcc    300
cccctctggg actgctctga ctactggggc caaggcacca ctctcactgt ctcctcg      357
```

<210> SEQ ID NO 13
<211> LENGTH: 357
<212> TYPE: DNA
<213> ORGANISM: Mus musculus

<400> SEQUENCE: 13

```
gaggtgcagc tggtggagtc tgggggagac ttagtgaagc tggagggtc cctgaaactc      60
tcctgtgcag cctctggatt cactttcagt agctatggca tgtcttgggt tcgccagact    120
ccagacaaga ggctggagtg ggtcgcaacc attggttatg gtggtagttt cacctactat    180
ccagatagta tgaaggggcg cttcaccatc tccagagaca atgccaagaa caccctgttc    240
ctgcaaatga gcagtctgaa gtctgaggac acagccatat attactgtgt aagacaggcc    300
cccctctggg actactttga ctactggggc caaggcacca ctctcacagt ctcctca      357
```

<210> SEQ ID NO 14
<211> LENGTH: 112
<212> TYPE: PRT
<213> ORGANISM: Mus musculus

<400> SEQUENCE: 14

```
Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110
```

<210> SEQ ID NO 15
<211> LENGTH: 112
<212> TYPE: PRT
<213> ORGANISM: Mus musculus

<400> SEQUENCE: 15

```
Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Val His Ser
```

```
            20                  25                  30

Asn Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 16
<211> LENGTH: 112
<212> TYPE: PRT
<213> ORGANISM: Mus musculus

<400> SEQUENCE: 16

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asp Gly Thr Thr Tyr Leu Glu Trp Tyr Leu Gln Lys Ala Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 17
<211> LENGTH: 112
<212> TYPE: PRT
<213> ORGANISM: Mus musculus

<400> SEQUENCE: 17

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Val His Ser
            20                  25                  30

Asn Gly Asp Thr Tyr Leu Glu Trp Tyr Leu Gln Lys Pro Gly Gln Ser
            35                  40                  45

Pro Asn Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 18
<211> LENGTH: 119
<212> TYPE: PRT
```

```
<213> ORGANISM: Mus musculus

<400> SEQUENCE: 18

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Gly Ser Gly Ser Tyr Thr Tyr Tyr Pro Asp Ser Val
    50                  55                  60

Lys Gly Arg Phe Thr Ile Ser Arg Asp Ser Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Ala Pro Leu Trp Asp Tyr Ser Asp Tyr Trp Gly Gln Gly
                100                 105                 110

Thr Thr Leu Thr Val Ser Ser
            115

<210> SEQ ID NO 19
<211> LENGTH: 119
<212> TYPE: PRT
<213> ORGANISM: Mus musculus

<400> SEQUENCE: 19

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Gly Ser Gly Gly His Tyr Thr Tyr Tyr Pro Asp Ser Val
    50                  55                  60

Lys Gly Arg Phe Thr Ile Ser Arg Asp Ser Ala Lys Ser Thr Leu Tyr
65                  70                  75                  80

Leu Gln Met Ser Ser Leu Lys Ser Glu Asp Thr Ala Ile Tyr Tyr Cys
                85                  90                  95

Ala Arg Gln Ala Pro Leu Trp Asp Cys Ser Asp Tyr Trp Gly Gln Gly
                100                 105                 110

Thr Thr Leu Thr Val Ser Ser
            115

<210> SEQ ID NO 20
<211> LENGTH: 119
<212> TYPE: PRT
<213> ORGANISM: Mus musculus

<400> SEQUENCE: 20

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Gly Tyr Gly Gly Ser Phe Thr Tyr Tyr Pro Asp Ser Met
    50                  55                  60
```

Lys Gly Arg Phe Thr Ile Ser Arg Asp Asn Ala Lys Asn Thr Leu Phe
65                  70                  75                  80

Leu Gln Met Ser Ser Leu Lys Ser Glu Asp Thr Ala Ile Tyr Tyr Cys
                85                  90                  95

Val Arg Gln Ala Pro Leu Trp Asp Tyr Phe Asp Tyr Trp Gly Gln Gly
            100                 105                 110

Thr Thr Leu Thr Val Ser Ser
        115

<210> SEQ ID NO 21
<211> LENGTH: 119
<212> TYPE: PRT
<213> ORGANISM: Mus musculus

<400> SEQUENCE: 21

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Gly Ser Gly Gly His Tyr Thr Tyr Tyr Pro Asp Ser Val
    50                  55                  60

Lys Gly Arg Phe Thr Ile Ser Arg Asp Ser Ala Lys Ser Thr Leu Tyr
65                  70                  75                  80

Leu Gln Met Ser Ser Leu Arg Ser Asp Asp Thr Ala Ile Tyr Tyr Cys
                85                  90                  95

Ala Arg Gln Ala Pro Leu Trp Asp Cys Ser Asp Tyr Trp Gly Gln Gly
            100                 105                 110

Thr Thr Leu Thr Val Ser Ser
        115

<210> SEQ ID NO 22
<211> LENGTH: 16
<212> TYPE: PRT
<213> ORGANISM: Mus musculus

<400> SEQUENCE: 22

Arg Ser Asn Gln Ser Ile Val His Ser Asn Gly Asp Thr Tyr Leu Glu
1               5                   10                  15

<210> SEQ ID NO 23
<211> LENGTH: 16
<212> TYPE: PRT
<213> ORGANISM: Mus musculus

<400> SEQUENCE: 23

Arg Ser Ser Gln Thr Ile Val His Ser Asp Gly Thr Thr Tyr Leu Glu
1               5                   10                  15

<210> SEQ ID NO 24
<211> LENGTH: 7
<212> TYPE: PRT
<213> ORGANISM: Mus musculus

<400> SEQUENCE: 24

Lys Val Ser Asn Arg Phe Ser
1               5

-continued

<210> SEQ ID NO 25
<211> LENGTH: 9
<212> TYPE: PRT
<213> ORGANISM: Mus musculus

<400> SEQUENCE: 25

Phe Gln Gly Ser His Val Pro Pro Thr
1               5

<210> SEQ ID NO 26
<211> LENGTH: 16
<212> TYPE: PRT
<213> ORGANISM: Mus musculus
<220> FEATURE:
<221> NAME/KEY: MISC_FEATURE
<222> LOCATION: (3)..(3)
<223> OTHER INFORMATION: Xaa can be Asn or Ser
<220> FEATURE:
<221> NAME/KEY: MISC_FEATURE
<222> LOCATION: (5)..(5)
<223> OTHER INFORMATION: Xaa can be Ser or Thr
<220> FEATURE:
<221> NAME/KEY: MISC_FEATURE
<222> LOCATION: (10)..(10)
<223> OTHER INFORMATION: Xaa can be Asp or Asn
<220> FEATURE:
<221> NAME/KEY: MISC_FEATURE
<222> LOCATION: (12)..(12)
<223> OTHER INFORMATION: Xaa can be Asp or Thr

<400> SEQUENCE: 26

Arg Ser Ser Gln Xaa Ile Val His Ser Xaa Gly Xaa Thr Tyr Leu Glu
1               5                   10                  15

<210> SEQ ID NO 27
<211> LENGTH: 5
<212> TYPE: PRT
<213> ORGANISM: Mus musculus

<400> SEQUENCE: 27

Asn Tyr Gly Met Ser
1               5

<210> SEQ ID NO 28
<211> LENGTH: 5
<212> TYPE: PRT
<213> ORGANISM: Mus musculus

<400> SEQUENCE: 28

Ser Tyr Gly Met Ser
1               5

<210> SEQ ID NO 29
<211> LENGTH: 17
<212> TYPE: PRT
<213> ORGANISM: Mus musculus

<400> SEQUENCE: 29

Thr Ile Gly Ser Gly Gly His Tyr Thr Tyr Tyr Pro Asp Ser Val Lys
1               5                   10                  15

Gly

<210> SEQ ID NO 30
<211> LENGTH: 17
<212> TYPE: PRT
<213> ORGANISM: Mus musculus

<400> SEQUENCE: 30

-continued

```
Thr Ile Gly Ser Gly Gly Ser Tyr Thr Tyr Tyr Pro Asp Ser Val Lys
1               5                   10                  15

Gly

<210> SEQ ID NO 31
<211> LENGTH: 17
<212> TYPE: PRT
<213> ORGANISM: Mus musculus

<400> SEQUENCE: 31

Thr Ile Gly Tyr Gly Gly Ser Phe Thr Tyr Tyr Pro Asp Ser Met Lys
1               5                   10                  15

Gly

<210> SEQ ID NO 32
<211> LENGTH: 10
<212> TYPE: PRT
<213> ORGANISM: Mus musculus

<400> SEQUENCE: 32

Gln Ala Pro Leu Trp Asp Cys Ser Asp Tyr
1               5                   10

<210> SEQ ID NO 33
<211> LENGTH: 10
<212> TYPE: PRT
<213> ORGANISM: Mus musculus

<400> SEQUENCE: 33

Gln Ala Pro Leu Trp Asp Tyr Ser Asp Tyr
1               5                   10

<210> SEQ ID NO 34
<211> LENGTH: 10
<212> TYPE: PRT
<213> ORGANISM: Mus musculus

<400> SEQUENCE: 34

Gln Ala Pro Leu Trp Asp Tyr Phe Asp Tyr
1               5                   10

<210> SEQ ID NO 35
<211> LENGTH: 5
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa can be Asn or Ser

<400> SEQUENCE: 35

Xaa Tyr Gly Met Ser
1               5

<210> SEQ ID NO 36
<211> LENGTH: 17
<212> TYPE: PRT
<213> ORGANISM: Mus musculus
<220> FEATURE:
<221> NAME/KEY: MISC_FEATURE
<222> LOCATION: (4)..(4)
<223> OTHER INFORMATION: Xaa can be Ser or Tyr
<220> FEATURE:
<221> NAME/KEY: MISC_FEATURE
<222> LOCATION: (7)..(7)
```

```
<223> OTHER INFORMATION: Xaa can be Ser or His
<220> FEATURE:
<221> NAME/KEY: MISC_FEATURE
<222> LOCATION: (8)..(8)
<223> OTHER INFORMATION: Xaa can be Phe or Tyr
<220> FEATURE:
<221> NAME/KEY: MISC_FEATURE
<222> LOCATION: (15)..(15)
<223> OTHER INFORMATION: Xaa can be Val or Met

<400> SEQUENCE: 36

Thr Ile Gly Xaa Gly Gly Xaa Xaa Thr Tyr Tyr Pro Asp Ser Xaa Lys
1               5                   10                  15

Gly

<210> SEQ ID NO 37
<211> LENGTH: 10
<212> TYPE: PRT
<213> ORGANISM: Mus musculus
<220> FEATURE:
<221> NAME/KEY: MISC_FEATURE
<222> LOCATION: (7)..(7)
<223> OTHER INFORMATION: Xaa can be Cys or Thr
<220> FEATURE:
<221> NAME/KEY: MISC_FEATURE
<222> LOCATION: (8)..(8)
<223> OTHER INFORMATION: Xaa can be Ser or Phe

<400> SEQUENCE: 37

Gln Ala Pro Leu Trp Asp Xaa Xaa Asp Tyr
1               5                   10

<210> SEQ ID NO 38
<211> LENGTH: 16
<212> TYPE: PRT
<213> ORGANISM: Mus musculus

<400> SEQUENCE: 38

Arg Ser Asn Gln Thr Ile Val His Ser Asn Gly Asp Thr Tyr Leu Glu
1               5                   10                  15

<210> SEQ ID NO 39
<211> LENGTH: 15
<212> TYPE: PRT
<213> ORGANISM: artificial
<220> FEATURE:
<223> OTHER INFORMATION: synthetic peptide

<400> SEQUENCE: 39

Glu Ser Asn Leu Ser Ser Lys Phe Gln Phe Ser Ser Asn Lys Glu
1               5                   10                  15

<210> SEQ ID NO 40
<211> LENGTH: 15
<212> TYPE: PRT
<213> ORGANISM: artificial
<220> FEATURE:
<223> OTHER INFORMATION: synthetic peptide

<400> SEQUENCE: 40

Ser Lys Phe Gln Phe Ser Ser Asn Lys Glu Gln Asn Gly Val Gln
1               5                   10                  15

<210> SEQ ID NO 41
<211> LENGTH: 15
<212> TYPE: PRT
<213> ORGANISM: artificial
<220> FEATURE:
```

<223> OTHER INFORMATION: synthetic peptide

<400> SEQUENCE: 41

Ser Ser Asn Lys Glu Gln Asn Gly Val Gln Asp Pro Gln His Glu
1               5                   10                  15

<210> SEQ ID NO 42
<211> LENGTH: 15
<212> TYPE: PRT
<213> ORGANISM: artificial
<220> FEATURE:
<223> OTHER INFORMATION: synthetic peptide

<400> SEQUENCE: 42

Gln Asn Gly Val Gln Asp Pro Gln His Glu Arg Ile Ile Thr Val
1               5                   10                  15

<210> SEQ ID NO 43
<211> LENGTH: 15
<212> TYPE: PRT
<213> ORGANISM: artificial
<220> FEATURE:
<223> OTHER INFORMATION: synthetic peptide

<400> SEQUENCE: 43

Asp Pro Gln His Glu Arg Ile Ile Thr Val Ser Thr Asn Gly Ser
1               5                   10                  15

<210> SEQ ID NO 44
<211> LENGTH: 15
<212> TYPE: PRT
<213> ORGANISM: artificial
<220> FEATURE:
<223> OTHER INFORMATION: synthetic peptide

<400> SEQUENCE: 44

Arg Ile Ile Thr Val Ser Thr Asn Gly Ser Ile His Ser Pro Arg
1               5                   10                  15

<210> SEQ ID NO 45
<211> LENGTH: 15
<212> TYPE: PRT
<213> ORGANISM: artificial
<220> FEATURE:
<223> OTHER INFORMATION: synthetic peptide

<400> SEQUENCE: 45

Ser Thr Asn Gly Ser Ile His Ser Pro Arg Phe Pro His Thr Tyr
1               5                   10                  15

<210> SEQ ID NO 46
<211> LENGTH: 15
<212> TYPE: PRT
<213> ORGANISM: artificial
<220> FEATURE:
<223> OTHER INFORMATION: synthetic peptide

<400> SEQUENCE: 46

Ile His Ser Pro Arg Phe Pro His Thr Tyr Pro Arg Asn Thr Val
1               5                   10                  15

<210> SEQ ID NO 47
<211> LENGTH: 15
<212> TYPE: PRT
<213> ORGANISM: artificial
<220> FEATURE:
<223> OTHER INFORMATION: synthetic peptide

<400> SEQUENCE: 47

Phe Pro His Thr Tyr Pro Arg Asn Thr Val Leu Val Trp Arg Leu
1               5                   10                  15

<210> SEQ ID NO 48
<211> LENGTH: 15
<212> TYPE: PRT
<213> ORGANISM: artificial
<220> FEATURE:
<223> OTHER INFORMATION: synthetic peptide

<400> SEQUENCE: 48

Pro Arg Asn Thr Val Leu Val Trp Arg Leu Val Ala Val Glu Glu
1               5                   10                  15

<210> SEQ ID NO 49
<211> LENGTH: 15
<212> TYPE: PRT
<213> ORGANISM: artificial
<220> FEATURE:
<223> OTHER INFORMATION: synthetic peptide

<400> SEQUENCE: 49

Leu Val Trp Arg Leu Val Ala Val Glu Glu Asn Val Trp Ile Gln
1               5                   10                  15

<210> SEQ ID NO 50
<211> LENGTH: 15
<212> TYPE: PRT
<213> ORGANISM: artificial
<220> FEATURE:
<223> OTHER INFORMATION: synthetic peptide

<400> SEQUENCE: 50

Val Ala Val Glu Glu Asn Val Trp Ile Gln Leu Thr Phe Asp Glu
1               5                   10                  15

<210> SEQ ID NO 51
<211> LENGTH: 15
<212> TYPE: PRT
<213> ORGANISM: artificial
<220> FEATURE:
<223> OTHER INFORMATION: synthetic peptide

<400> SEQUENCE: 51

Asn Val Trp Ile Gln Leu Thr Phe Asp Glu Arg Phe Gly Leu Glu
1               5                   10                  15

<210> SEQ ID NO 52
<211> LENGTH: 15
<212> TYPE: PRT
<213> ORGANISM: artificial
<220> FEATURE:
<223> OTHER INFORMATION: synthetic peptide

<400> SEQUENCE: 52

Leu Thr Phe Asp Glu Arg Phe Gly Leu Glu Asp Pro Glu Asp Asp
1               5                   10                  15

<210> SEQ ID NO 53
<211> LENGTH: 15
<212> TYPE: PRT
<213> ORGANISM: artificial
<220> FEATURE:
<223> OTHER INFORMATION: synthetic peptide

```
<400> SEQUENCE: 53

Arg Phe Gly Leu Glu Asp Pro Glu Asp Asp Ile Cys Lys Tyr Asp
1               5                   10                  15

<210> SEQ ID NO 54
<211> LENGTH: 15
<212> TYPE: PRT
<213> ORGANISM: artificial
<220> FEATURE:
<223> OTHER INFORMATION: synthetic peptide

<400> SEQUENCE: 54

Asp Pro Glu Asp Asp Ile Cys Lys Tyr Asp Phe Val Glu Val Glu
1               5                   10                  15

<210> SEQ ID NO 55
<211> LENGTH: 15
<212> TYPE: PRT
<213> ORGANISM: artificial
<220> FEATURE:
<223> OTHER INFORMATION: synthetic peptide

<400> SEQUENCE: 55

Ile Cys Lys Tyr Asp Phe Val Glu Val Glu Glu Pro Ser Asp Gly
1               5                   10                  15

<210> SEQ ID NO 56
<211> LENGTH: 15
<212> TYPE: PRT
<213> ORGANISM: artificial
<220> FEATURE:
<223> OTHER INFORMATION: synthetic peptide

<400> SEQUENCE: 56

Phe Val Glu Val Glu Glu Pro Ser Asp Gly Thr Ile Leu Gly Arg
1               5                   10                  15

<210> SEQ ID NO 57
<211> LENGTH: 15
<212> TYPE: PRT
<213> ORGANISM: artificial
<220> FEATURE:
<223> OTHER INFORMATION: synthetic peptide

<400> SEQUENCE: 57

Glu Pro Ser Asp Gly Thr Ile Leu Gly Arg Trp Cys Gly Ser Gly
1               5                   10                  15

<210> SEQ ID NO 58
<211> LENGTH: 15
<212> TYPE: PRT
<213> ORGANISM: artificial
<220> FEATURE:
<223> OTHER INFORMATION: synthetic peptide

<400> SEQUENCE: 58

Thr Ile Leu Gly Arg Trp Cys Gly Ser Gly Thr Val Pro Gly Lys
1               5                   10                  15

<210> SEQ ID NO 59
<211> LENGTH: 15
<212> TYPE: PRT
<213> ORGANISM: artificial
<220> FEATURE:
<223> OTHER INFORMATION: synthetic peptide

<400> SEQUENCE: 59
```

Trp Cys Gly Ser Gly Thr Val Pro Gly Lys Gln Ile Ser Lys Gly
1               5                   10                  15

<210> SEQ ID NO 60
<211> LENGTH: 15
<212> TYPE: PRT
<213> ORGANISM: artificial
<220> FEATURE:
<223> OTHER INFORMATION: synthetic peptide

<400> SEQUENCE: 60

Thr Val Pro Gly Lys Gln Ile Ser Lys Gly Asn Gln Ile Arg Ile
1               5                   10                  15

<210> SEQ ID NO 61
<211> LENGTH: 15
<212> TYPE: PRT
<213> ORGANISM: artificial
<220> FEATURE:
<223> OTHER INFORMATION: synthetic peptide

<400> SEQUENCE: 61

Gln Ile Ser Lys Gly Asn Gln Ile Arg Ile Arg Phe Val Ser Asp
1               5                   10                  15

<210> SEQ ID NO 62
<211> LENGTH: 15
<212> TYPE: PRT
<213> ORGANISM: artificial
<220> FEATURE:
<223> OTHER INFORMATION: synthetic peptide

<400> SEQUENCE: 62

Asn Gln Ile Arg Ile Arg Phe Val Ser Asp Glu Tyr Phe Pro Ser
1               5                   10                  15

<210> SEQ ID NO 63
<211> LENGTH: 15
<212> TYPE: PRT
<213> ORGANISM: artificial
<220> FEATURE:
<223> OTHER INFORMATION: synthetic peptide

<400> SEQUENCE: 63

Arg Phe Val Ser Asp Glu Tyr Phe Pro Ser Glu Pro Gly Phe Cys
1               5                   10                  15

<210> SEQ ID NO 64
<211> LENGTH: 15
<212> TYPE: PRT
<213> ORGANISM: artificial
<220> FEATURE:
<223> OTHER INFORMATION: synthetic peptide

<400> SEQUENCE: 64

Glu Tyr Phe Pro Ser Glu Pro Gly Phe Cys Ile His Tyr Asn Ile
1               5                   10                  15

<210> SEQ ID NO 65
<211> LENGTH: 15
<212> TYPE: PRT
<213> ORGANISM: artificial
<220> FEATURE:
<223> OTHER INFORMATION: synthetic peptide

<400> SEQUENCE: 65

```
Glu Pro Gly Phe Cys Ile His Tyr Asn Ile Val Met Pro Gln Phe
1               5                   10                  15
```

<210> SEQ ID NO 66
<211> LENGTH: 15
<212> TYPE: PRT
<213> ORGANISM: artificial
<220> FEATURE:
<223> OTHER INFORMATION: synthetic peptide

<400> SEQUENCE: 66

```
Ile His Tyr Asn Ile Val Met Pro Gln Phe Thr Glu Ala Val Ser
1               5                   10                  15
```

<210> SEQ ID NO 67
<211> LENGTH: 15
<212> TYPE: PRT
<213> ORGANISM: artificial
<220> FEATURE:
<223> OTHER INFORMATION: synthetic peptide

<400> SEQUENCE: 67

```
Val Met Pro Gln Phe Thr Glu Ala Val Ser Pro Ser Val Leu Pro
1               5                   10                  15
```

<210> SEQ ID NO 68
<211> LENGTH: 15
<212> TYPE: PRT
<213> ORGANISM: artificial
<220> FEATURE:
<223> OTHER INFORMATION: synthetic peptide

<400> SEQUENCE: 68

```
Thr Glu Ala Val Ser Pro Ser Val Leu Pro Pro Ser Ala Leu Pro
1               5                   10                  15
```

<210> SEQ ID NO 69
<211> LENGTH: 15
<212> TYPE: PRT
<213> ORGANISM: artificial
<220> FEATURE:
<223> OTHER INFORMATION: synthetic peptide

<400> SEQUENCE: 69

```
Pro Ser Val Leu Pro Pro Ser Ala Leu Pro Leu Asp Leu Leu Asn
1               5                   10                  15
```

<210> SEQ ID NO 70
<211> LENGTH: 15
<212> TYPE: PRT
<213> ORGANISM: artificial
<220> FEATURE:
<223> OTHER INFORMATION: synthetic peptide

<400> SEQUENCE: 70

```
Pro Ser Ala Leu Pro Leu Asp Leu Leu Asn Asn Ala Ile Thr Ala
1               5                   10                  15
```

<210> SEQ ID NO 71
<211> LENGTH: 15
<212> TYPE: PRT
<213> ORGANISM: artificial
<220> FEATURE:
<223> OTHER INFORMATION: synthetic peptide

<400> SEQUENCE: 71

```
Leu Asp Leu Leu Asn Asn Ala Ile Thr Ala Phe Ser Thr Leu Glu
```

-continued

```
<210> SEQ ID NO 72
<211> LENGTH: 15
<212> TYPE: PRT
<213> ORGANISM: artificial
<220> FEATURE:
<223> OTHER INFORMATION: synthetic peptide

<400> SEQUENCE: 72

Asn Ala Ile Thr Ala Phe Ser Thr Leu Glu Asp Leu Ile Arg Tyr
1               5                   10                  15

<210> SEQ ID NO 73
<211> LENGTH: 15
<212> TYPE: PRT
<213> ORGANISM: artificial
<220> FEATURE:
<223> OTHER INFORMATION: synthetic peptide

<400> SEQUENCE: 73

Phe Ser Thr Leu Glu Asp Leu Ile Arg Tyr Leu Glu Pro Glu Arg
1               5                   10                  15

<210> SEQ ID NO 74
<211> LENGTH: 15
<212> TYPE: PRT
<213> ORGANISM: artificial
<220> FEATURE:
<223> OTHER INFORMATION: synthetic peptide

<400> SEQUENCE: 74

Asp Leu Ile Arg Tyr Leu Glu Pro Glu Arg Trp Gln Leu Asp Leu
1               5                   10                  15

<210> SEQ ID NO 75
<211> LENGTH: 15
<212> TYPE: PRT
<213> ORGANISM: artificial
<220> FEATURE:
<223> OTHER INFORMATION: synthetic peptide

<400> SEQUENCE: 75

Leu Glu Pro Glu Arg Trp Gln Leu Asp Leu Glu Asp Leu Tyr Arg
1               5                   10                  15

<210> SEQ ID NO 76
<211> LENGTH: 15
<212> TYPE: PRT
<213> ORGANISM: artificial
<220> FEATURE:
<223> OTHER INFORMATION: synthetic peptide

<400> SEQUENCE: 76

Trp Gln Leu Asp Leu Glu Asp Leu Tyr Arg Pro Thr Trp Gln Leu
1               5                   10                  15

<210> SEQ ID NO 77
<211> LENGTH: 15
<212> TYPE: PRT
<213> ORGANISM: artificial
<220> FEATURE:
<223> OTHER INFORMATION: synthetic peptide

<400> SEQUENCE: 77

Glu Asp Leu Tyr Arg Pro Thr Trp Gln Leu Leu Gly Lys Ala Phe
1               5                   10                  15
```

```
<210> SEQ ID NO 78
<211> LENGTH: 15
<212> TYPE: PRT
<213> ORGANISM: artificial
<220> FEATURE:
<223> OTHER INFORMATION: synthetic peptide

<400> SEQUENCE: 78

Pro Thr Trp Gln Leu Leu Gly Lys Ala Phe Val Phe Gly Arg Lys
1               5                   10                  15

<210> SEQ ID NO 79
<211> LENGTH: 15
<212> TYPE: PRT
<213> ORGANISM: artificial
<220> FEATURE:
<223> OTHER INFORMATION: synthetic peptide

<400> SEQUENCE: 79

Leu Gly Lys Ala Phe Val Phe Gly Arg Lys Ser Arg Val Val Asp
1               5                   10                  15

<210> SEQ ID NO 80
<211> LENGTH: 15
<212> TYPE: PRT
<213> ORGANISM: artificial
<220> FEATURE:
<223> OTHER INFORMATION: synthetic peptide

<400> SEQUENCE: 80

Val Phe Gly Arg Lys Ser Arg Val Val Asp Leu Asn Leu Leu Thr
1               5                   10                  15

<210> SEQ ID NO 81
<211> LENGTH: 15
<212> TYPE: PRT
<213> ORGANISM: artificial
<220> FEATURE:
<223> OTHER INFORMATION: synthetic peptide

<400> SEQUENCE: 81

Ser Arg Val Val Asp Leu Asn Leu Leu Thr Glu Glu Val Arg Leu
1               5                   10                  15

<210> SEQ ID NO 82
<211> LENGTH: 15
<212> TYPE: PRT
<213> ORGANISM: artificial
<220> FEATURE:
<223> OTHER INFORMATION: synthetic peptide

<400> SEQUENCE: 82

Leu Asn Leu Leu Thr Glu Glu Val Arg Leu Tyr Ser Cys Thr Pro
1               5                   10                  15

<210> SEQ ID NO 83
<211> LENGTH: 15
<212> TYPE: PRT
<213> ORGANISM: artificial
<220> FEATURE:
<223> OTHER INFORMATION: synthetic peptide

<400> SEQUENCE: 83

Glu Glu Val Arg Leu Tyr Ser Cys Thr Pro Arg Asn Phe Ser Val
1               5                   10                  15
```

<210> SEQ ID NO 84
<211> LENGTH: 15
<212> TYPE: PRT
<213> ORGANISM: artificial
<220> FEATURE:
<223> OTHER INFORMATION: synthetic peptide

<400> SEQUENCE: 84

```
Tyr Ser Cys Thr Pro Arg Asn Phe Ser Val Ser Ile Arg Glu Glu
1               5                   10                  15
```

<210> SEQ ID NO 85
<211> LENGTH: 15
<212> TYPE: PRT
<213> ORGANISM: artificial
<220> FEATURE:
<223> OTHER INFORMATION: synthetic peptide

<400> SEQUENCE: 85

```
Arg Asn Phe Ser Val Ser Ile Arg Glu Glu Leu Lys Arg Thr Asp
1               5                   10                  15
```

<210> SEQ ID NO 86
<211> LENGTH: 15
<212> TYPE: PRT
<213> ORGANISM: artificial
<220> FEATURE:
<223> OTHER INFORMATION: synthetic peptide

<400> SEQUENCE: 86

```
Ser Ile Arg Glu Glu Leu Lys Arg Thr Asp Thr Ile Phe Trp Pro
1               5                   10                  15
```

<210> SEQ ID NO 87
<211> LENGTH: 15
<212> TYPE: PRT
<213> ORGANISM: artificial
<220> FEATURE:
<223> OTHER INFORMATION: synthetic peptide

<400> SEQUENCE: 87

```
Leu Lys Arg Thr Asp Thr Ile Phe Trp Pro Gly Cys Leu Leu Val
1               5                   10                  15
```

<210> SEQ ID NO 88
<211> LENGTH: 15
<212> TYPE: PRT
<213> ORGANISM: artificial
<220> FEATURE:
<223> OTHER INFORMATION: synthetic peptide

<400> SEQUENCE: 88

```
Thr Ile Phe Trp Pro Gly Cys Leu Leu Val Lys Arg Cys Gly Gly
1               5                   10                  15
```

<210> SEQ ID NO 89
<211> LENGTH: 15
<212> TYPE: PRT
<213> ORGANISM: artificial
<220> FEATURE:
<223> OTHER INFORMATION: synthetic peptide

<400> SEQUENCE: 89

```
Gly Cys Leu Leu Val Lys Arg Cys Gly Gly Asn Cys Ala Cys Cys
1               5                   10                  15
```

```
<210> SEQ ID NO 90
<211> LENGTH: 15
<212> TYPE: PRT
<213> ORGANISM: artificial
<220> FEATURE:
<223> OTHER INFORMATION: synthetic peptide

<400> SEQUENCE: 90

Lys Arg Cys Gly Gly Asn Cys Ala Cys Cys Leu His Asn Cys Asn
1               5                   10                  15

<210> SEQ ID NO 91
<211> LENGTH: 15
<212> TYPE: PRT
<213> ORGANISM: artificial
<220> FEATURE:
<223> OTHER INFORMATION: synthetic peptide

<400> SEQUENCE: 91

Asn Cys Ala Cys Cys Leu His Asn Cys Asn Glu Cys Gln Cys Val
1               5                   10                  15

<210> SEQ ID NO 92
<211> LENGTH: 15
<212> TYPE: PRT
<213> ORGANISM: artificial
<220> FEATURE:
<223> OTHER INFORMATION: synthetic peptide

<400> SEQUENCE: 92

Leu His Asn Cys Asn Glu Cys Gln Cys Val Pro Ser Lys Val Thr
1               5                   10                  15

<210> SEQ ID NO 93
<211> LENGTH: 15
<212> TYPE: PRT
<213> ORGANISM: artificial
<220> FEATURE:
<223> OTHER INFORMATION: synthetic peptide

<400> SEQUENCE: 93

Glu Cys Gln Cys Val Pro Ser Lys Val Thr Lys Lys Tyr His Glu
1               5                   10                  15

<210> SEQ ID NO 94
<211> LENGTH: 15
<212> TYPE: PRT
<213> ORGANISM: artificial
<220> FEATURE:
<223> OTHER INFORMATION: synthetic peptide

<400> SEQUENCE: 94

Pro Ser Lys Val Thr Lys Lys Tyr His Glu Val Leu Gln Leu Arg
1               5                   10                  15

<210> SEQ ID NO 95
<211> LENGTH: 15
<212> TYPE: PRT
<213> ORGANISM: artificial
<220> FEATURE:
<223> OTHER INFORMATION: synthetic peptide

<400> SEQUENCE: 95

Lys Lys Tyr His Glu Val Leu Gln Leu Arg Pro Lys Thr Gly Val
1               5                   10                  15

<210> SEQ ID NO 96
```

```
<211> LENGTH: 15
<212> TYPE: PRT
<213> ORGANISM: artificial
<220> FEATURE:
<223> OTHER INFORMATION: synthetic peptide

<400> SEQUENCE: 96

Val Leu Gln Leu Arg Pro Lys Thr Gly Val Arg Gly Leu His Lys
1               5                   10                  15

<210> SEQ ID NO 97
<211> LENGTH: 15
<212> TYPE: PRT
<213> ORGANISM: artificial
<220> FEATURE:
<223> OTHER INFORMATION: synthetic peptide

<400> SEQUENCE: 97

Pro Lys Thr Gly Val Arg Gly Leu His Lys Ser Leu Thr Asp Val
1               5                   10                  15

<210> SEQ ID NO 98
<211> LENGTH: 15
<212> TYPE: PRT
<213> ORGANISM: artificial
<220> FEATURE:
<223> OTHER INFORMATION: synthetic peptide

<400> SEQUENCE: 98

Arg Gly Leu His Lys Ser Leu Thr Asp Val Ala Leu Glu His His
1               5                   10                  15

<210> SEQ ID NO 99
<211> LENGTH: 15
<212> TYPE: PRT
<213> ORGANISM: artificial
<220> FEATURE:
<223> OTHER INFORMATION: synthetic peptide

<400> SEQUENCE: 99

Ser Leu Thr Asp Val Ala Leu Glu His His Glu Glu Cys Asp Cys
1               5                   10                  15

<210> SEQ ID NO 100
<211> LENGTH: 15
<212> TYPE: PRT
<213> ORGANISM: artificial
<220> FEATURE:
<223> OTHER INFORMATION: synthetic peptide

<400> SEQUENCE: 100

Ala Leu Glu His His Glu Glu Cys Asp Cys Val Cys Arg Gly Ser
1               5                   10                  15

<210> SEQ ID NO 101
<211> LENGTH: 13
<212> TYPE: PRT
<213> ORGANISM: artificial
<220> FEATURE:
<223> OTHER INFORMATION: synthetic peptide

<400> SEQUENCE: 101

Glu Glu Cys Asp Cys Val Cys Arg Gly Ser Thr Gly Gly
1               5                   10

<210> SEQ ID NO 102
<211> LENGTH: 119
```

-continued

<212> TYPE: PRT
<213> ORGANISM: artificial
<220> FEATURE:
<223> OTHER INFORMATION: humanized variable heavy chain murine
      monoclonal antibody 5H7

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Thr Pro Gly Lys Gly Leu Glu Trp Val
        35                  40                  45

Ala Thr Ile Gly Tyr Gly Gly Ser Phe Thr Tyr Tyr Pro Asp Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ala Pro Leu Trp Asp Tyr Phe Asp Tyr Trp Gly Gln Gly
            100                 105                 110

Thr Leu Leu Thr Val Ser Ser
        115

<210> SEQ ID NO 103
<211> LENGTH: 112
<212> TYPE: PRT
<213> ORGANISM: artificial
<220> FEATURE:
<223> OTHER INFORMATION: humanized variable light chain murine
      monoclonal antibody 5H7

<400> SEQUENCE: 103

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Thr Ile Val His Ser
            20                  25                  30

Asp Gly Thr Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Gln Gly Thr Lys Leu Glu Ile Lys
            100                 105                 110

<210> SEQ ID NO 104
<211> LENGTH: 119
<212> TYPE: PRT
<213> ORGANISM: artificial
<220> FEATURE:
<223> OTHER INFORMATION: humanized variable heavy chain murine
      monoclonal antibody 16B1

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr

```
                    20                  25                  30
Gly Met Ser Trp Val Arg Gln Thr Pro Gly Lys Gly Leu Glu Trp Val
                35                  40                  45
Ala Thr Ile Gly Ser Gly Gly Ser Tyr Thr Tyr Tyr Pro Asp Ser Val
            50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gln Ala Pro Leu Trp Asp Tyr Ser Asp Tyr Trp Gly Gln Gly
                100                 105                 110
Thr Leu Leu Thr Val Ser Ser
        115

<210> SEQ ID NO 105
<211> LENGTH: 112
<212> TYPE: PRT
<213> ORGANISM: artificial
<220> FEATURE:
<223> OTHER INFORMATION: humanized variable light chain murine
      monoclonal antibody 16B1

<400> SEQUENCE: 105

Asp Val Val Met Thr Gln Ser Pro Leu Ser Leu Pro Val Thr Leu Gly
1               5                   10                  15
Gln Pro Ala Ser Ile Ser Cys Arg Ser Asn Gln Ser Ile Val His Ser
                20                  25                  30
Asn Gly Asp Thr Tyr Leu Glu Trp Tyr Leu Gln Lys Pro Gly Gln Ser
                35                  40                  45
Pro Arg Leu Leu Ile Tyr Lys Val Ser Asn Arg Phe Ser Gly Val Pro
            50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Pro Thr Phe Gly Gln Gly Thr Lys Leu Glu Ile Lys
                100                 105                 110

<210> SEQ ID NO 106
<211> LENGTH: 119
<212> TYPE: PRT
<213> ORGANISM: artificial
<220> FEATURE:
<223> OTHER INFORMATION: humanized variable heavy chain murine
      monoclonal antibody 29 H1

<400> SEQUENCE: 106

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
                20                  25                  30
Gly Met Ser Trp Val Arg Gln Thr Pro Gly Lys Gly Leu Glu Trp Val
                35                  40                  45
Ala Thr Ile Gly Ser Gly Gly His Tyr Thr Tyr Tyr Pro Asp Ser Val
            50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
```

```
                            85                  90                  95
Ala Arg Gln Ala Pro Leu Trp Asp Cys Ser Asp Tyr Trp Gly Gln Gly
                100                 105                 110

Thr Leu Leu Thr Val Ser Ser
        115

<210> SEQ ID NO 107
<211> LENGTH: 112
<212> TYPE: PRT
<213> ORGANISM: artificial
<220> FEATURE:
<223> OTHER INFORMATION: humanized variable light chain murine
      monoclonal antibody 29 H1

<400> SEQUENCE: 107

Asp Val Val Met Thr Gln Ser Pro Leu Ser Leu Pro Val Thr Leu Gly
1               5                   10                  15

Gln Pro Ala Ser Ile Ser Cys Arg Ser Gln Thr Ile Val His Ser
            20                  25                  30

Asp Gly Thr Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Gln Gly Thr Lys Leu Glu Ile Lys
            100                 105                 110

<210> SEQ ID NO 108
<211> LENGTH: 357
<212> TYPE: DNA
<213> ORGANISM: artificial
<220> FEATURE:
<223> OTHER INFORMATION: humanized variable heavy chain murine
      monoclonal antibody 5H7

<400> SEQUENCE: 108
gaggtgcagc ttctggaatc tgggggaggt cttgtgcagc caggagggtc cctgcggctc        60
tcctgtgccg catctggatt cactttcagt agctatggca tgtcttgggt tcgccagact       120
cctggcaaag gctggagtg gtcgcaacc attggctatg gtgggagttt cacctactat        180
ccagattcaa tgaagggacg ctttaccatc agcagagaca tgccaagaa cccttgtac        240 ctgcaaatga cagtctgcg agccgaagac acagccgtgt actattgcgc taggcaggct       300
cccctctggg actactttga ttactggggc caaggcacat gctcacagt ctcctca          357

<210> SEQ ID NO 109
<211> LENGTH: 336
<212> TYPE: DNA
<213> ORGANISM: artificial
<220> FEATURE:
<223> OTHER INFORMATION: humanized variable light chain murine
      monoclonal antibody 5H7

<400> SEQUENCE: 109
gacgttgtga tgacccaatc tcccttgtcc ctgcctgtca ctcttgggca gcctgcctcc        60
attagctgtc gctctagcca gaccattgtg catagtgacg gcacaaccta cctggaatgg       120
tatcttcaga aaccaggcca gagcccacgg ctcctgatct acaaagtttc caacaggttt       180
```
agtggggtcc cagacaggtt ctccggcagt ggatcaggga cagatttcac actcaagata    240
agcagagtgg aggctgagga tgtgggagtc tactattgct ttcaaggttc acacgtacct    300
cccactttcg gccagggaac caagctggaa atcaag                               336

<210> SEQ ID NO 110
<211> LENGTH: 357
<212> TYPE: DNA
<213> ORGANISM: artificial
<220> FEATURE:
<223> OTHER INFORMATION: humanized variable heavy chain murine
      monoclonal antibody 16B1

<400> SEQUENCE: 110
gaggtgcagc ttctggaatc tggggggaggt cttgtgcagc caggagggtc cctgcggctc    60
tcctgtgccg catctggatt cactttcagt aattatggca tgtcttgggt tcgccagact    120
cctggcaaag gctggagtg gtcgcaacc attggcagtg gtgggagtta tacctactat      180
ccagattcag tgaagggacg ctttaccatc agcagagaca atgccaagaa cacccttgtac   240 ctgcaaatga acagtctgcg agccgaagac acagccgtgt actattgcgc taggcaggct    300
cccctctggg actacagcga ttactggggc caaggcacat gctcacagt ctcctca        357

<210> SEQ ID NO 111
<211> LENGTH: 336
<212> TYPE: DNA
<213> ORGANISM: artificial
<220> FEATURE:
<223> OTHER INFORMATION: humanized variable light chain murine
      monoclonal antibody 16B1

<400> SEQUENCE: 111
gacgttgtga tgacccaatc tcccttgtcc ctgcctgtca ctcttgggca gcctgcctcc    60
attagctgtc gctctaacca gagcattgtg catagtaacg gcgacaccta cctggaatgg   120
tatcttcaga aaccaggcca gagcccacgg ctcctgatct acaaagtttc caacaggttt    180
agtggggtcc cagacaggtt ctccggcagt ggatcaggga cagatttcac actcaagata    240
agcagagtgg aggctgagga tgtgggagtc tactattgct ttcaaggttc acacgtacct    300
cccactttcg gccagggaac caagctggaa atcaag                               336

<210> SEQ ID NO 112
<211> LENGTH: 357
<212> TYPE: DNA
<213> ORGANISM: artificial
<220> FEATURE:
<223> OTHER INFORMATION: humanized variable heavy chain murine
      monoclonal antibody 29 H1

<400> SEQUENCE: 112
gaggtgcagc ttctggaatc tggggggaggt cttgtgcagc caggagggtc cctgcggctc    60
tcctgtgccg catctggatt cactttcagt aattatggca tgtcttgggt tcgccagact    120
cctggcaaag gctggagtg gtcgcaacc attggcagtg gtgggcacta tacctactat      180
ccagattcag tgaagggacg ctttaccatc agcagagaca atgccaagaa cacccttgtac   240 ctgcaaatga acagtctgcg agccgaagac acagccgtgt actattgcgc taggcaggct    300
cccctctggg actgtagcga ttactggggc caaggcacat gctcacagt ctcctca        357

<210> SEQ ID NO 113
<211> LENGTH: 336

<212> TYPE: DNA
<213> ORGANISM: artificial
<220> FEATURE:
<223> OTHER INFORMATION: humanized variable light chain murine
      monoclonal antibody 29 H1

<400> SEQUENCE: 113

```
gacgttgtga tgacccaatc tcccttgtcc ctgcctgtca ctcttgggca gcctgcctcc      60
attagctgtc gctctagcca gaccattgtg catagtgacg gcacaaccta cctggaatgg     120
tatcttcaga aaccaggcca gagcccacgg ctcctgatct acaaagtttc caacaggttt     180
agtggggtcc cagacaggtt ctccggcagt ggatcaggga cagatttcac actcaagata     240
agcagagtgg aggctgagga tgtgggagtc tactattgct ttcaaggttc acacgtacct     300
cccactttcg gccagggaac caagctggaa atcaag                              336
```